US008355926B1

(12) United States Patent
Hinz et al.

(10) Patent No.: US 8,355,926 B1
(45) Date of Patent: *Jan. 15, 2013

(54) HEALTH AND LIFE SCIENCES MEDICAID HIGH PERFORMANCE CAPABILITY ASSESSMENT

(75) Inventors: Stephen Hinz, Lexington, KY (US); Cindy Hielscher, Austin, TX (US)

(73) Assignee: Accenture Global Services Limited, Dublin (IE)

( * ) Notice: Subject to any disclaimer, the term of this patent is extended or adjusted under 35 U.S.C. 154(b) by 156 days.

This patent is subject to a terminal disclaimer.

(21) Appl. No.: 12/701,914

(22) Filed: Feb. 8, 2010

(51) Int. Cl.
*G06Q 10/00* (2012.01)
*G06F 19/00* (2011.01)

(52) U.S. Cl. .................................. 705/2; 705/3

(58) Field of Classification Search .................... 705/2, 3
See application file for complete search history.

(56) References Cited

U.S. PATENT DOCUMENTS

| | | | |
|---|---|---|---|
| 6,256,773 B1 | 7/2001 | Bowman-Amuah | |
| 6,324,647 B1 | 11/2001 | Bowman-Amuah | |
| 6,370,573 B1 | 4/2002 | Bowman-Amuah | |
| 6,601,233 B1 | 7/2003 | Underwood | |
| 6,957,186 B1 | 10/2005 | Guheen et al. | |
| 2002/0035495 A1 | 3/2002 | Spira et al. | |
| 2003/0083912 A1* | 5/2003 | Covington et al. | 705/7 |
| 2003/0110067 A1 | 6/2003 | Miller et al. | |
| 2004/0098299 A1* | 5/2004 | Ligon et al. | 705/10 |

OTHER PUBLICATIONS

Brochure, "High Performance Acceleration: Global Retail Process Model," Accenture, High Performance Delivered, 2007.

Handbook, Software Engineering Institute, "A Description of the Systems Engineering Capability Maturity Model Appraisal Method Version 1.1," Mar. 1996.
Keith A. Heston, "Achieving Delivery Excellence Using the Capability Maturity Model Integration," Accenture, *High Performance Delivered*, 2006.
Report, Software Engineering Institute, "A Systems Engineering Capability Maturity Model, Version 1.1.," Nov. 1995.
Walker Royce, "CMM vs. CMMI: From Conventional to Modern Software Management," *The Rational Edge*, 2002.
U.S. Appl. No. 11/823,112, filed Jun. 25, 2007.
U.S. Appl. No. 12/124,010, filed May 20, 2008.
U.S. Appl. No. 12/129,080, filed May 29, 2008.
U.S. Appl. No. 61/086,927, filed Aug. 7, 2008.
U.S. Appl. No. 12/194,793, filed Aug. 20, 2008.
U.S. Appl. No. 61/092,225, filed Aug. 27, 2008.
U.S. Appl. No. 12/324,150, filed Nov. 26, 2008.
U.S. Appl. No. 61/154,832, filed Feb. 24, 2009.
U.S. Appl. No. 61/154,945, filed Feb. 24, 2009.
U.S. Appl. No. 61/164,640, filed Mar. 30, 2009.
U.S. Appl. No. 61/164,618, filed Mar. 30, 2009.
U.S. Appl. No. 12/427,201, filed Apr. 21, 2009.
U.S. Appl. No. 12/471,767, filed May 26, 2009.

(Continued)

*Primary Examiner* — Robert Morgan
*Assistant Examiner* — Sean K Hunter
(74) *Attorney, Agent, or Firm* — Brinks Hofer Gilson & Lione

(57) ABSTRACT

A high-performance capability assessment model helps a Medicaid program meet the challenges of the health market. As a result, the Medicaid program can achieve the clarity, consistency, and well-defined execution of core processes that reduce inefficiencies and waste that result from unnecessary process complexity and exceptions. In addition, the high-performance capability assessment model helps the Medicaid program to identify specific areas in which improvements may be made, to understand how to make said improvements, and to establish levels of capability along the way to reaching an ultimate capability goal.

15 Claims, 15 Drawing Sheets

OTHER PUBLICATIONS

U.S. Appl. No. 12/479,310, filed Jun. 5, 2009.
U.S. Appl. No. 12/548,673, filed Aug. 27, 2009.
U.S. Appl. No. 12/710,900, filed Feb. 23, 2010.
U.S. Appl. No. 12/710,662, filed Feb. 23, 2010.
U.S. Appl. No. 12/713,647, filed Feb. 26, 2010.
U.S. Appl. No. 12/713,597, filed Feb. 26, 2010.
Non-Final Office Action dated Apr. 28, 2011, issued in related U.S. Appl. No. 12/129,080.

* cited by examiner

HEALTH AND LIFE SCIENCES MEDICAID HIGH PERFORMANCE CAPABILITY ASSESSMENT

BACKGROUND OF THE INVENTION

1. Technical Field

This disclosure concerns a system and method for identifying the performance of an organization on a scale of mastery across representative capabilities of the organization's industry. In particular, this disclosure relates to an efficient and cost effective way to assess the performance level of key capability areas within the processes of a Medicaid program.

2. Background Information

Modern Medicaid programs operate in an increasingly challenging environment. To survive, Medicaid programs must adapt to this environment and execute in a clear, consistent, and efficient manner. Furthermore, the competitive nature, regulatory requirements, low profit margins, and competitive challenges of Medicaid programs greatly increase the complexity and difficulty of surviving on a day-to-day basis.

Despite the need for Medicaid programs to meet the challenges of the health-related market, it is still often the case that the programs lack clarity, consistency, and well-defined execution of its core processes. These shortcomings severely constrain the programs, and lead directly to inefficiencies and waste due to unnecessary complexity, process exceptions, and customer dissatisfaction. At the same time, it can be very difficult to identify specific processes to which improvements may be made, either because the program management itself does not have the expertise to identify the processes or because the complexities of the programs frustrate attempts to clearly delineate the processes to be improved.

Even if the Medicaid programs, on their own, could identify one of the many processes that it needs to improve, the business or management would not necessarily know how to improve the process or be able to identify a concrete and measurable improvement goal. Another difficulty exists in determining whether there are any intermediate goals that should be reached along the way. As Medicaid programs struggle to meet the demands of the modern economic and health landscape, they fail to identify opportunities for maximizing efficiency, category expansion, multi-channel execution, customer satisfaction, and to reach other important goals.

Therefore, a need exists for an efficient and effective system and method to assess the performance level of key assessment areas within the processes of a Medicaid program.

SUMMARY

A high-performance capability assessment (HPCA) model helps a Medicaid program meet the challenges of the market segment by defining a scale of performance mastery along which the current practices of the program may be located. The HPCA model accelerates the discovery of process and performance gaps within program operations. In addition, the HPCA model also helps the program to identify specific areas in which improvements may be made, how to make the improvements, and how to establish performance measures during the course of attempting to achieve an ultimate goal. As a result, the programs can achieve the clarity, consistency, and well-defined execution of core processes that maximize the operating budget for optimum outcomes.

The HPCA model includes a key factor dimension and a performance mastery scale dimension. The performance mastery scale dimension defines multiple mastery levels. The performance mastery levels form a scale of increasing organizational performance. The scale includes a 'Basic' mastery level, a 'Competitive' mastery level, and a 'Market Leading' mastery level along a horizontal axis. Each performance mastery level includes criteria specific to a corresponding key assessment area. Each key assessment area identifies some aspect of a capability of a Medicaid program.

A capability can be defined as a bundle of closely integrated skills, knowledge, technologies, and cumulative learning that is exercised through a set of processes and that collectively represents an program's ability to create value by producing outcomes and results. Capability areas do not represent a delineation of organizational responsibilities because the outcomes of a capability may be the result of a number of cross-functional teams. Capabilities of a business may be grouped into areas and/or platforms, including platforms and sub-platforms, depending on the organizational structure of the business.

For example, the HPCA model groups the capabilities of the Medicaid program into nine main areas or platforms, which may also be thought of as "program areas," namely a program management platform, a care management platform, a contractor management platform, a program integrity management platform, a business relationship management platform, a provider management platform, a member management platform, an operations management platform, and an enterprise platform. Each platform may include multiple sub-platforms. For example, the program integrity management platform may include three sub-platforms, namely an identify candidate case sub-platform, a manage case sub-platform, and a payment integrity sub-platform.

Some of the platforms and sub-platforms may include additional or further levels, while others may not, and may also include capabilities at their lowest level. Examples of capabilities within the program quality management sub-platform include, for example, a manage business performance capability and a manage quality, risk, and performance capability.

The key factor dimension establishes a set of key assessment areas in which to analyze the capabilities of a business. Key assessment areas include performance capability criteria. Performance capability criteria populate the performance capability assessment model. The performance capability criteria may be specific to any one of many different business capabilities. Any number of performance capability assessment models and performance capability criteria may be defined and stored in a capability detail pool for subsequent retrieval and application to a business under examination. Accordingly, the HPCA model provides a flexible and adaptive scale of performance capability against which business practices may be compared to ascertain where the capabilities of a program under examination fall along the scale.

Other systems, methods, features, and advantages will be, or will become, apparent to one with skill in the art upon examination of the following figures and detailed description. All such additional systems, methods, features, and advantages are included within this description, are within the scope of the invention, and are protected by the following claims.

BRIEF DESCRIPTION OF THE DRAWINGS

The Medicaid high-performance capability assessment model and system may be better understood with reference to the following drawings and description. The elements in the figures are not necessarily to scale, emphasis instead being placed upon illustrating the principles of the capability assessment techniques. In the figures, like-referenced numerals designate corresponding parts throughout the different views.

DETAILED DESCRIPTION OF THE PREFERRED EMBODIMENTS

Figure 1:
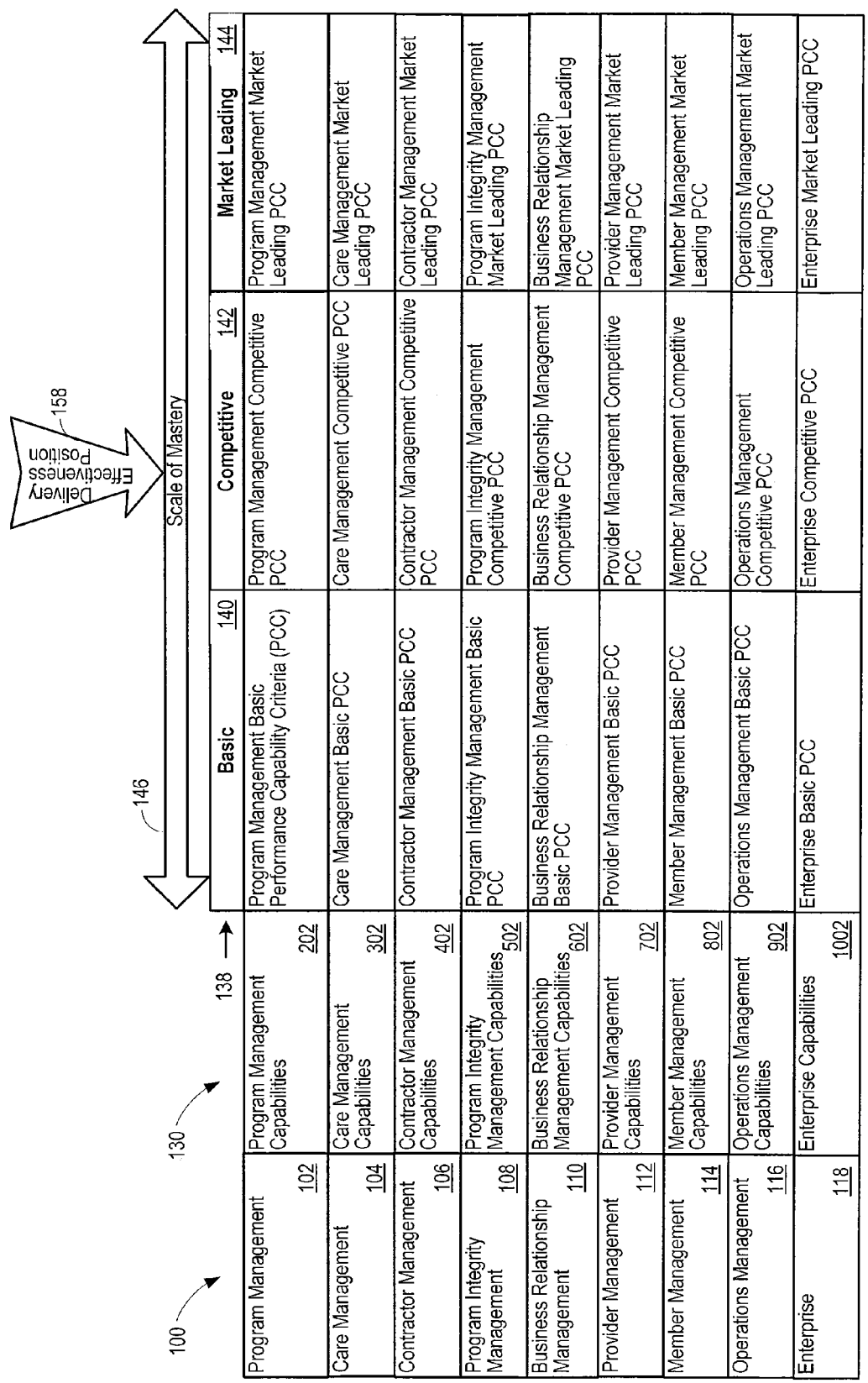
FIG. 1 shows a high-performance capability assessment model with a performance scale of mastery and performance criteria shown for different capabilities showing multiple platforms, including a program management platform, a care management platform, a contractor management platform, a program integrity management platform, a business relationship management platform, a provider management platform, a member management platform, an operations management platform, and an enterprise platform.

FIG. 1 shows a high-performance capability assessment (HPCA) model 100. The HPCA model 100 specifies nine platforms, including a program management platform 102, a care management platform 104, a contractor management platform 106, a program integrity management platform 108, a business relationship management platform 110, a provider management platform 112, a member management platform 114, an operations management platform 116, and an enterprise platform 118. Each platform 102, 104, 106, 108, 110, 112, 114, 116, and 118 may include sub-platforms. The HPCA model 100 is not limited to the form shown in FIG. 1. Instead, the HPCA model 100 may be adapted and modified to full a wide variety of analysis roles. Additional, different, or fewer platforms may be used in other implementations, with each platform defining additional, different, or fewer capabilities. Each platform and/or sub-platform includes one or more multiple <platform/sub-platform name>capabilities 130.

The HPCA model 100 establishes a multidimensional Medicaid program performance reference set that includes multiple key assessment performance levels 138, further described below in reference Tables 1-3. The performance levels 138 establish a scale of increasing effectiveness in delivery of each capability. The key assessment performance reference tables include a 'Basic' 140 delivery level, a 'Competitive' 142 delivery level, and a 'Market Leading' 144 delivery level. The performance levels establish a scale of mastery 146 along which current program practices may be located and identified with respect to any platform and capability within a platform according to an analysis of performance capability criteria (PCC). The capability under evaluation may be assigned the performance level 138 based on a delivery effectiveness position 158 along the scale of mastery 146.

The 'Basic' delivery level 140 specifies 'Basic' performance assessment criteria, the 'Competitive' delivery level 142 specifies 'Competitive' performance assessment criteria, and the 'Market Leading' delivery level 144 specifies 'Market Leading' performance assessment criteria. The HPCA model 100 receives input data that specifies a Medicaid program platform (e.g., a Medicaid program area) and a Medicaid program key assessment area for analysis. The HPCA model 100 searches the multidimensional Medicaid program performance reference set for a matching key assessment performance reference table that matches the Medicaid program platform and corresponding program capability within the platform and the Medicaid program key assessment area, and retrieves the matching key assessment performance reference table. The HPCA model 100 initiates analysis of the matching key assessment performance reference table to obtain a resultant performance assessment level for the Medicaid program key assessment area.

Tables 1-3 below provide an explanation of each of the capability levels 140, 142, and 144.

TABLE 1

'Basic' Delivery Level

| Description: | Capability mastery at the basic level is competitive on a domestic or local level and selectively on a global basis. |
|---|---|

TABLE 2

'Competitive' Delivery Level

| Description: | Capability mastery at a competitive level is in the top 50% of performers when compared to domestic and international peer groups. |
|---|---|

TABLE 3

'Market Leading' Delivery Level

| Description: | Capability mastery at a market leading level implies that few companies globally are performing at this level, and can include emerging capabilities where companies have committed significant levels of investment and resources. |
|---|---|

For FIGS. 2-10 the capability under evaluation may be assigned a level of mastery 138 based on the program's position along the scale of mastery 146 (e.g., the 'Basic,' 'Competitive,' or 'Market Leading' delivery level). Performance criteria corresponding to the basic 140, competitive 142, and market leading 144 performance levels populate the HPCA model 100. The performance criteria capture characteristics, and/or other features of the delivery of a capability at a particular performance level. Examples below illustrate performance criteria that provide analysis and benchmarking for Medicaid programs. The HPCA model 100 performance criteria provide a tool for determining where a platform and capability under examination fall along the scale of mastery 146.

For example, business consultants and business process engineers may interview a business or receive data about the business to determine, measure, or otherwise ascertain the characteristics, criteria, and other features of a particular capability implemented within the program. The consultants and engineers may compare the characteristics of the business to the performance criteria in the HPCA model 100 and arrive at an assessment level 138 for the capability under examination. In doing so, for example, the consultants and engineers may identify where the capability under examination falls in terms of the performance level for each key assessment area of a capability and determine an overall position on the scale of mastery 146 for the capability under examination. Performance criteria may populate the HPCA model 100 in whole or in part. Multiple high-performance capability assessments may be collected and stored with the performance criteria for future retrieval and possible modification in a capability detail pool, discussed below.

Figure 2:
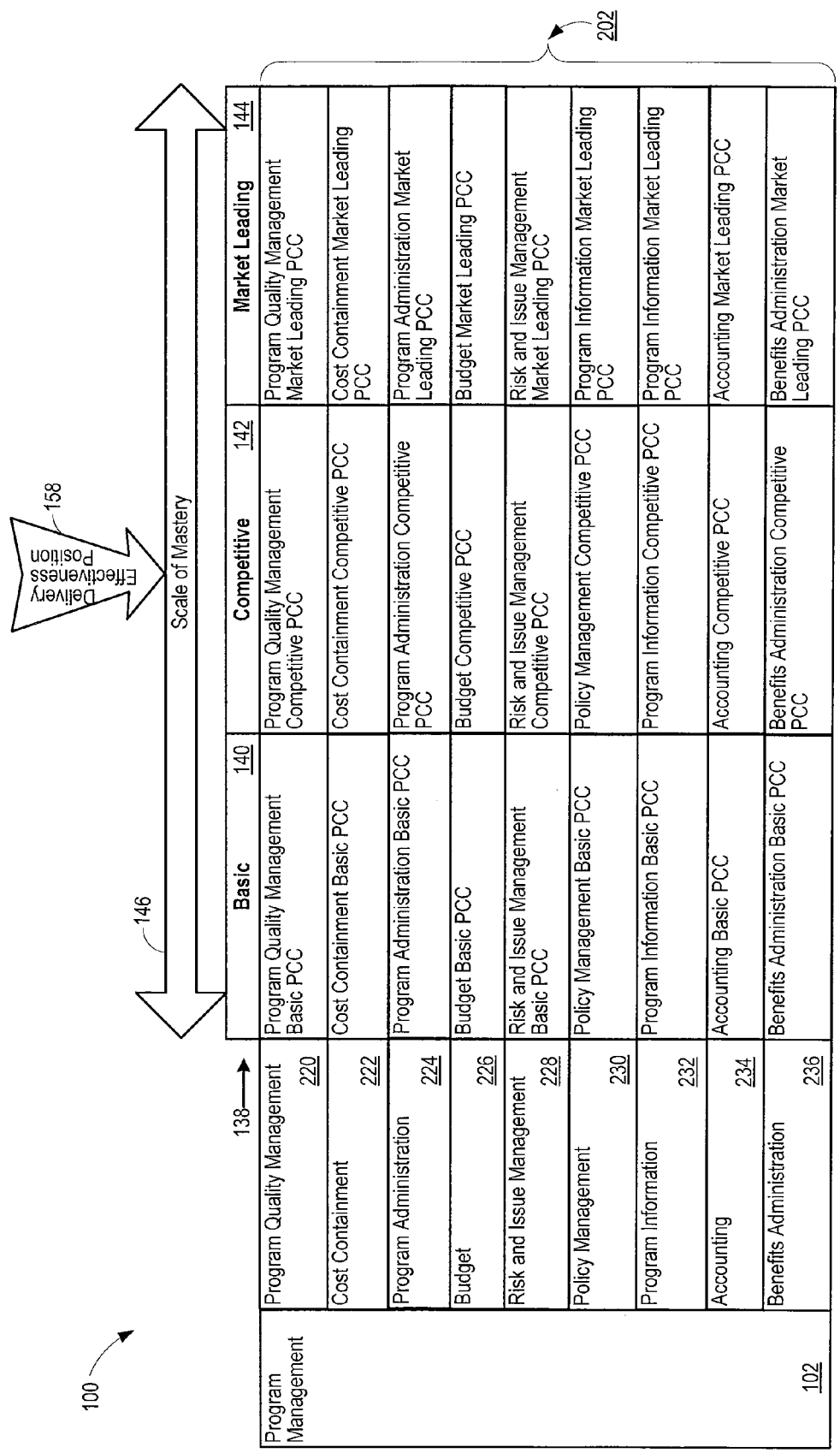
FIG. 2 shows a high-performance capability assessment model with capabilities for sub-platforms, including a program quality management sub-platform, a cost containment sub-platform, a program administration sub-platform, a budget sub-platform, a risk and issue management sub-platform, a policy management sub-platform, a program information sub-platform, an accounting sub-platform, and a benefits administration sub-platform, all corresponding to the program management platform.

FIG. 2 shows the program management platform 102 divided into respective capability areas 202. The program management platform 102 includes a program quality management sub-platform 220, a cost containment sub-platform 222, a program administration sub-platform 224, a budget sub-platform 226, a risk and issue management sub-platform 228, a policy management sub-platform 230, a program information sub-platform 232, an accounting sub-platform 234, and a benefits administration sub-platform 236.

Figure 3:
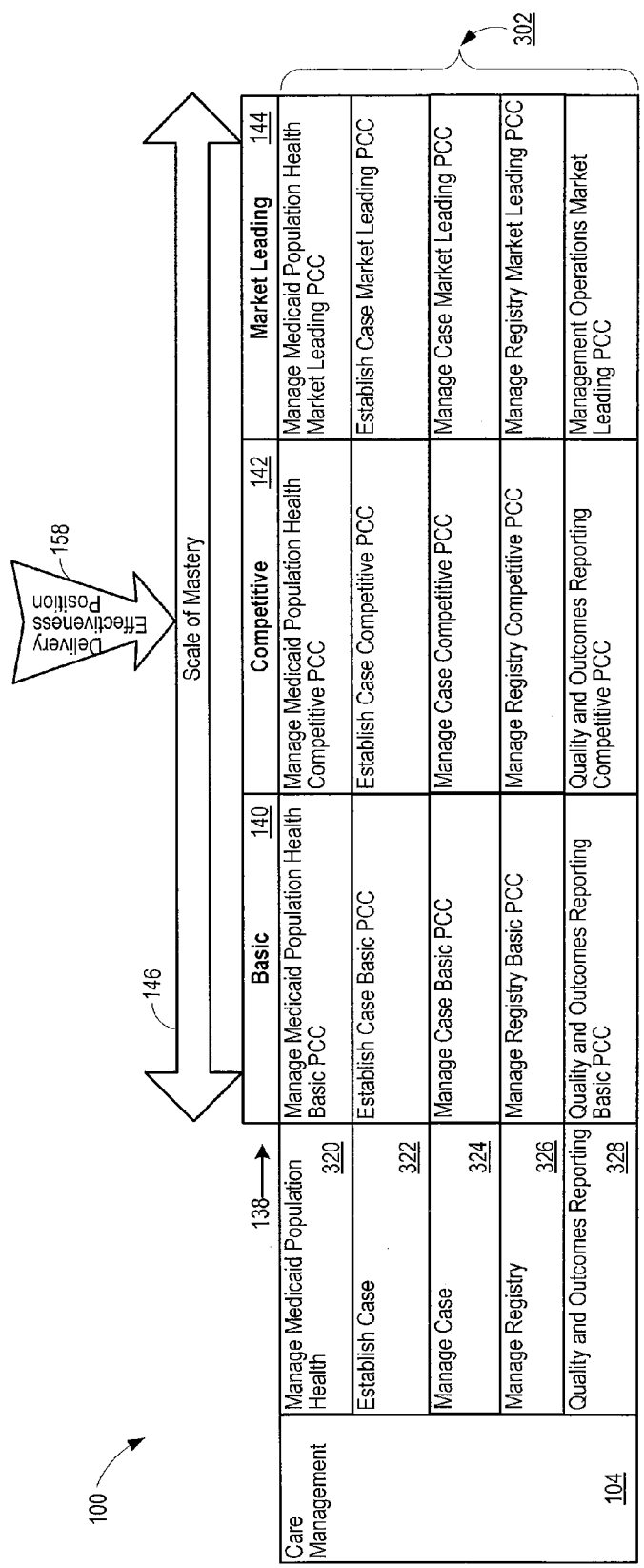
FIG. 3 shows a high-performance capability assessment model with capabilities for sub-platforms, including a manage Medicaid population health sub-platform, an establish case sub-platform, a manage case sub-platform, a manage registry sub-platform, and a quality and outcomes reporting sub-platform, all corresponding to the care management platform.

FIG. 3 shows the care management platform 104 divided into respective capability areas 302. The care management platform 104 includes a manage Medicaid population health sub-platform 320, an establish case sub-platform 322, a manage case sub-platform 324, a manage registry sub-platform 326, and a quality and outcomes reporting sub-platform 328.

Figure 4:
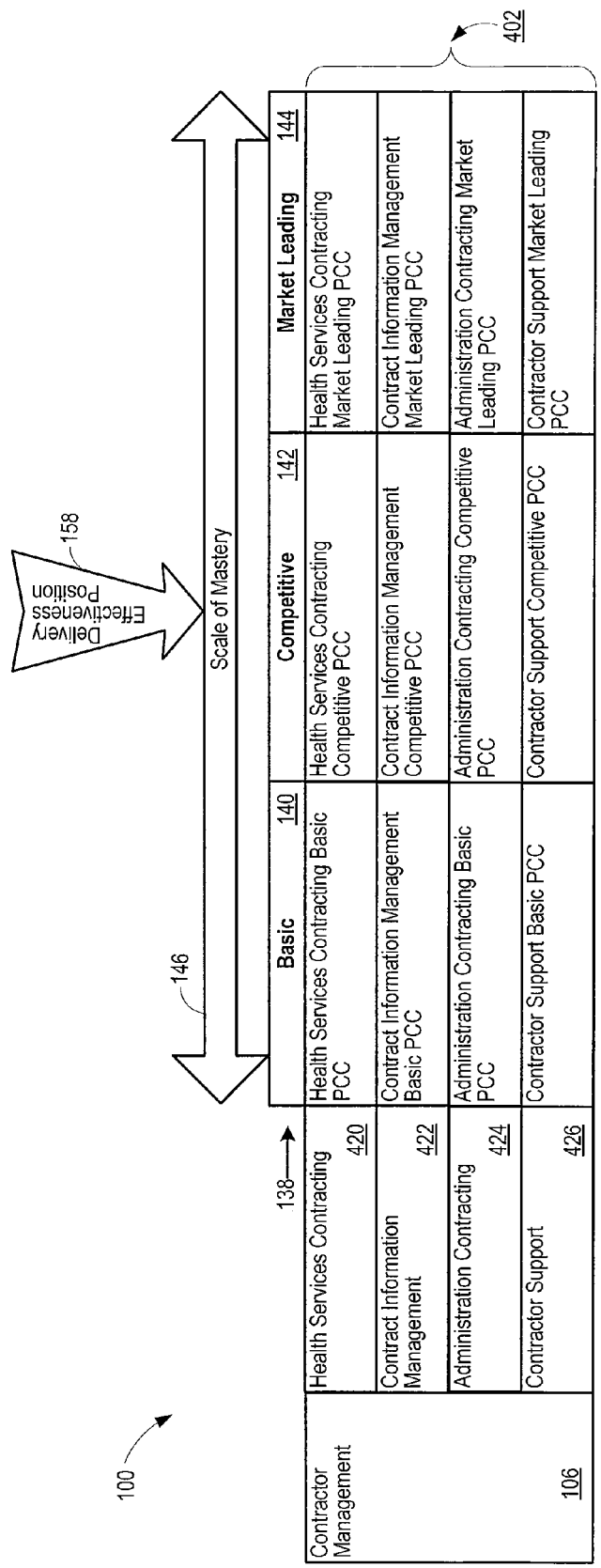
FIG. 4 shows a high-performance capability assessment model with capabilities for sub-platforms, including a health services contracting sub-platform, a contract information management sub-platform, an administration contracting sub-platform, and a contractor support sub-platform, all corresponding to the contractor management platform.

FIG. 4 shows the contractor management platform 106 divided into respective capability areas 402. The contractor management platform 106 includes a health services contracting sub-platform 420, a contract information management sub-platform 422, an administration contracting sub-platform 424, and a contractor support sub-platform 426.

Figure 5:
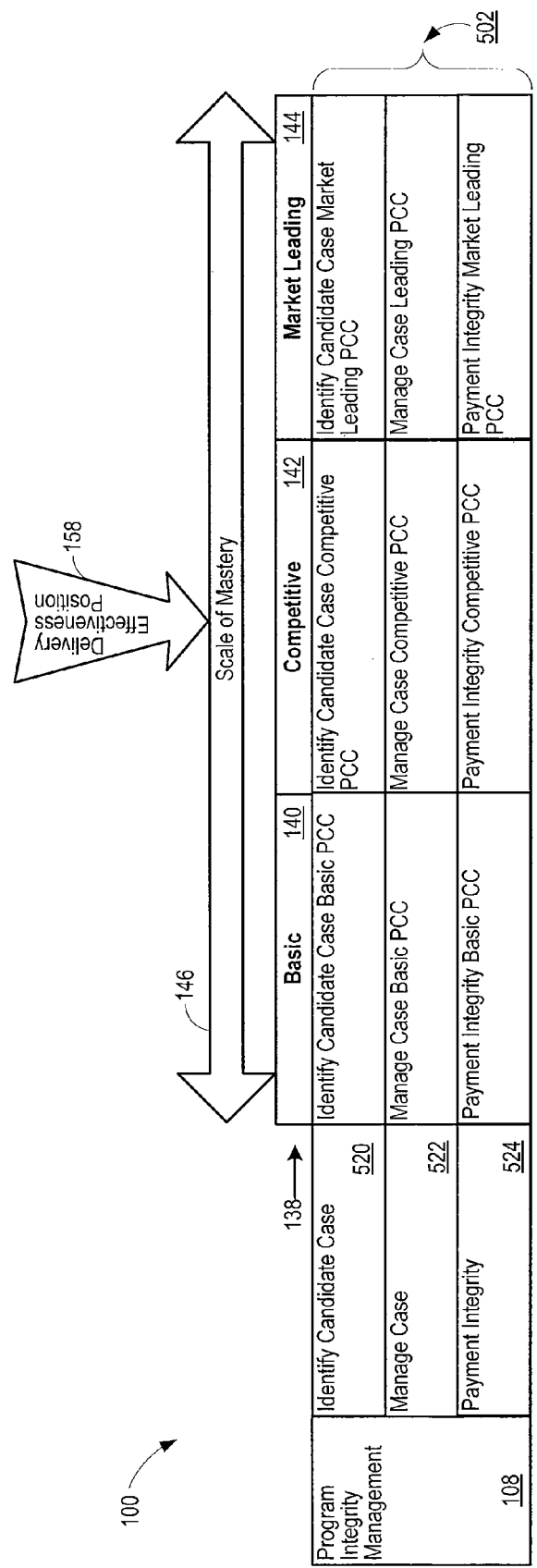
FIG. 5 shows a high-performance capability assessment model with capabilities for sub-platforms, including an identify candidate case sub-platform, a manage case sub-platform, and a payment integrity sub-platform, all corresponding to the program integrity management platform.

FIG. 5 shows the program integrity management platform 108 divided into respective capability areas 502. The program integrity management platform 108 includes an identify candidate case sub-platform 520, a manage case sub-platform 522, and a payment integrity sub-platform 524.

Figure 6:
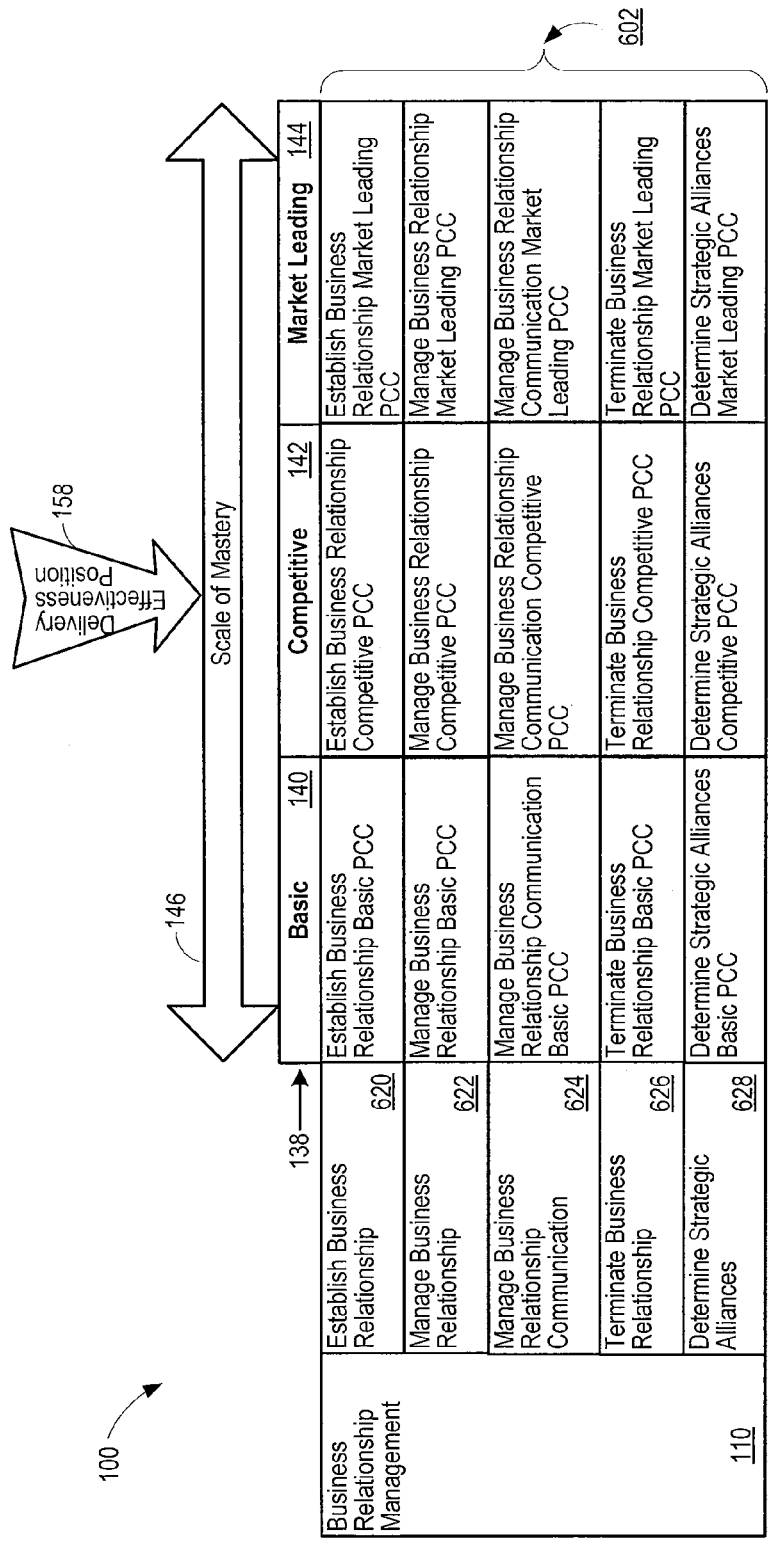
FIG. 6 shows a high-performance capability assessment model with capabilities for sub-platforms, including an establish business relationship sub-platform, a manage business relationship sub-platform, a manage business relationship communication sub-platform, a terminate business relationship sub-platform, and a determine strategic alliances sub-platform, all corresponding to the business relationship management platform.

FIG. 6 shows the business relationship management platform 110 divided into respective capability areas 602. The business relationship management platform 110 includes an establish business relationship sub-platform 620, a manage business relationship sub-platform 622, a manage business relationship communication sub-platform 624, a terminate business relationship sub-platform 626, and a determine strategic alliances sub-platform 628.

Figure 7:
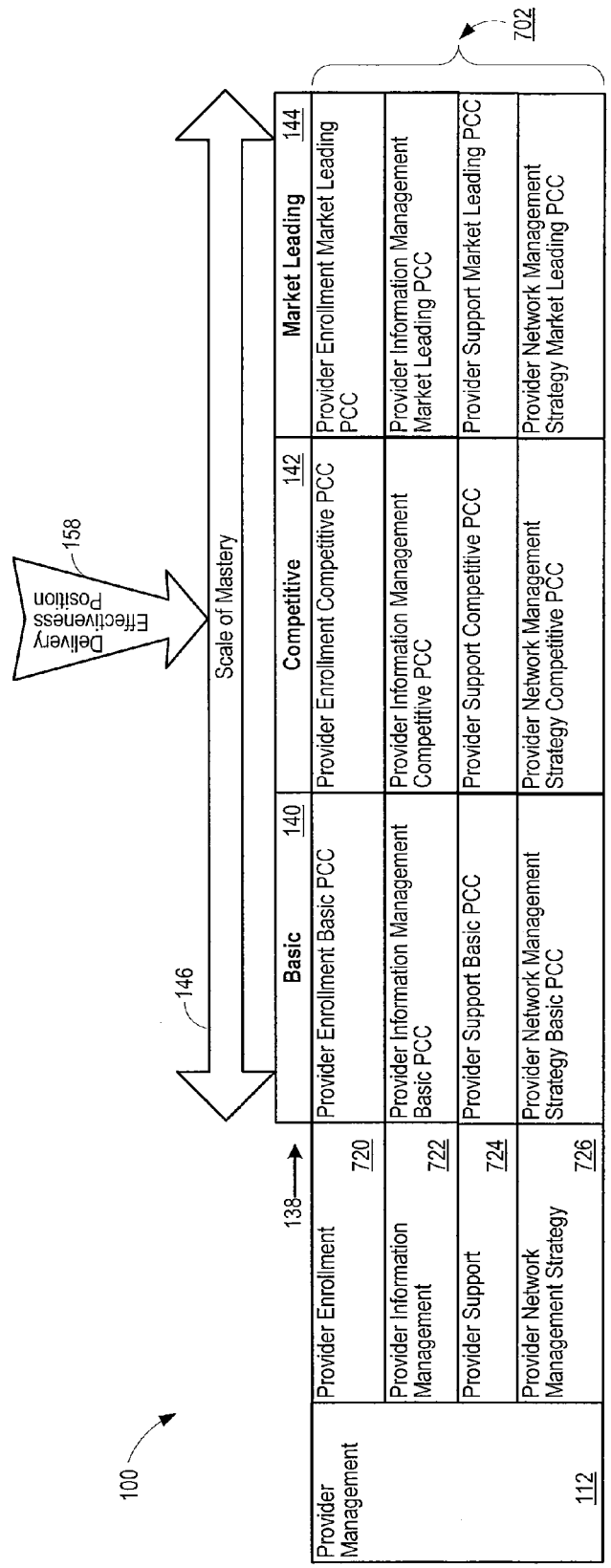
FIG. 7 shows a high-performance capability assessment model with capabilities for sub-platforms, including a provider enrollment sub-platform, a provider information management sub-platform, a provider support sub-platform, and a provider network management strategy sub-platform, all corresponding to the provider management platform.

FIG. 7 shows the provider management platform 112 divided into respective capability areas 702. The provider management platform 112 includes a provider enrollment sub-platform 720, a provider information management sub-platform 722, a provider support sub-platform 724, and a provider network management strategy sub-platform 726.

Figure 8:
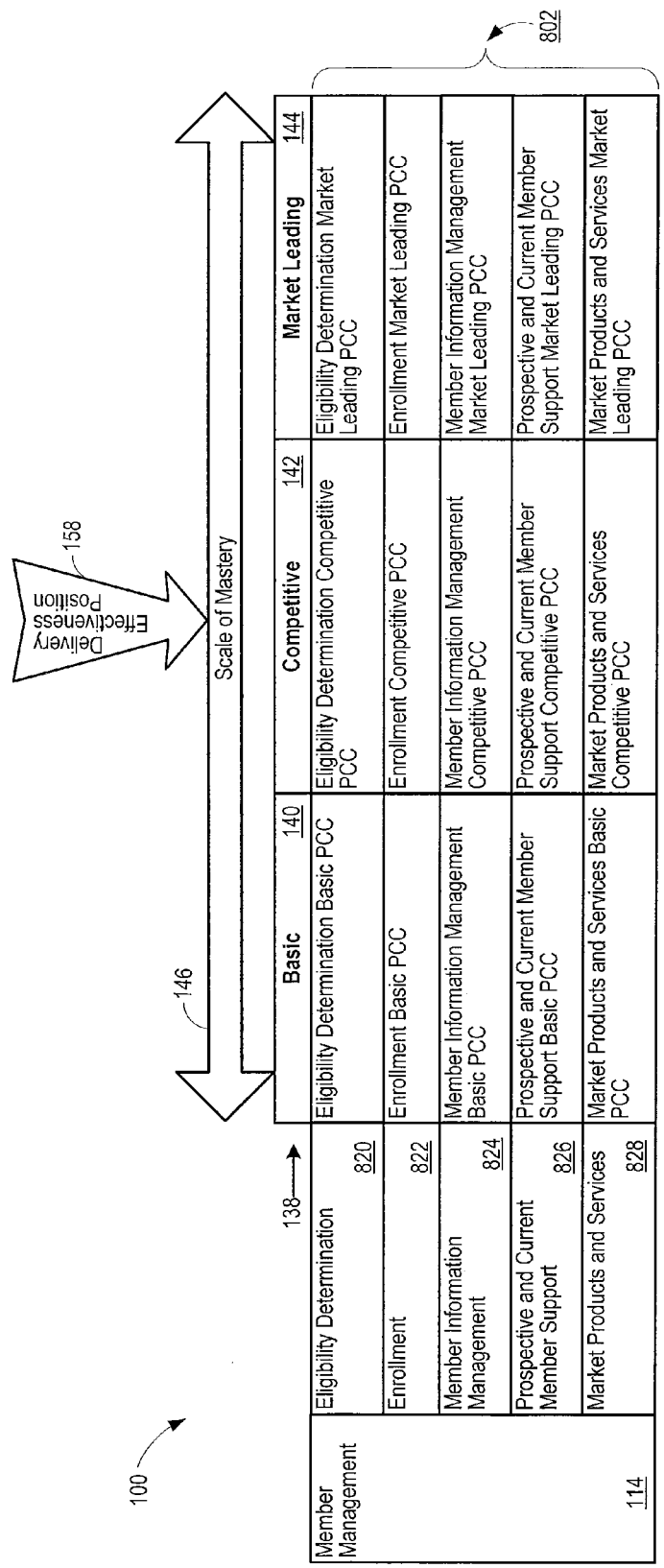
FIG. 8 shows a high-performance capability assessment model with capabilities for sub-platforms, including an eligibility determination sub-platform, an enrollment sub-platform, a member information management sub-platform, a prospective and current member support sub-platform, and a market products and services sub-platform, all corresponding to the member management platform.

FIG. 8 shows the member management platform 114 divided into respective capability areas 802. The member management platform 114 includes an eligibility determination sub-platform 820, an enrollment sub-platform 822, a member information management sub-platform 824, a prospective and current member support sub-platform 826, and a market products and services sub-platform 828.

Figure 9:
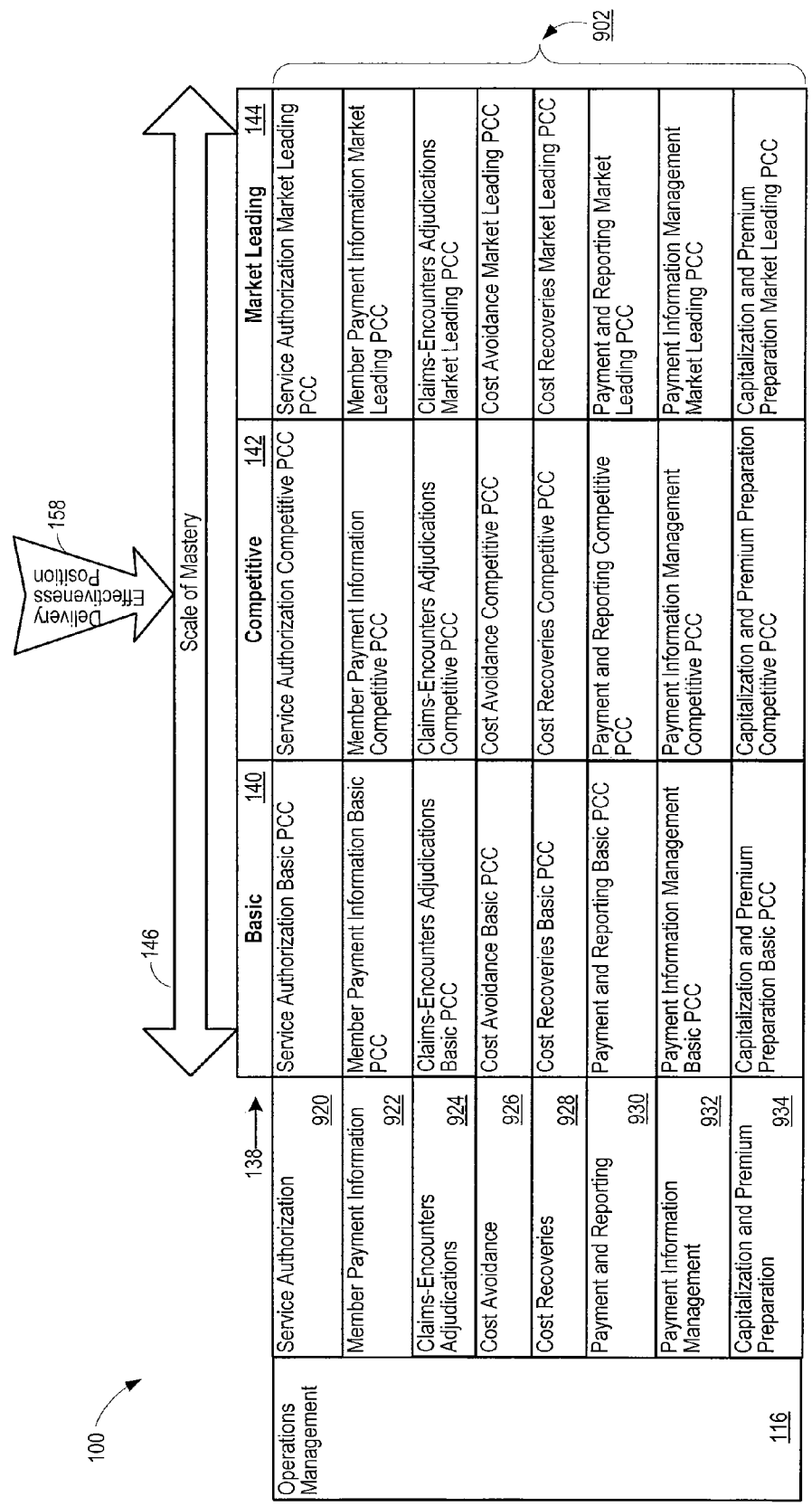
FIG. 9 shows a high-performance capability assessment model with capabilities for sub-platforms, including a service authorization sub-platform, a member payment information sub-platform, a claims-encounters adjudications sub-platform, a cost avoidance sub-platform, a cost recoveries sub-platform, a payment and reporting sub-platform, a payment information management sub-platform, and a capitation and premium preparation sub-platform, all corresponding to the operations management platform.

FIG. 9 shows the operations management platform 116 divided into respective capability areas 902. The operations management platform 116 includes a service authorization sub-platform 920, a member payment information sub-platform 922, a claims-encounters adjudications sub-platform 924, a cost avoidance sub-platform 926, a cost recoveries sub-platform 928, a payment and reporting sub-platform 930, a payment information management sub-platform 932, and a capitation and premium preparation sub-platform 934.

Figure 10:
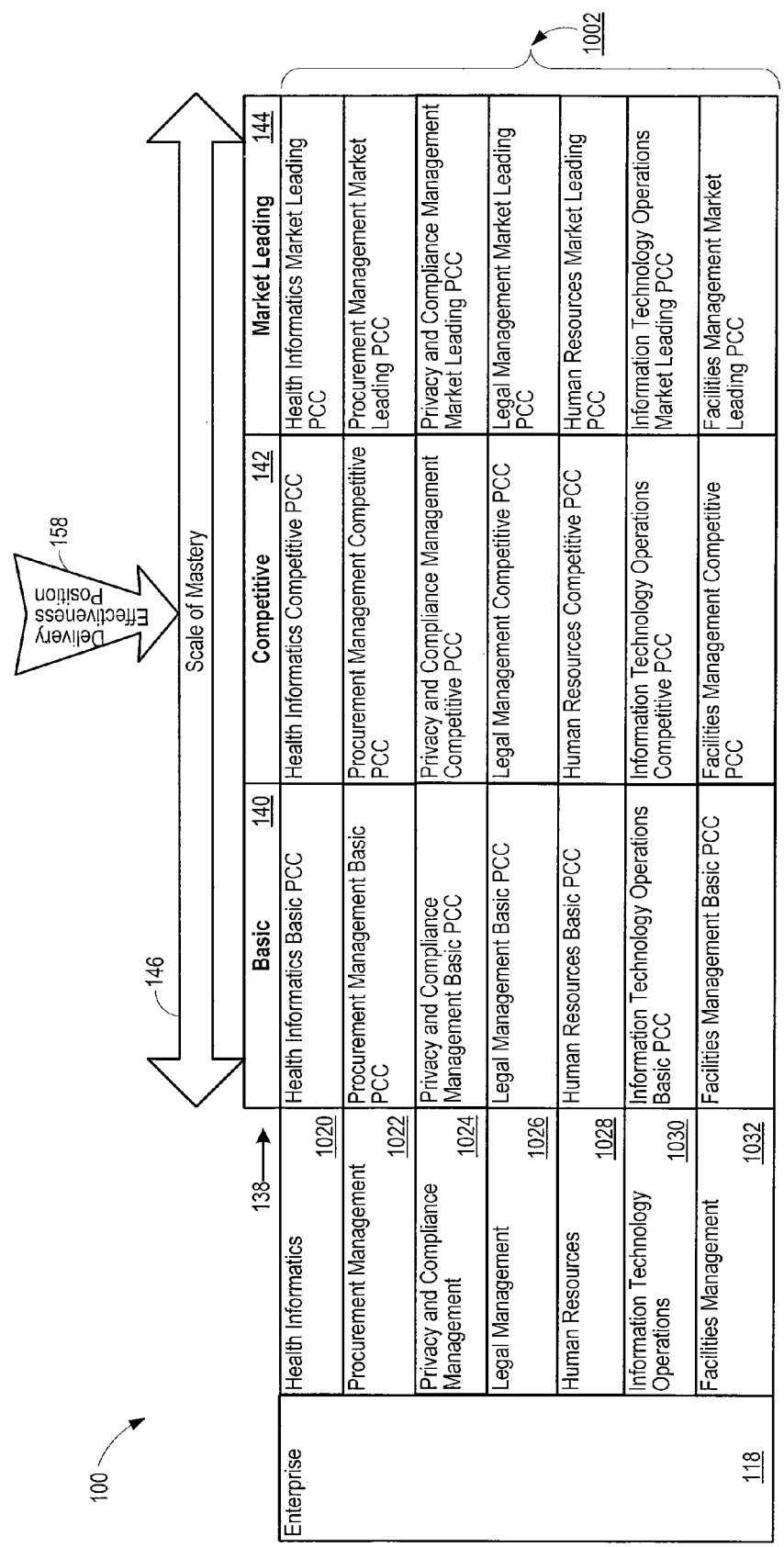
FIG. 10 shows a high-performance capability assessment model with capabilities for sub-platforms, including a health informatics sub-platform, a procurement management sub-platform, a privacy and compliance management sub-platform, a legal management sub-platform, a human resources sub-platform, an information technology operations sub-platform, and a facilities management sub-platform, all corresponding to the enterprise platform.

FIG. 10 shows the enterprise platform 118 divided into respective capability areas 1002. The enterprise platform 118 includes a health informatics sub-platform 1020, a procurement management sub-platform 1022, a privacy and compliance management sub-platform 1024, a legal management sub-platform 1026, a human resources sub-platform 1028, an information technology operations sub-platform 1030, and a facilities management sub-platform 1032.

The tables provided in the appendix immediately following the abstract, which form part of this disclosure, provide an explanation of the capabilities and corresponding key assessment areas and performance criteria for some of the capabilities within the respective sub-platforms. Each capability may include one or more key assessment areas. Each key assessment area may include one or more additional key assessment areas. In other words, a business capability may include sub-capabilities, and therefore, key assessment areas corresponding to the multiple sub-capabilities. The tables in the appendix show specific criteria used to analyze each capability.

Figure 11:
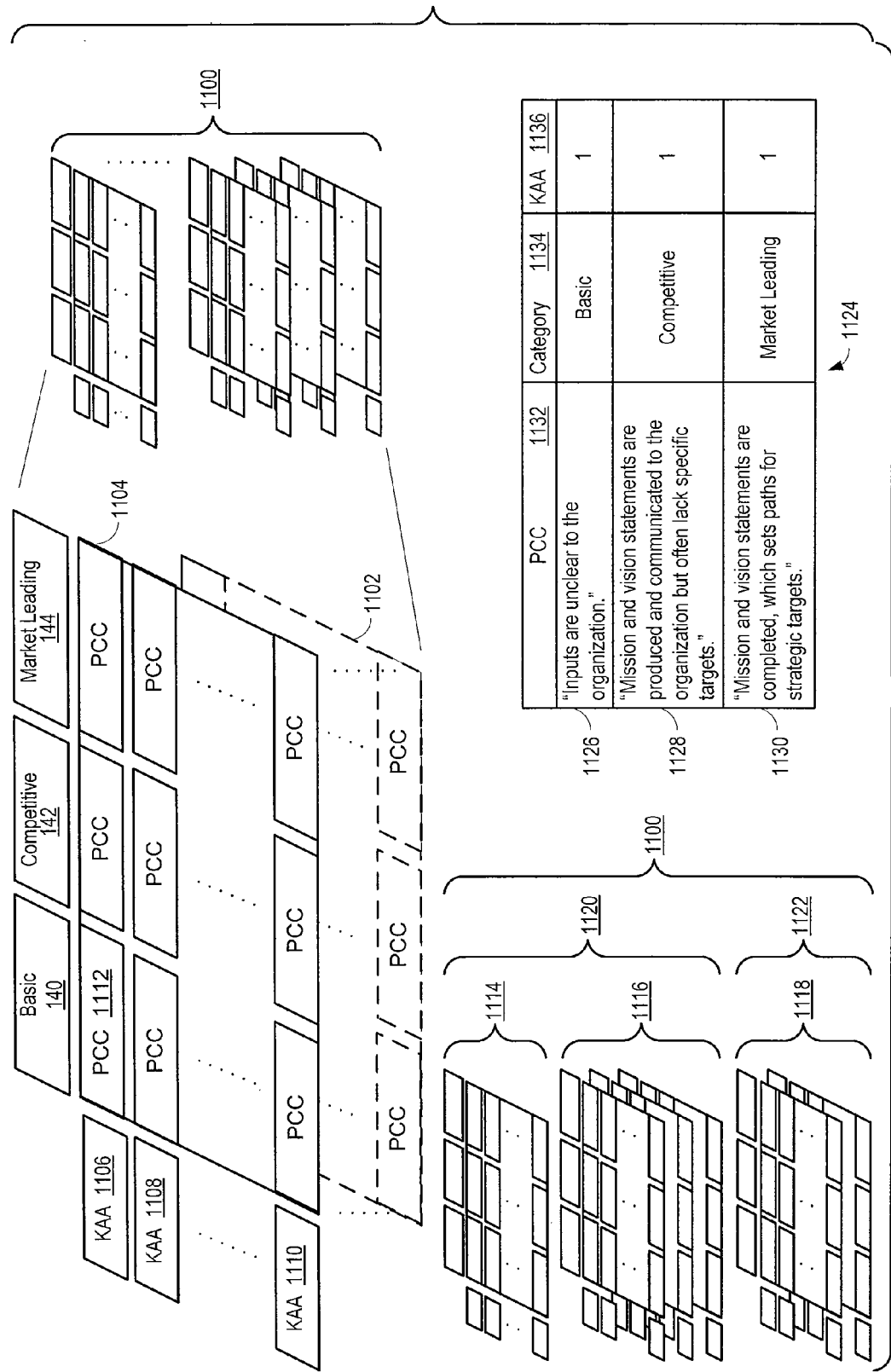
FIG. 11 shows a capability detail pool providing a multi-dimensional Medicaid program performance reference set where multiple key assessment performance reference tables are collected and stored.

FIG. 11 shows a multidimensional Medicaid program performance reference set 1100 ("reference set 1100") that provides a capability detail pool from which the system described below may obtain benchmarking tables for a Medicaid program. The reference set 1100 includes multiple key assessment performance reference tables ("reference tables"), two of which are labeled 1102 and 1104. Each reference table may provide the benchmarking criteria for a specific capability, such as those noted above with respect to FIGS. 2-10.

One dimension of each table may establish the 'Basic' performance level 140 specifying 'Basic' performance assessment criteria, the 'Competitive' performance level 142 specifying 'Competitive' performance assessment criteria, and the 'Market Leading' performance level 144 specifying 'Market Leading' performance assessment criteria. Another dimension of each table may specify one or more key assessment areas (KAAs), several of which are labeled 1106, 1108, and 1110. As noted above, performance criteria, e.g., the PCC 1112, populate each key assessment performance reference table to provide benchmark criteria for 'Basic,' 'Competitive,' and 'Market Leading' characteristics.

The reference set 1100 represents the HPCA model 100. Consistent with the HPCA model 100, the reference set 1100 may organize multiple reference tables into a hierarchical structure defining discrete changes in granularity. In one implementation, the hierarchical structure includes reference tables, high-level platforms, platforms, sub-platforms, and models. FIG. 11 labels three sub-platforms 1114, 1116, and 1118. The reference set 1100 may further organize the platforms, two of which are labeled 1120 and 1122. Platforms aggregate into the HPCA model 100 and corresponding reference set 1100. Additional, different, or fewer levels of granularity may be defined in the HPCA model 100.

The reference set 1100 may dynamically populate the reference tables with the most up-to-date performance criteria, for example upon retrieval and presentation by a business analysis consultant. The performance criteria may be retrieved from a performance capability criteria database or other information source.

FIG. 11 also shows an example of a database implementation 1124 of a portion of a reference table. In particular, the database implementation 1124 includes records (e.g., the records 1126, 1128, 1130) that establish each PCC 1112. In the example shown, each record includes a PCC field 1132, a category specifier field 1134, and a KAA specifier field 1136. Other fields may be provided, such as a reference table assignment field or reference set assignment field. The records categorize each PCC into a specific category (e.g., 'Basic'), into a specific KAA, and, optionally, into a specific reference table in a specific reference set for any particular HPCA model.

Figure 12:
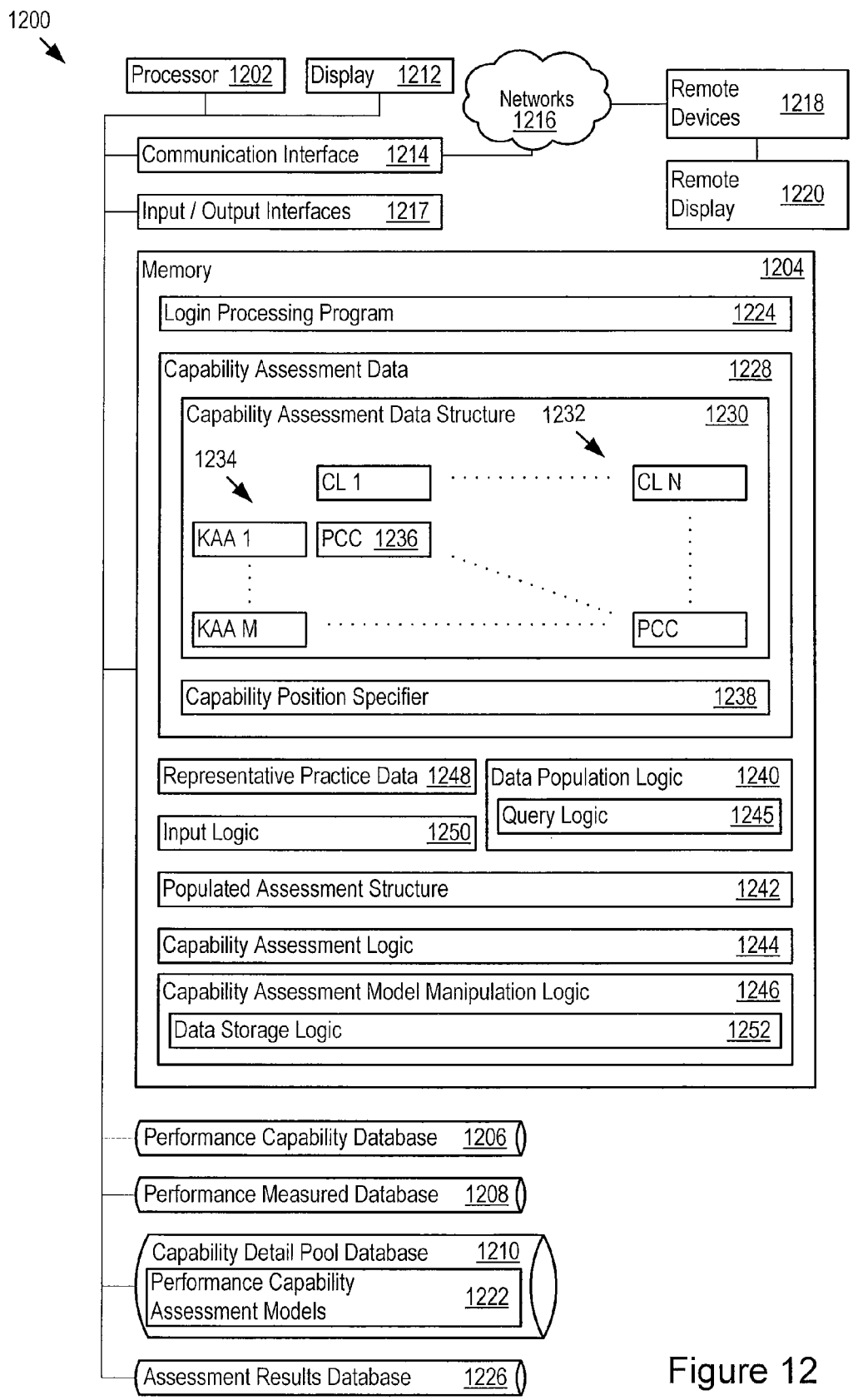
FIG. 12 shows a capability assessment system.

FIG. 12 shows a high-performance capability assessment system ("system") 1200. The system 1200 includes a processor 1202 and a memory 1204. Several databases support the operation of the system 1200, including a performance capability database 1206, a performance measured database 1208, a capability detail pool database 1210, and an assessment results database 1226. The system 1200 may include a local display 1212 and input/output interfaces 1217 (e.g., including a keyboard, mouse, microphone, speakers, or other device), and, through the communication interface 1214 and networks 1216, may communicate with remote devices 1218 and remote displays 1220. The networks 1216 may be any combination of external networks (e.g., the Internet) and internal networks (e.g., corporate LANs). The displays 1212 and 1220 may, for example, present performance capability assessment models 1222 that the system 1200 retrieves from the capability detail pool database 1210 for review, modification, and application by process engineers or other individuals. With regard to local access or access by the remote devices 1218, the system 1200 may include a login processing program 1224 to authenticate and/or authorize access to the system 1200. To that end, the login processing program 1224 may include username/password verification, private/public key encryption, or other validation and data protection capabilities.

In one implementation, the capability performance database 1206 stores performance criteria. As will be described in more detail below, the system 1200 may populate performance capability assessment models with performance capability criteria suited to any particular platform or sub-platform (e.g., a program quality management sub-platform 220) and business capability at one or more capability levels across one or more key assessment areas. The performance measured database 1208 may store the determined, measured, or otherwise ascertained characteristics, criteria, and other measured data of a particular key assessment area as representative practice data 1248. The representative practice data 1248 may be obtained through interviews with business consultants and industrial engineers, through online questionnaires, through manual or automated analysis of business data (e.g., year-end operating reports), or by other means. The capability detail pool database 1210 stores the capability detail pool 1100, which includes pre-defined performance capability assessment models 1222. The assessment results database 1226 stores determined capability levels for specific capabilities that have been analyzed.

The system 1200 facilitates the review, modification, creation, and application of performance capability assessment models. In that role, performance capability assessment model manipulation logic ("manipulation logic") 1246 within the system 1200 creates, retrieves, and stores capability assessment data 1228 in the memory 1204. The manipulation logic 1246 may establish capability assessment data 1228 in the memory 1204, including a capability assessment data structure 1230 with multiple capability levels ("CL") 1232 organized along a scale of mastery dimension, multiple key assessment areas ("KAA") 1234 organized along a key factor dimension, and performance criteria ("PCC") 1236 that populate the performance capability assessment model 1230. The manipulation logic 1246 may vary widely in implementation, and, as one example, may include data storage logic 1252 that saves data in memory and user interface logic that accepts capability level specifications, key assessment area specifications, and performance capability criteria inputs to create new performance capability assessment models, to modify existing performance capability assessment models, to delete performance capability assessment models, or to retrieve performance capability assessment models for review.

In one implementation, the manipulation logic 1246 establishes the capability assessment data structure 1230 to include a multidimensional Medicaid program performance reference set that includes multiple key assessment performance reference tables in which the key assessment performance reference tables include a 'Basic' capability performance level, a 'Competitive' capability performance level, and a 'Market Leading' capability performance level.

The capability assessment data 1228 may also include a capability position specifier 1238. The capability position specifier 1238 may record the capability level along the scale of mastery 146, as determined for any particular capability. Thus, the system 1200 may store the performance level in the assessment results database 1226 or elsewhere for future retrieval and review.

In one implementation, the data population logic 1240 may be a data population program executed by the processor 1202 that populates template performance capability assessment models. For example, the data population logic 1240 may include input logic 1250 that accepts input specifying a capability of interest that indicates a particular performance capability assessment model. The data population logic 1240 may include query logic 1245 that executes database queries and prompts a user for input to obtain the corresponding performance capability criteria for the capability of interest.

In another implementation, for example, the query logic 1245 may receive an input specifying a Medicaid program area and a Medicaid program key assessment area with the Medicaid program area for analysis. The query logic 1245 searches the multidimensional Medicaid program performance reference set for a matching key assessment performance reference table that matches the Medicaid program area and the Medicaid program key assessment area, and retrieves the matching key assessment performance reference table.

The data population logic 1240 may further include storage logic that adds the retrieved performance capability criteria to the template performance capability assessment model. The data population logic 1240 produces populated performance capability assessment structures 1242 that may be stored in the capability detail pool database 1210.

In addition to the analysis process described above, the system 1200 may provide an automated analysis of representative practice data 1248 that identifies relevant performance capability criteria and determines the position on the scale of mastery 146 of each key assessment area corresponding to the performance capability criteria for the representative practice data 1248. As one example, the system 1200 may implement capability assessment logic 1244 that includes comparison and/or matching logic that analyzes the representative practice data 1248 with respect to performance capability criteria to locate key assessment areas for which the system 1200 can determine capability levels to obtain a resultant performance level for each key assessment area.

Furthermore, the capability assessment logic 1244 may determine an overall position on the scale of mastery 146 as the capability position specifier 1238 for a capability under examination given the knowledge of where the key assessment areas corresponding to the capability under examination fall in each capability level. Thus, for example, the capability assessment logic 1244 may determine an overall capability level for a capability corresponding to the capability level for the majority of the key assessment areas, or it may apply a weighted analysis technique to give more emphasis to some key assessment areas than others in determining the overall position on the scale of mastery 146 for a capability. As another example, the capability assessment logic 1244 may implement an expert system (e.g., based on a neural network trained on prior determinations) that analyzes the determined characteristics with respect to the performance capability criteria and ascertains where the capability under examination falls along the scale of mastery 146 for each of the key assessment areas, or overall on the scale of mastery.

Figure 13:
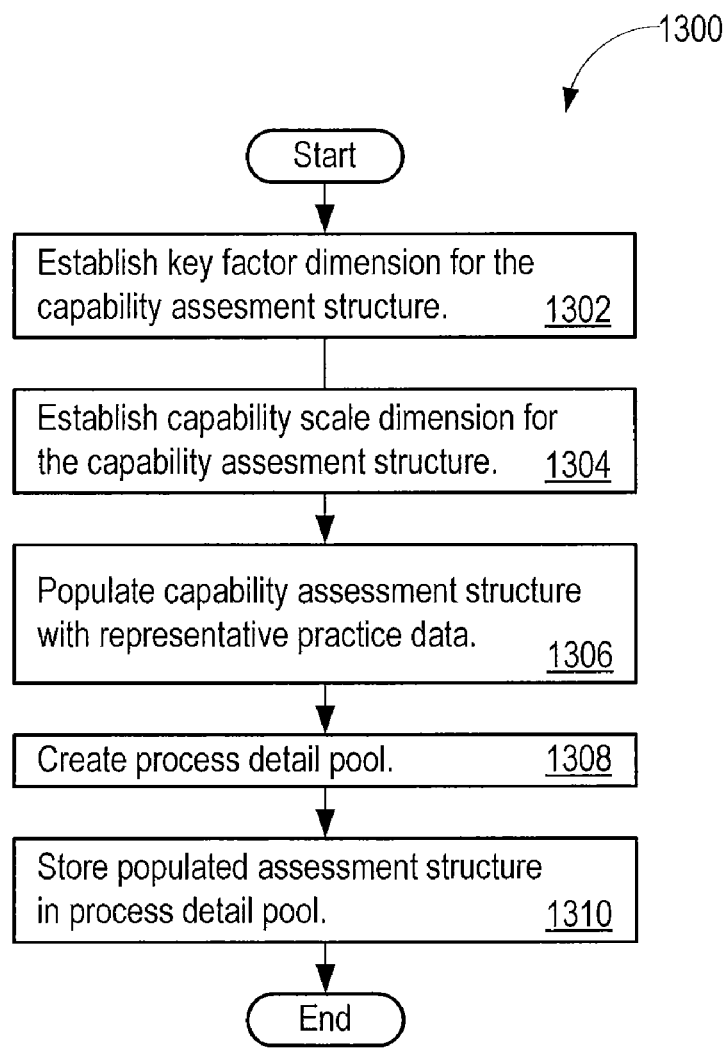
FIG. 13 shows a flow diagram for establishing high-performance capability assessment models.

FIG. 13 shows a flow diagram 1300 for creating performance capability assessment models. The performance capability assessment model creator (e.g., the manipulation logic 1246) establishes a key factor dimension for the performance capability assessment model (1302). The performance capability assessment model creator also establishes a capability scale dimension for the performance capability assessment model (1304). The capability scale dimension may define a scale of increasing organizational capability. For example, the structure creator may create the 'Basic' level 140, the 'Competitive' level 142, and the 'Market Leading' level 144. The performance capability assessment model creator also populates the performance capability assessment model with capability performance criteria (1306). A capability detail pool 1100 may be formed to hold multiple tailored key assessment performance reference tables (1308). The performance capability assessment model creator may store the populated assessment structure in the capability detail pool for subsequent retrieval and analysis (1310).

Figure 14:
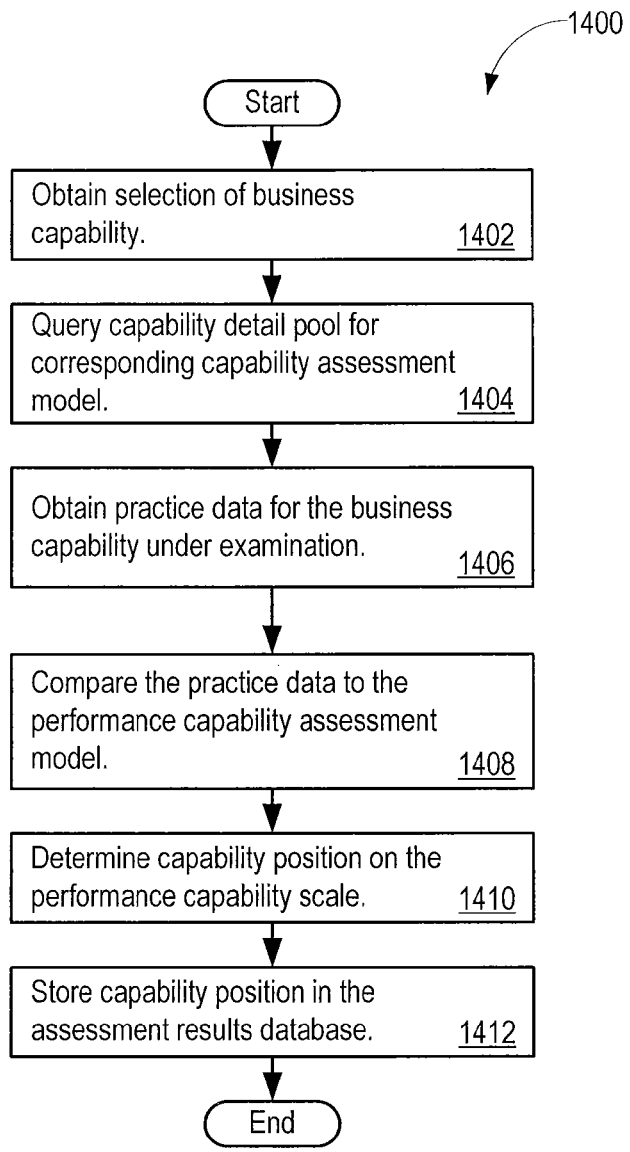
FIG. 14 shows a flow diagram for retrieving and applying high-performance capability assessment models.

FIG. 14 shows a flow diagram 1400 for retrieving and applying performance capability assessment models. A selection of a capability to be analyzed is obtained (1402). In one implementation, the system 1200 receives input data that specifies a Medicaid program area and a Medicaid program key assessment area for analysis. For example, the system 1200 may accept input from a business consultant that specifies a capability for analysis. The system 1200 may query the capability detail pool 1100 for a corresponding performance capability assessment model (1404). The corresponding performance capability assessment model may be pre-defined in the capability detail pool 1100, or the data population logic 1240 (or other actor) may populate a performance capability assessment model template that the system 1200 newly creates, or that the system 1200 retrieves from a data store, such as the capability detail pool database 1210.

In another example, the system 1200 searches the multidimensional Medicaid program performance reference set in the capability detail pool 1100 for a matching key assessment performance reference table based on the input data that specifies a Medicaid program platform and a Medicaid program key assessment area. The system 1200 retrieves the matching key assessment performance reference table and initiates analysis of the matching key assessment performance reference table to obtain a resultant performance level for the Medicaid program key assessment area.

The system 1200 obtains representative practice data 1248 for the capability under examination in the specific business under review (1406). For example, a business consultant may interview the business to determine how the business currently executes the capability under review. As another example, a representative from the business may complete a questionnaire, submit business data for analysis and parameter extraction, or otherwise provide the characteristics of their current capability execution. As a further example, the system 1200 may retrieve the representative practice data 1248 from a database of previously obtained representative practice data.

The system 1200 compares the representative practice data 1248 to the performance criteria in the performance capability assessment model (1408). For example, a business consultant may use his or her expertise to determine the level for the business and the capability under examination (1410). Alternatively or additionally, the capability assessment logic 1244 may perform an automated analysis of the assessment results data in the assessment results database 1226 and ascertain the performance level on the scale of mastery 146. The system 1200 may store the assessment results, including the determined performance level, for future reference in the assessment results database 1226 or other location (1412).

Figure 15:
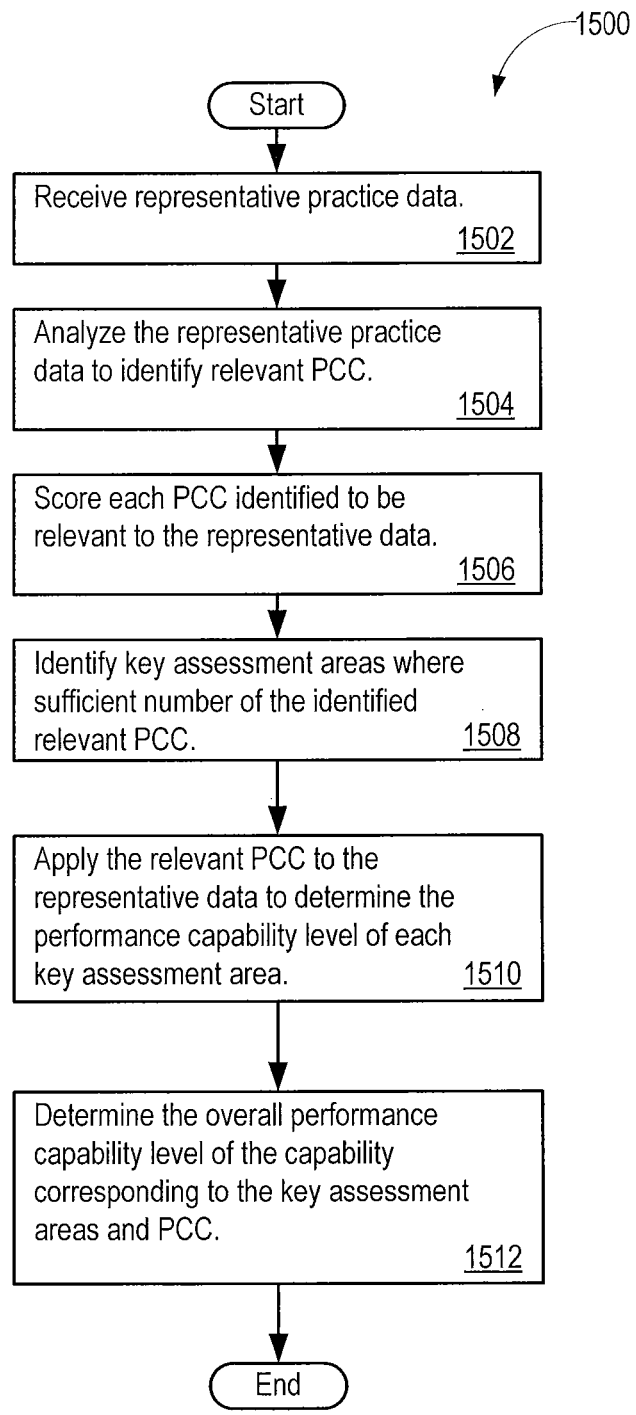
FIG. 15 shows a flow diagram for analyzing representative practice data to determine a Medicaid program and Medicaid key assessment area to which the representative practice data applies.

FIG. 15 shows a flow diagram 1500 for analyzing representative practice data 1248 to determine a Medicaid program and a Medicaid program assessment area to which the representative practice data applies. The system 1200 receives representative practice data 1248 as input data (1502). The system 1200 may receive the representative practice data 1248 from a database query performed by the query logic 1245 that the query logic executes periodically, when instructed by an operator, and/or automatically against any number of available database sources that store representative practice data 1248. The capability assessment logic 1244 analyzes the representative practice data 1248 to identify performance capability criteria in the capability detail pool 1100 that the capability assessment logic 1244 determines relevant to the representative practice data 1248 (1504). For example, the capability assessment logic 1244 may compare and/or match the content of the representative practice data 1248 with the performance capability criteria by using natural language processing (NLP), text string, and/or substring matching, by comparing tags linked to the representative practice data 1248 and that specify that any portion of the representative practice data 1248 is applicable to a specific PCC, by querying for a manual classification of the representative practice data 1248 to a PCC, or by using other matching techniques. The capability assessment logic 1244 may score and/or weight a performance capability criteria and compare the score and/or weight to a user specified relevance threshold to rank the relevance of the performance capability criteria to the representative practice data 1248 (1506). The user may specify particular terms and/or phrases to search and match between the performance capability criteria and the representative practice data 1248, in order to score the performance capability criteria.

The capability assessment logic 1244 may determine, based on the number of performance capability criteria that meet or exceed the relevance threshold, that the capability assessment logic 1244 has identified a sufficient number of performance capability criteria for a specific key assessment area in order to determine a performance level for the capability as a whole or any key assessment area within the capability (1508). As one example, where at least 51% of the performance capability criteria for a particular key assessment area meet or exceed the relevance threshold, the capability assessment logic 1244 applies the performance capability criteria to the representative practice data 1248. In another example, the performance capability criteria for a particular key assessment area may be ranked in importance and/or designated as mandatory in order to assess the key assessment area. In the event the capability assessment logic 1244 identifies the mandatory performance capability criteria for a key assessment area, the capability assessment logic 1244 applies the performance capability criteria to the representative practice data 1248.

The capability assessment logic 1244 may apply the performance capability criteria meeting or exceeding the relevance threshold to the representative practice data 1248 to determine whether any particular PCC is met. Accordingly, as the capability assessment logic 1244 analyzes the PCC, the system 1200 tracks the best fit of the representative practice data 1248 to the PCCs in the key assessment performance reference tables. In other words, the system 1200 determines how the representative practice data 1248 meets (or does not meet) each PCC, thereby gaining insight into whether the representative practice data 1248 is indicative of 'Basic,' 'Competitive,' or 'Market Leading' practices.

The system 1200 may also gauge the position on the scale of mastery 146 of each key assessment area corresponding to the performance capability criteria (1510). The capability assessment logic 1244 may further determine an overall position on the scale of mastery 146 for a capability (1512). The capability assessment logic 1244 may establish that a desired number and/or designated mandatory performance capability criteria for the key assessment areas have been identified as relevant to a capability and sufficient to determine the position on the scale of mastery 146 for the capability. For example, the capability assessment logic 1244 may determine an overall performance level for the capability based on the performance level determined for the majority of the key assessment areas. The capability assessment logic 1244 may apply a weighted analysis technique to give more emphasis to some key assessment areas than others in determining the overall position on the scale of mastery 146 for the capability. Although selected aspects, features, or components of the implementations are depicted as being stored in computer-readable memories (e.g., as computer-executable instructions or performance capability assessment models), all or part of the systems and structures may be stored on, distributed across, or read from other computer-readable media. The computer-readable media may include, for example, secondary storage devices such as hard disks, floppy disks, and CD-ROMs; a signal, such as a signal received from a network or received at an antenna; or other forms of memory, including ROM or RAM, either currently known or later developed.

Various implementations of the system 1200 may include additional or different components. A processor may be implemented as a microprocessor, a microcontroller, a DSP, an application specific integrated circuit (ASIC), discrete logic, or a combination of other types of circuits or logic. Similarly, memories may be DRAM, SRAM, Flash, or any other type of memory. The processing capability of the system may be distributed among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many ways, including data structures such as linked lists, hash tables, or implicit storage mechanisms. Programs may be combined or split among multiple programs, or distributed across several memories and processors.

The logic, circuitry, and processing described above may be encoded or stored in a machine-readable or computer-readable medium such as a compact disc read only memory (CDROM), magnetic or optical disk, flash memory, random access memory (RAM) or read only memory (ROM), erasable programmable read only memory (EPROM) or other machine-readable medium such as, for example, instructions for execution by a processor, controller, or other processing device.

The medium may be implemented as any device that contains, stores, communicates, propagates, or transports executable instructions for use by or in connection with an instruction executable system, apparatus, or device. Alternatively or additionally, the logic may be implemented as analog or digital logic using hardware, such as one or more integrated circuits, or one or more processors executing instructions; or in software in an application programming interface (API) or in a Dynamic Link Library (DLL), functions available in a shared memory or defined as local or remote procedure cells; or as a combination of hardware and software.

In other implementations, the logic may be represented in a signal or a propagated-signal medium. For example, the instructions that implement the logic of any given program may take the form of an electronic, magnetic, optical, electromagnetic, infrared, or other type of signal. The systems described above may receive such a signal at a communication interface, such as an optical fiber interface, antenna, or other analog or digital signal interface, recover the instructions from the signal, store them in a machine-readable memory, and/or execute them with a processor.

The systems may include additional or different logic and may be implemented in many different ways. A processor may be implemented as a controller, microprocessor, microcontroller, application specific integrated circuit (ASIC), discrete logic, or a combination of other types of circuits or logic. Similarly, memories may be DRAM, SRAM, Flash, or other types of memory. Parameters (e.g., conditions and thresholds) and other data structures may be separately stored and managed, may be incorporated into a single memory or database, or may be logically and physically organized in many different ways. Programs and instructions may be parts of a single program, separate programs, or distributed across several memories and processors.

The HPCA 100 model provides unexpectedly good results for a performance capability assessment model, particularly in the Medicaid program area. In particular, the combinations of key assessment areas and particular assessment criteria of the HPCA model, including the criteria noted in the Appendix of Tables, provide significant advantages over other assessment models. The unexpectedly good results include clearly identifying and delineating from among multiple related complex processes the specific processes to improve, how to improve the process, and identifying concrete and measurable improvement goals.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

TABLE 1

Global Health and Life Sciences High Performance
Capability Assessment Model-Public Health Services-Medicaid Program Management

| Sub-Platform: Program Quality Management | Capability: Manage Business Performance | |
|---|---|---|
| Basic | Competitive | Market Leading |

1.5.3.1 Manage Productivity, Capacity & Cost
1.5.3.2 Manage Knowledge, Processes & Best Practices
1.5.3.3 Manage Service Quality

TABLE 2

Global Health and Life Sciences High Performance
Capability Assessment Model-Public Health Services-Medicaid Program Management

| Sub-Platform: Program Quality Management | Capability: Manage Quality, Risk, and Performance | |
|---|---|---|
| Basic | Competitive | Market Leading |

1.5.4.1 Define Approach and Program
1.5.4.2 Establish Metrics and Indicators
1.5.4.3 Collect and Analyze Information
1.5.4.4 Provide Feedback and Change Practices as Appropriate

TABLE 3

Global Health and Life Sciences High Performance
Capability Assessment Model-Public Health Services-Medicaid Program Management

| Sub-Platform: Cost Containment | Capability: Perform Cost Containment Functions | |
|---|---|---|
| Basic | Competetive | Market Leading |

1.9.1.1 Perform ongoing research and analysis to identify possible areas for cost containment.
1.9.1.2 Identify methods to reduce program administrative at health care costs
1.9.1.3 Review options, estimate of benefits, impact assessments, and alternatives
1.9.1.4 Prioritize initiatives
1.9.1.5 Implement approved cost reduction initiatives
1.9.1.6 Determine measurement methodology and benchmarks.
1.9.1.7 Continually measure and analyze cost reduction measures.
1.9.1.8 Provide reports on effectiveness of cost reduction measures

TABLE 4

Global Health and Life Sciences High Performance
Capability Assessment Model-Public Health Services-Medicaid Program Management

| Sub-Platform: Program Administration | | Capability: Develop Agency Goals and Initiatives |
| --- | --- | --- |
| Basic | Competitive | Market Leading |
| Agency receives notices that a review of current goals and objectives is warranted. Basic review of Agency Goals and Objectives takes place. Consensus on changes is established with stakeholders. Publish new statement of goals and objectives is published. | More in depth review of Agency Goals and Objectives takes place. Consensus on changes is established with stakeholders Publish new statement of goals and objectives is published, including electronic forms of publication. | Basic review of Agency Goals and Objectives takes place Consensus on changes is established with stakeholders Publish new statement of goals and objectives is published |

TABLE 5

Global Health and Life Sciences High Performance
Capability Assessment Model-Public Health Services-Medicaid Program Management

| Sub-Platform: Program Administration | | Capability: Develop and Maintain Program Policy |
| --- | --- | --- |
| Basic | Competetive | Market Leading |
| Requests to add, delete, or change policy are handled through a manual process. Research staff are required to analyze policy and assess the impact of policy on budget, stakeholders, and other benefits. Public hearings are held to explain existing policy and policy changes. | Requests to add, delete, or change policy are handed through a combination of manual/automated processes. Few research staff are required to analyze policy and assess the impact of policy on budget, stakeholders, and other benefits. | Basic review of Agency Goals and Objectives takes place Consensus on changes is established with stakeholders Publish new statement of goals and objectives is published |

TABLE 6

Global Health and Life Sciences High Performance
Capability Assessment Model-Public Health Services-Medicaid Program Management

| Sub-Platform: Program Administration | | Capability: Maintain State Plan |
| --- | --- | --- |
| Basic | Competitive | Market Leading |
| Notifications to review and update the state plan are sent manually. Additional staff is required to review the current state plan, analyze changes to the state plan, and research and assess impact of state plan changes. | Notifications to review and update the state plan are sent through an automated process. Fewer staff is required to review the current stateplan, analyze changes to the state plan, and research and assess impact of state plan changes. | Even fewer staff is required to review the current state plan, analyze changes to the state plan, and research and assess impact of state plan changes. |

TABLE 7

Global Health and Life Sciences High Performance
Capability Assessment Model-Public Health Services-Medicaid Program Management

| Sub-Platform: Program Administration | | Capability: Perform Organizational Planning |
| --- | --- | --- |
| Basic | Competitive | Market Leading |
| 1.2.6.1 Conduct Environmental Analysis 1.2.6.2 Develop Strategic Plan 1.2.6.3 Develop Business and Tactical Plans 1.2.6.4 Develop Implementation Plans | | |

TABLE 8

Global Health and Life Sciences High Performance
Capability Assessment Model-Public Health Services-Medicaid Program Management

| Sub-Platform: Program Administration | | Capability: Market the Organization |
| --- | --- | --- |
| Basic | Competitive | Market Leading |
| 1.2.1.1 Develop Marketing Plan 1.2.1.2 Develop Collateral Materials 1.2.1.3 Conduct Advertising | | |

TABLE 8-continued

Global Health and Life Sciences High Performance
Capability Assessment Model-Public Health Services-Medicaid 1.2.1.4 Conduct Public Relations
1.2.1.5 Manage Quality and
Performance of the Marketing Process

TABLE 9

Global Health and Life Sciences High Performance
Capability Assessment Model-Public Health Services-Medicaid Program Management

| Sub-Platform: Program Administration | Capability: Provide Governance | |
|---|---|---|
| Basic | Competitive | Market Leading |
| 1.2.5.1 Establish Mission, Value, and Direction | | |
| 1.2.5.2 Develop and Operate the Governance Infrastructure | | |
| 1.2.5.3 Formulate and Approve Organization Policies | | |
| 1.2.5.4 Provide Oversight | | |
| 1.2.5.5 Select and Evaluate Executive Management | | |
| 1.2.5.6 Represent the Organization | | |

TABLE 10

Global Health and Life Sciences High Performance
Capability Assessment Model -
Public Health Services - Medicaid Program Management

| Sub-Platform: Budget | Capability: Formulate Budget | |
|---|---|---|
| Basic | Competitive | Market Leading |
| Review of current budget takes place | | |
| 1.3.1.2 Research and request information regarding revenue, costs, and benefits | | |
| 1.3.1.3 Develop and discuss budget scenarios with stakeholders | | |
| 1.3.1.4 Create, review, and approve new budget | | |

TABLE 11

Global Health and Life Sciences High Performance
Capability Assessment Model -
Public Health Services - Medicaid Program Management

| Sub-Platform: Budget | Capability: Manage F-MAP | |
|---|---|---|
| Basic | Competitve | Market Leading |
| 1.3.3.1 Receive and review notification | | |
| 1.3.3.2 Request, review, and analyze F-MAP, FFP, and applicable laws | | |
| 1.3.3.3 Propose and submit change in approach to calculating F-MAP, FFP | | |
| 1.3.3.4 Develop guidelines for change and implementation plan | | |
| 1.3.3.5 Develop algorithms | | |
| 1.3.3.6 Publish newFFP rules | | |

TABLE 12

Global Health and Life Sciences High Performance
Capability Assessment Model - Public Health Services - Medicaid Program Management

| Sub-Platform: Budget | | Capability: Manage FFP for MMIS |
|---|---|---|
| Basic | Competitve | Market Leading |
| The Manage Federal Financial Participation business process is likely primarily paper/phone/fax based processing and some proprietary EDI. Timeliness of responses to inquiries and data reporting is indeterminate. | The Manage Federal Financial Participation business process increases its use of electronic interchange and automated processes. Agencies centralize common processes and are run as enterprises with "cost centers" responsible for meeting performance benchmarks. The agency has central point for developing customer communications. Communications to customers are consistent, timely and appropriate. Improves on previous level capability plus by: Point-to-point or, wrapped connectivity to client- Point-to-point interfaces segregated by interface type Improves on previous level capability plus by. | Improves on previous level capability plus: Virtual access to administrative and clinical records Increased use of clinical data Improves on previous level capability plus: Focused data - data of record Self adjusting business rules Improves on previous level capability plus: Use of clinical data to increase the accuracy of processes Clinical staff focuses on exception cases Improves on previous level capability plus: Point-to-point collaboration Content sensitive business logic |

TABLE 12-continued

Global Health and Life Sciences High Performance
Capability Assessment Model - Public Health Services - Medicaid

| | | |
|---|---|---|
| | Enhanced consistent timing for response to primary client | Improves on previous level capability plus: Business Process Management |
| | Different interfaces with different data format and semantics | Metadata - Shared nationally Improves on previous level capability plus: |
| | Improves on previous level capability plus by: Transactions are received and responded to via EDI, Web Portal | Full interoperability other local, state, and federal programs to provide complete virtual patient clinical record and administrative data |
| | Business areas are structured functionally and not by program/product line. | A business process collaborates with other processes in a peer2peer environment, eliminating |
| | Data is standardized for automated electronic interchanges (interfaces) | redundant collection and interchange of data, and improving realtime, multi-axial processing. |
| | The Agency supports data and technology integration end interoperability. | Members empowered to make own treatment decisions. |
| | Customers are able to access the information required regardless of their entry point into the enterprise. | Most services instantly authorized or denied from point of service; payment automaticallly established without need of invoice. |

TABLE 13

Global Health and Life Sciences High Performance
Capability Assessment Model - Public Health Services - Medicaid Program Management

| Sub-Platform: Budget | | Capability: Manage State Funds |
|---|---|---|
| Basic | Competitive | Market Leading |
| A business process is likely primarily paper/phone/fax based processing and some proprietary EDI. Programs are siloed so uncoordinated
Non-standerdized data makes any type of cross program performance monitoring, management reporting, fraud detection, or reporting and analysis difficult and costly.
Customers have difficulty accessing consistent, quality, or complete information about programs, eligibility, services or providers
Communications are often not linguistically, culturally or competency appropriate and socio-economic barriers to accessing information and health care.
Programs create inconsistent rules across the Agency and apply their own rules inconsistently.
Indeterminate connectivity to client
Programs create inconsistent rules across the Agency and apply their own rules inconsistently.
Programs create inconsistent rules across the Agency and apply their own rules inconsistently.
Inconsistent timing for response to primary client
Programs create inconsistent rules across the Agency and apply their own rules inconsistently.
Multiple data formats and semantics
Programs create inconsistent rules across the Agency and apply their own rules inconsistently.
External inputs & outputs are received/sent manually via paper, telephone, & fax
Transactions are individually reviewed using inconsistent interpretation of guidelines responded to via paper, USPS or fax. | The Manage Federal Financial Participation business process increases its use of electronic interchange and automated processes
Agencies centralize common processes and are run as enterprises with "cost centers" responsible for meeting performance benchmarks
The agency has central point for developing customer communications. Communications to customers are consistent, timely and appropriate.
Improves on previous level capability plus by: Point-to-point or wrapped connectivity to client
Improves on previous level capability pus by: Point-to-point interfaces segregated by interface type
Improves on previous level capability plus by: Enhanced consistent timing for responses to primary client
Improves on previous level capability plus by: Different interfaces with different data format and semantics
Improves on previous level capability plus by: Transactions are received and responded to via EDI, Web Portal
Business areas are structured functionally and not by program/product line.
Data is standardized for automated electronic interchanges (interfaces)
The Agency supports data and technology integration and interoperability
Customers are able to access the information required regardless of their entry point into the enterprise. | Improves on previous level capability plus: Virtual access to administrative and clinical records
Improves on previous level capability plus: Increased use of clinical data
Improves on previous level capability plus: Focused data - data of record
Improves on previous level capability plus: Self-adjusting business rules
Improves on previous level capability plus: Use of clinical data to increase the accuracy, of processes
Improves on previous level capability plus: Clinical staff focuses on exception cases
Improves on previous level capability plus: Point-to-point collaboration
Improves on previous level capability plus: Content sensitive business logic
Improves on previous level capability plus: Business Process Management
Improves on previous level capability plus: Metadata - Shared nationally
Improves on previous level capability plus: Full interoperability with other local, state, and federal programs to provide complete virtual patient clinical record and administrative data
Improves on previous level capability plus: Access to national clinical guidelines
A business process collaborates with other processes in a peer2peer enviroment, eliminating redundant collection and interchange of data, and improving realtime multi-axial processing.
. . .
Members empowered to make own treatment decisions
Most services instantly authorized or denied from point of service; payment automatically established without need of invoice. |

TABLE 14

Global Health and Life Sciences High Performance
Capability Assessment Model -
Public Health Services - Medicaid Program Management

| Sub-Platform: Risk and Issue Management | Capability: Manage Business Change |
|---|---|

Basic 1.7.1.1 Identify Business Case for Change
1.7.1.2 Assess Alignment with Strategic Direction
1.7.1.3 Define Change Program
1.7.1.4 Manage H/R Components of Transformation
Staff and Manage Transformation Team
Plan H/R Needs for Transformed Organization
Manage Transformation Communications
Manage Transformation Training
Align Culture

TABLE 15

Global Health and Life Sciences High Performance
Capability Assessment Model - Public Health Services - Medicaid Program Management

| Sub-Platform: Policy Management | Capability: Capability: React to Changes in Law |
|---|---|

Basic 1.8.1.1 Review the Medicaid Plan amendment from the State as a result of a change in law
1.8.1.2. Assess impact of changes to the Medicaid program
Cost cut the changes
Identify the areas impacted
1.8.1.3 Submit impact of changes to CMS for approval

TABLE 16

Global Health and Life Sciences High Performance
Capability Assessment Model -
Public Health Services - Medicaid Program Management

| Sub-Platform: Policy Management | Capability: Receive State and Federal Legislative Inquiries |
|---|---|

Basic 1.8.4.1 Capture types of inqiiries
1.8.4.2 Assess the inquiries/complaints for management to focus on

TABLE 17

Global Health and Life Sciences High Performance
Capability Assessment Model -
Public Health Services - Medicaid Program Management

| Sub-Platform: Policy Management | Capability: Respond to CMS and GAO Audits |
|---|---|

Basic 1.8.3.1 Indicate agreement/disagreement with the findings
1.8.3.2 Indicate agreement/disagreement with CMS/GAO recommendations and monetary amounts, including costs questioned and other estimates
1.8.3.3 Identify target dates for completion of final action on recommendations with which management agrees.
1.8.3.4 Indicate agreement/disagreement with findings of reportable material weakness.

TABLE 18

Global Health and Life Sciences High Performance
Capability Assessment Model -
Public Health Services - Medicaid Program Management

| Sub-Platform: Policy Management | Capability: Work with the Office of Government Affairs |
|---|---|

Basic 1.8.2.1 Identify program impact and record it
1.8.2.2 Identify policy impact and record it

TABLE 19

Global Health and Life Sciences High Performance
Capability Assessment Model - Public Health Services - Medicaid Program Management

| Sub-Platform: Program Information | | Capability: Generate Financial and Program Analysis Report |
|---|---|---|
| Basic | Competitive | Market Leading |
| The Generate Financial & Program Analysis Reports business process is likely done with a mix of tape, CD and some proprietary EDI. | The business process increases its use of electronic interchange and automated processes. Agencies are run as enterprises | The business process interfaces with other processes via federated architectures or collaborates with other processes in a |

TABLE 19-continued

Global Health and Life Sciences High Performance
Capability Assessment Model - Public Health Services - Medicaid

| | | |
|---|---|---|
| Programs are siloed so uniformity of data is uncoordinated and non-standardized data makes any type of cross program performance monitoring, management reporting, fraud detection, or reporting and analysis difficult and costly. | with "cost centers" responsible for meeting performance benchmarks.<br>Programs are agile and able to adjust their rules quickly when business activity monitoring indicates that the rules are no longer yielding desired benchmarks<br>Agencies centralize and standardize data to increase its usefulness for performance monitoring, management reporting, fraud detection, and reporting and analysis.<br>Business areas are structured functionaly and not by program/product line with infrastructure architected to support this design.<br>Data is standardized for automated electronic interchanges (interfaces) Agency supports data and technology integration and interoperability. | peer2peer environment, eliminating redundant collection and interchange of data, and improving realtime, multi-axial processing |

TABLE 20

Global Health and Life Sciences High Performance
Capability Assessment Model - Public Health Services - Medicaid Program Management

| Sub-Platform:<br>Program Information | | Capability: Maintain Benefit/<br>Reference Information |
|---|---|---|
| Basic | Competitive | Market Leading |
| A business process is likely primarily paper/phone/fax based processing and some proprietary EDI. Programs are siloed so uncoordinated.<br>Non-standardized data makes any type of cross program performance monitoring, management reporting, fraud detection, or reporting and analysis difficult and costly.<br>Clinical data is rarely the basis for decisions, and requires accessing paper medical records. Most data is administrative use of encounter data. Timeliness of responses to inquiries and data reporting is indeterminate.<br>Customers have difficulty accessing consistent, quality, or complete information about programs, eligibility, services or providers.<br>Communications are often not linguistically, culturally or competency appropriate and socio-economic barriers to accessing information and health care. Programs create inconsistent rules across the Agency and apply their own rules inconsistently. | A business process increases its use of electronic interchange and automated processes. Agencies centralize common processes and are run as enterprises with "cost centers" responsible for meeting performance benchmarks.<br>Centralization increases consistency of communications. Agency business relationships are increasingly hub and spoke vs. point to point with each internal and external party.<br>These changes improve customers ability to reliably access the information and services they require.<br>Business areas are structured functionally and not by program/product line with infrastructure architected to support this design.<br>Data is standardized for automated electronic interchanges (interfaces) that are oblivious to whether the sender or receiver is internal or external, applying appropriate levels of security to each request/receiver.<br>. . .<br>The Agency supports data and technology integration and interoperability. | A business process interfaces with other processes via federated architectures or collaborates with other processes in a peer2peer environment, eliminating redundant collection and interchange of data, and improving realtime, multi-axial processing |

TABLE 21

Global Health and Life Sciences High Performance
Capability Assessment Model - Public Health Services - Medicaid Program Management

| Sub-Platform:<br>Program Information | | Capability: Manage<br>Program Information |
|---|---|---|
| Basic | Competitive | Market Leading |
| Data from enterprise information registries or repositories is available to load<br>Records are processed manually, but the | Records are processed using both manual and automated processes, making the data easier to access. | Records are sent through a fully automated process.<br>Even more sophisticated reporting, analysis, |

TABLE 21-continued

Global Health and Life Sciences High Performance
Capability Assessment Model - Public Health Services - Medicaid

| | | |
|---|---|---|
| data is not made easily available. Basic reporting, analysis, and decision support capabilities are available. Agency possesses record retention requirements. | More sophisticated reporting, analysis, and decision support capabilities are available. Data is archived in accordance with state record retention requirements. | and decision support capabilities are available. Data is archived in accordance with state and federal record retention requirements. |

TABLE 22

Global Health and Life Sciences High Performance
Capability Assessment Model - Public Health Services - Medicaid Program Management

| Sub-Platform: Accounting | | Capability: Manage 1099s |
|---|---|---|
| Basic | Competitive | Market Leading |
| The Manage 1099s business process is likely primarily paper/phone/fax based processing and some proprietary EDI. Programs are siloed and multiple 1099s may be created by different payment systems. Timeliness of responses to inquiries and data reporting is indeterminate. | The business process is increasing its use of electronic interchange and automated processes. Agencies are completely centralized. Data is standardized for automated electronic interchanges (interfaces). Agencies are centralizing common processes to achieve economies of scale and increase coordination. The Agency supports data and technology integration and interoperability. Centralization increases consistency of communications. Agency business relationships are increasingly hub and spoke vs. point to point with each internal and external party. The Agency actively supports and enables its customers to access information electronically. | The business process interfaces with other processes via federated architectures or collaborates with other processes in a peer2peer environment, eliminating redundant collection and interchange of data, and improving realtime, multi-axial processing |

TABLE 23

Global Health and Life Sciences High Performance
Capability Assessment Model -
Public Health Services - Medicaid Program Management

| Sub-Platform: Accounting | Capability: Perform Accounting Functions |
|---|---|
| Basic | |
| 1.4.2.1 Continuity Planning 1.4.2.2 General Ledger (includes Accounts Payable and Receivable) 1.4.2.3 Reporting 1.4.2.4 Account Maintenance | |

TABLE 24

Global Health and Life Sciences High Performance
Capability Assessment Model - Public Health Services - Medicaid Program Management - Develop and Maintain Medical and Network Policies

| Sub-Platform: Benefits Administration | | Capability: Designate Approved Service/Drug Formulary |
|---|---|---|
| Basic | Competitive | Market Leading |
| The Designate Approved Services/Drug Formulary process is primarily a manuel process and may occur in silos without coordination. Decisions are primarily based on fiscal impact and regulatory requirements rather than clinical data. | The Designate Approved Services/Drug Formulary process is coordinated across siloed systems, is centralized by the enterprise & is highly automated. Review processes are centralized and | A business process interfaces with other processes via federated architectures or collaborates with other processes in a peer2peer environment, eliminating redundant collection |

TABLE 24-continued

Global Health and Life Sciences High Performance
Capability Assessment Model - Public Health Services - Medicaid

| | | |
|---|---|---|
| Notification to trading partners is not timely and is labor intensive accomplished primarily on paper through use of provider mass mailings. Communications to impacted members are not linguistically, culturally or competency appropriate and socio-economic barriers to accessing information and health care are not addressed well. | standardized processes are emerging across systems, types of services and benefit packages. Decisions are based on fiscal impacts and regulatory requirements, but increased use of EDI increases accuracy of and access to clinical data to allow for analysis of health care outcomes as a determining factor. Agencies centralize provider notification and client communication functions requiring fewer staff and capitalizing on efficiencies. Communications to customers are consistent, timely and appropriate. The Agency actively supports and enables its customers to access information electronically. | and interchange of data, and improving realtime, multi-axial processing. |

TABLE 25

Global Health and Life Sciences High Performance
Capability Assessment Model - Public Health Services - Medicaid
Program Management Sub-Platform: Benefits Administration — Capability: Develop and Maintain Benefit Package

| Basic | Competitive | Market Leading |
|---|---|---|
| Benefit packages selections have pre-set services and provider types. Each eligible may be offered only packages available via eligibility determination pathway taken. | All programs introduce flexibility within benefit packages, enabling "consumer driven" health care with more choices among services and provider types available within the funding limits of all benefit packages for which the member is eligible. | Services and providers are selected within funding limits of benefit packages available to the member based on clinical and socio-economic factors |
| Within each silo, eligible may only be assigned to the best available package available despite eligibility for more expansive services because systems may be limited to supporting one eligibility span at a time. | Design of benefit packages is manual and is based on limited paper-based access to external clinical data. | Services and providers are selected within member preferences such as health status, desire to remain in the home, what is culturally appropriate, and functional competencies. |
| | | Design of benefit packages is automated with electronic access to electronic clinical data. Consumer-driven benefit packages are designed and updated real time based on collaborative interfaces with members' federated electronic health records. |

TABLE 26

Global Health and Life Sciences High Performance
Capability Assessment Model - Public Health Services - Medicaid
Program Management Sub-Platform: Benefits Administration — Capability: Develop Products and Services

| Basic | Competitive | Market Leading |
|---|---|---|
| 1.1.4.1 Conduct Product Market Analysis and Define Segments | | |
| 1.1.4.2 Position Product Concept Relative to Competition & Perform Concept Test | | |
| 1.1.4.3 Design Products and Services | | |
| 1.1.4.3.1 Develop Detailed Product Design | | |
| 1.1.4.3.2 Build product infrastructure | | |
| 1.1.4.4 Develop Product Pricing Strategy and Structure | | |
| 1.1.4.5 Obtain Regulatory Approval | | |
| 1.1.4.6 Perform Testing and Roll-Out | | |
| 1.1.4.6.1 Pilot Project | | |

TABLE 26-continued

Global Health and Life Sciences High Performance
Capability Assessment Model - Public Health Services - Medicaid
Program Management

| Sub-Platform: Benefits Administration Basic | Competitive | Capability: Develop Products and Services Market Leading |
|---|---|---|
| 1.1.4.6.2 Product Iteration | | |
| 1.1.4.7 Launch Product | | |
| 1.1.4.8 Manage Product and Segment Product Portfolio | | |

TABLE 27

Global Health and Life Sciences High Performance
Capability Assessment Model - Public Health Services - Medicaid
Program Management

| Sub-Platform: Benefits Administration Basic | Competitive | Capability: Manage Actuarial Services and Medical Economics Market Leading |
|---|---|---|
| 1.1.6.1 Manage Actuarial/Pricing Function | | |
| 1.1.6.2 Manage Medical Economics | | |
| 1.1.6.3 Manage External Reporting of Medical Cost & Quality Metrics | | |

TABLE 28

Global Health and Life Sciences High Performance
Capability Assessment Model - Public Health Services - Medicaid
Program Management

| Sub-Platform: Benefits Administration Basic | Competitive | Capability: Manage Rate Setting Market Leading |
|---|---|---|
| Notifications of rate changes are largely a manual process. | Automated notifications of rate changes. | Rate changes can be applied nationally. |
| Research staff required to conduct rate analysis for rate changes | Fewer research staff required to conduct rate analysis for rate changes. | |
| Rate updates are manually applied | Automated rate updates | |
| | Automated validation process for validating rates. Institutional services use the annual DRG Rate Setting Process to determine the Base Standard Dollar Amount (SDA) and DRG weight information for each State Fiscal Year. HHSC approves fee schedules for professional services according to set criteria for each provider type. | |

TABLE 29

Global Health and Life Sciences High Performance
Capability Assessment Model - Public Health Services - Medicaid
Program Management

| Sub-Platform: Benefits Administration Basic | Competitive | Capability: Sell Products and Services Market Leading |
|---|---|---|
| 1.1.5.1 Determine and Implement Distribution Channels | | |
| 1.1.5.2 Perform Sales to Consumers and Employers Generate Leads Create Proposals (for new & existing employers) Sell to New Employers Sell (Retail) to Consumers (new & existing) | | |
| 1.1.5.3 Perform Underwriting and Develop Account-Specific Pricing and Financial Arrangements | | |
| 1.1.5.4 Manage Quality and Performance of the Sales Process | | |

TABLE 30

Global Health and Life Sciences High Performance
Capability Assessment Model - Public Health Services - Medicaid
Care Management

| Sub-Platform: Manage Medicaid Population Health Basic | Competitive | Capability: Provide Access to Tailored Health and Wealth Messages Market Leading |
|---|---|---|
| Ensure that all client materials are accurate, appropriate, and written at a 4th to 6th grade reading comprehension level, with demonstrated comprehension by the Medicaid targeted populations. Ensure that all client materials are available in the languages of the population groups served. Ensure acceptable materials are available for the blind and visually impaired. | | |

TABLE 31

Global Health and Life Sciences High Performance
Capability Assessment Model - Public Health Services - Medicaid
Care Management

| Sub-Platform: Manage Case Basic | Competitive | Capability: Manage Medical Resource Use Market Leading |
|---|---|---|
| Perform Utilization Management Perform Prior Authorization Perform Concurrent Stay Review Perform Case Management and Disease Management Identification of member candidates Perform Case Management and Disease Management | | |

TABLE 31-continued

Global Health and Life Sciences High Performance
Capability Assessment Model - Public Health Services - Medicaid
Care Management

| Sub-Platform: Manage Case Basic | Competitive | Capability: Manage Medical Resource Use Market Leading |
|---|---|---|
| Perform Case Management a. Develop and implement case management services based on nationally recognized standards for all clients with chronic, complex, and acute medical conditions. Perform Case Management and Disease Management Perform Disease Management Perform Longitudinal case/care management (delivered by professional nurses involves following patients from the inpatient to the outpatient arena) Perform Case Management and Disease Management Perform Retrospective Review Manage outsourcing vendors Perform Case Management and Disease Management Coordinate with state agencies providing case management and other services. Evaluate the need for extension of services or alternative services when benefits cease or are exhausted. Perform Advanced Care Management Identification of member candidates Manage internal program Manage outsourcing vendors Internal or outsourced Perform Demand Management Manage Quality and Performance of the Medical Resource Use Process | | |

TABLE 32

Global Health and Life Sciences High Performance
Capability Assessment Model - Public Health Services - Medicaid
Contractor Management

| Sub-Platform: Health Services Contracting Basic | Competitive | Capability: Award Health Services Contract Market Leading |
|---|---|---|
| Indeterminate format for proposal data | Application data are standardized nationally. All verifications can be automated. Rules are consistently applied. | External and internal validation sources automatically send notice of change in contractor status. |
| Much of the information is manually validated. | Contractors can submit applications via a portal. | National interoperability permits the enrollment process to send inquiries to any other agency, stale, federal, or other entities regarding the status of a contractor. |
| Staff contact external and internal document verification sources via phone, fax. | Decisions are uniform. Some manual steps may continue. | Any data exchange partner can send a notification regarding a contractor enrolled with the state Medicaid program. |
| Decisions may be inconsistent. | Turnaround time can be immediate. | Recertification notices are automatically generated. |
| Requires large numbers of staff. | Services created for the following steps and can be shared. 1. Verify Credentials 2. Verify ID 3. Assign ID 4. Assign Rates 5. Negotiate Contract | Clinical data is accessible by direct access. Manual steps only required for exception handling. |
| Decisions may take several days. | | |

TABLE 33

Global Health and Life Sciences High Performance
Capability Assessment Model - Public Health Services - Medicaid
Contractor Management Sub-Platform: Health Services Contracting
Capability: Close Out Health Services Contract

| Basic | Competitive | Market Leading |
|---|---|---|
| At this level, the Close out Health Services Contract business process has: Indeterminate connectivity to client | At this level, the business process improves on the previous level capability by: Point-to-point or wrapped connectivity to client | The business process incorporates the previous level capability plus: Virtual records |
| At this level, the Close out Health Services Contract business process has: Inconsistent timing for response to primary client | At this level, the business process improves on the previous level capability by: Point-to-point interfaces (trading partner agreements) segregated by interface type | The business process incorporates the previous level capability plus: Use of clinical data |
| At this level, the Close out Health Services Contract business process has: Multiple data formats and semantics | At this level, the business process improves on the previous level capability by: Enhanced consistent timing for response to primary client | The business process incorporates the previous level capability plus: Focused data - data of record |
| At this level, the Close out Health Services Contract business process has: External inputs & outputs are received/sent manually via paper, telephone, & fax | At this level, the business process improves on the previous level capability by: Different interfaces with different data format and semantics | The business process incorporates the previous level capability plus: Use of metadata |
| At this level, the Close out Health Services Contract business process has: Transactions are individually reviewed using inconsistent interpretation of guidelines responded to via paper/USPD or fax | At this level, the business process improves on the previous level capability by: Transactions are received and responded to via EDI, Web Portal | The business process incorporates the previous level capability plus: Self adjusting business rules |
| | At this level, the business process improves on the previous level capability by: Virtual access to administrative and clinical records | The business process incorporates the previous level capability plus: Use of clinical data to increase the accuracy of processes |
| | At this level, the business process improves on the previous level capability by: Increased use of clinical data | The business process incorporates the previous level capability plus: Clinical staff focuses on exception cases. |
| | At this level, the business process improves on the previous level capability by: Focused data - data of record | The business process incorporates the previous level capability plus: Point-to-point collaboration |
| | At this level, the business process improves on the previous level capability by: Use of metadata | The business process incorporates the previous level capability plus: Content sensitive business logic |
| | At this level, the business process improves on the previous level capability by: Self adjusting business rules | The business process incorporates the previous level capability plus: Business Process Management |
| | At this level, the business process improves on the previous level capability by: Use of clinical data to increase the accuracy of processes | The business process incorporates the previous level capability plus: Metadata - Shared nationally |
| | At this level, the business process improves on the previous level capability by: Clinical staff focuses on exception cases | The business process incorporates the previous level capability plus: Full interoperability with other local, state, and federal programs to provide complete virtual patient clinical record and administrative data |
| | At this level, the business process improves on the previous level capability by: Members empowered to make own treatment decisions | Access to national clinical guidelines |

TABLE 33-continued

Global Health and Life Sciences High Performance
Capability Assessment Model - Public Health Services - Medicaid
Contractor Management Sub-Platform: Health Services Contracting
Capability: Close Out Health Services Contract

| Basic | Competitive | Market Leading |
|---|---|---|
| | Use of electronic Claim Attachment for Adjudication. | The business process incorporates the previous level capability plus: Most services instantly authorized or denied from point of service; payment automatically established without need of invoice Members empowered to make own treatment decisions. |

TABLE 34

Global Health and Life Sciences High Performance
Capability Assessment Model - Public Health Services - Medicaid
Contractor Management Sub-Platform: Health Services Contracting
Capability: Manage Health Services Contract

| Basic | Competitive | Market Leading |
|---|---|---|
| At this level, the business process is likely primarily paper/phone/fax based processing and some proprieiary EDI. | The business process has almost eliminated its use of nonelectronic interchange and has automated most processes to the extent feasible. | The business process interfaces with other processes via federated architectures and collaborates with other processes in a peer2peer environment, eliminating redundant collection and interchange of data |
| Timeliness of responses to inquiries and data reporting indeterminate | Agencies centralize common processes to achieve economies of scale. | At this level, the business process interfaces with other processes via federated architectures and collaborates with other processes in a peer2peer environment and improving real-time, multiaxial processing. |
| | Data is standardized for automated electronic interchanges Communications are consistent, timely and appropriate. | |

TABLE 35

Global Health and Life Sciences High Performance
Capability Assessment Model - Public Health Services - Medicaid
Contract Management Sub-Platform: Contract Information Management
Capability: Inquire Contractor Information

| Basic | Competitive | Market Leading |
|---|---|---|
| 7.3.2.1 Receipt of contract verification information data set 7.3.2.2 Determine request status as initial or duplicate 7.3.2.3 Verify requestor authorization to receive requested information 7.3.2.4 Query contractor registry for requested information 7.3.2.5 Process and log response 7.3.2.6 Prepare response data set | | |

TABLE 36

Global Health and Life Sciences High Performance
Capability Assessment Model - Public Health Services - Medicaid
Contract Management Sub-Platform: Contract Information Management
Capability: Manage Contractor Information

| Basic | Competitive | Market Leading |
|---|---|---|
| Requests are received from disparate sources in indeterminate formats. | Requests are standardized and automated. | |
| Validation is inconsistent and not rules-based. | Validation is consistent. | |
| There are delays in completing updates. | Updates are timelier | |
| Duplicate entries may go undetected. | More automation of rules to maintain integrity of data repository. | |

TABLE 36-continued

Global Health and Life Sciences High Performance
Capability Assessment Model - Public Health Services - Medicaid
Contract Management

| Sub-Platform: Contract Information Management | | Capability: Manage Contractor Information |
|---|---|---|
| Basic | Competitive | Market Leading |
| Irregular notification of change to users and processes that need to know. | Change is immediately available to users and processes that need to know. Determinate interfaces (trigger event and results; messages to external entities), standardized data, consistent business rules and decisions, easy to change business logic. Manage Contractor Information is handled by a business service. | |

TABLE 37

Global Health and Life Sciences High Performance
Capability Assessment Model - Public Health Services - Medicaid
Contractor Management

| Sub-Platform: Administration Contracting | | Capability: Award Administrative Contract |
|---|---|---|
| Basic | Competitive | Market Leading |
| The business process uses indeterminate formal for application data | The process uses application data that is standardized nationally. | At this level, the business process interfaces with other processes via federated architectures and collaborates with other processes in a peer2peer environment, eliminating redundant collection and interchange of data |
| Much of the information is manually validated. | All verifications can be automated. | At this level, the business process interfaces with other processes via federated architectures and collaborates with other processes in a peer2peer environment and improving real-time, multiaxial processing. |
| Staff contact external and internal document verification sources via phone, fax. | Rules are consistently applied. | |
| Decisions may be inconsistent. | Contractors can submit applications via a portal. | |
| Requires large numbers of staff. | Decisions are uniform. Some manual steps may continue | |
| Decisions may take several days. | Turnaround time can be immediate Services created for the following steps and can be shared 1. Verify Credentials 2. Verify ID 3. Assign ID 4. Assign Rates 5. Negotiate Contract | |

TABLE 38

Global Health and Life Sciences High Performance
Capability Assessment Model - Public Health Services - Medicaid
Contractor Management

| Sub-Platform: Administration Contracting | | Capability: Close Out Administrative Contract |
|---|---|---|
| Basic | Competitive | Market Leading |
| At this level, the business process uses indeterminate connectivity to client. | The business process has almost eliminated its use of nonelectronic interchange and uses application data that is standardized nationally. | At this level, the business process interfaces with other processes via federated architectures and collaborates with other processes in a peer2peer environment, eliminating redundant collection and interchange of data |

TABLE 38-continued

Global Health and Life Sciences High Performance
Capability Assessment Model - Public Health Services - Medicaid
Contractor Management Sub-Platform: Administration
Contracting
Basic Capability: Close Out Administrative Contract

| Basic | Competitive | Market Leading |
|---|---|---|
| Internal and external inputs and outputs are received or sent manually via paper, telephone and fax. | All verifications can be automated. Rules are consistently applied. | At this level, the business process interfaces with other processes via federated architectures and collaborates with other processes in a peer2peer environment and improving real-time, multiaxial processing. |
| Decisions may be inconsistent. | Decisions are uniform. Some manual steps may continue. | |
| Requires large numbers of staff. | Turnaround time can be immediate. | |
| Inconsistent timing for response to primary client. | | |

TABLE 39

Global Health and Life Sciences High Performance
Capability Assessment Model - Public Health Services - Medicaid
Contractor Management Sub-Platform: Administration
Contracting
Basic Capability: Manage Administrative Contract

| Basic | Competitive | Market Leading |
|---|---|---|
| The business process uses indeterminate format for application data | The process uses application data that is standardized nationally. | At this level, the business process interfaces with other processes via federated architectures and collaborates with other processes in a peer2peer environment, eliminating redundant collection and interchange of data |
| Much of the information is manually validated. | All verifications can be automated. | At this level, the business process interfaces with other processes via federated architectures and collaborates with other processes in a peer2peer environment and improving real-time, multiaxial processing |
| Staff contact external and internal document verification sources via phone, fax. | Rules are consistently applied. | |
| Decisions may be inconsistent. | Contractors can submit applications via a portal. | |
| Requires large numbers of staff. | Decisions are uniform. Some manual steps may continue. | |
| Decisions may take several days. | Turnaround time can be immediate. Services created for the following steps and can be shared. 1. Verify Credentials 2. Verify ID 3. Assign ID 4. Assign Rates 5. Negotiate Contract | |

TABLE 40

Global Health and Life Sciences High Performance
Capability Assessment Model - Public Health Services - Medicaid
Contractor Management Sub-Platform: Contractor Support Capability: Manage Contractor Communication

| Basic | Competitive | Market Leading |
|---|---|---|
| The process is primarily conducted via paper and phone. | At this level, the contractor communications are primarily electronic, with paper used only secondarily. | There is support collaborative discernment of communication needs of prospective and current contractors via PHRs. |

TABLE 40-continued

Global Health and Life Sciences High Performance
Capability Assessment Model - Public Health Services - Medicaid
Contractor Management

| Basic | Sub-Platform: Contractor Support Competitive | Capability: Manage Contractor Communication Market Leading |
|---|---|---|
| Contractor communications are likely uncoordinated among multiple, siloed programs and not systematically triggered by agency-wide processes; lacks data to appropriately target contractors; may encounter obstacles to delivery. Responses may be untimely, inconsistent and is labor intensive. | Communications are centralized ensuring agencywide coordination and greater ability to measure the efficacy of provider communications. Contractor registries use standardized contact data, including NPS address standards, to alleviate postal delivery failures. | Interoperability and data sharing agreements among states will facilitate contractor communications across state lines. |

TABLE 41

Global Health and Life Sciences High Performance
Capability Assessment Model - Public Health Services - Medicaid
Contractor Management

| Basic | Sub-Platform: Contractor Support Competitive | Capability: Perform Potential Contractor Outreach Market Leading |
|---|---|---|
| The process is primarily conducted via paper and phone. | At this level, the process is primarily electronic, with paper used only secondarily. Outreach is centralized which ensures that current and prospective providers will be able to access information. Access to standardized electronic clinical data via registries, electronic prescribing, claims and service review attachments and electronic health records, as well as use of GIS and socioeconomic indicators. Contractor registries use standardized contact data, including NPS address standards, to alleviate postal delivery failures. | The process may include automated targeting of providers via RHIO, PHRs and EHRs based on analysis of performance and business activity monitoring. Process may include collaborative discernment of individual contractor entities or organizations to whom outreach communications should be sent based on indicator algorithms that trigger during business activity monitoring at the agency. |

TABLE 42

Global Health and Life Sciences High Performance
Capability Assessment Model - Public Health Services - Medicaid
Contractor Management

| Basic | Sub-Platform: Contractor Support Competitive | Capability: Support Contractor Grievance and Appeal Market Leading |
|---|---|---|
| The process is entirely paper based, which results in poor document management and process inefficiencies that impact timeliness. Grievances and appeals are filed, managed, and resolved by siloed programs | The process conducts much of its business electronically, except where paper documents are required by law, which are OCRM for electronic data capture. Access to administrative data is readily available and standardized. | The process enables contractors to file grievances and appeals in a collaborative environment via PHRs and EHRs. Program Quality Management is better able to apply performance measures and focus business activity monitoring on operational data to detect opportunities for process, |

TABLE 42-continued

Global Health and Life Sciences High Performance
Capability Assessment Model - Public Health Services - Medicaid
Contractor Management Sub-Platform: Contractor Support  Capability: Support Contractor Grievance and Appeal

| Basic | Competitive | Market Leading |
|---|---|---|
| | | provider to alleviate issues that give rise to grievances and appeals |
| Providers may have difficulty: Finding the "Right Door" for filing grievances and appeals | Improved process timeliness, document management, and supports business activity monitoring of performance measures. | Program Quality Management is better able to apply performance measures and focus business activity monitoring on operational data to detect opportunities for contractor improvements to alleviate issues that give rise to grievances and appeals. |
| Providers may have difficulty: Accessing program rules to discern the merit of their grievance or appeal | Clinical data is still paper-based and difficult to access in a timely manner | Providers can access program rules to discern whether their grievances or appeals have merit |
| Providers may have difficulty: Getting assistance on their case or providing additional information | The process is administered as part of the Medicaid enterprise. | |
| Providers may have difficulty: Receiving consistent responses or communications that are linguistically, culturally and competency appropriate | Contractors can electronically access program rules to discern whether their grievances or appeals have merit. Communications are consistent and timely. The process supports the Program Quality Management Business Area | |

TABLE 43

Global Health and Life Sciences High Performance Capability
Assessment Model - Public Health Services - Medicaid
Provider Management

| Sub-Platform: Provider Enrollment | | Capability: Develop and Manage Network |
|---|---|---|
| Basic | Competitive | Market Leading |

6.1.3.1 Develop & Maintain Network Composition/Expansion Policy and Service Strategy
6.1.3.2 Recruit Providers
6.1.3.3 Credential and Re-Credential Providers
6.1.3.4 Contract with Providers
6.1.3.5 Develop & Maintain Contracting and Incentive Policies
6.1.3.6 Manage provider reimbursement program
6.1.3.7 Profile Providers
6.1.3.8 Manage and Monitor Provider
6.1.3.9 Manage Quality and Performance of the Network Management Process

TABLE 44

Global Health and Life Sciences High Performance
Capability Assessment Model - Public Health Services - Medicaid
Provider Management

| Sub-Platform: Provider Enrollment | | Capability: Disenroll Provider |
|---|---|---|
| Basic | Competitive | Market Leading |

6.1.2.1 Receive disenrollment request/information
6.1.2.2 Assign identifier for tracking and validate application syntax/semantic
6.1.2.3 Determine disenrollment request/information status, verify disenrollment information, and validate against state rules
6.1.2.4 Produce disenrollment record in provider registry
6.1.2.5 Request preparation of disenrollment notification and appeal rights
6.1.2.6 Request provider outreach and send relevant state policy information
6.1.2.7 Alert operations and program management disenrollment information has been loaded into the provider registry

TABLE 45

Global Health and Life Sciences High Performance
Capability Assessment Model - Public Health Services - Medicaid
Provider Management Sub-Platform: Provider Enrollment     Capability: Enroll Provider

| Basic | Competitive | Market Leading |
|---|---|---|
| Provider enrollment staff meet state and federal requirements for processing applications timely and accurately. | Provider enrollment staff receive and process paper and Web-based applications adhering to state Medicaid agency specific standards. | The enrollment process has access to all provider registries nationally via data sharing and interoperability agreements. |
| Staff receive and process paper enrollment applications and manually apply the agency's business rules resulting in creating and maintaining a provider network that provides access to benefits for eligible members. | Providers are enrolled timely and accurately with additional data that match provider to patient needs, identify provider business relationships, and support monitoring of delivery and quality of care. | Messages are automatically sent to the special programs to consider enrollment of providers mapping to criteria. |
| Decisions on application may take several days but \vithin State regulations. | The majority of applications are automated and use MITA standard interfaces for receipt of the application and the automated result messages | All enrollment application processes are automated; staff only handle exceptions. |
| Application data and format are non standard. | Most verification and validation of application information are automated. Manual intervention is required on an exception basis. | The National Health Information Network supports federated registries that identify providers across the country who are qualified to serve special populations or who are disqualified based on criminal activity. |
| Some enrollment records are stored electronically but storage is not centralized. | MITA standard interfaces are used to validate credentials and verify or obtain ID numbers. | Turnaround time is immediate, on a national scale. |
| Provider data, including ID and taxonomy, is not comparable across provider types and programs, reducing ability to monitor performance or detect fraud and abuse. | Other agencies within the state collaborate with Medicaid to offer a one-stop shop to the applicant by adopting the MITA standard interfaces. | Medicaid Provider Registries are federated with regional data exchange networks across the country and if desired, internationally. |
| Staff contact external and internal credentialing and verification sources via phone, fax. A large staff is required to meet targets for manual enrollment of providers. | There is a timely, robust, and coordinated provider network. | Authorized, authenticated parties have virtual, instant access to provider data, nationally. |
| Requires large numbers of staff. | The NPI is the ID of record. | Access to clinical data improves capability to select providers that meet quality standards. |
| Much of the application information is manually validated. | Credentials are automatically re-validated and staff receive alerts when adverse results occur. | Any daia exchange partner can send a notification regarding a provider enrolled with any program in the U.S. |
| Decisions may be inconsistent | Through use of federated registries. Medicaid staff expands its ability to identify providers with special qualifications suitable for enrollment in programs that serve special populations. | Nationally interoperable validation sources automatically send notice of change in provider status, eliminating the need to reverify, supports detection of sanctioned providers in real time anywhere in the U.S. |
| Due to limited monitoring and re-verification of enrolled providers' status, sanctioned providers may continue to be enrolled. | Members interact directly with providers. | Full automation of the process plus access to national clinical data reduces staff requirements to a core team of professionals who monitor provider network performance. |
| Focus on building a provider network that meets needs of the members. | Cultural and linguistic indicators improve selection of appropriate providers. | Prospective monitoring of program integrity during adjudication improves detection of fraud and abuse, resulting in timelier sanctioning |

TABLE 45-continued

Global Health and Life Sciences High Performance
Capability Assessment Model - Public Health Services - Medicaid
Provider Management

| Sub-Platform: Provider Enrollment | | Capability: Enroll Provider |
|---|---|---|
| Basic | Competitive | Market Leading |
| Staff do not have time to focus on cultural and linguistic compatibility, member satisfaction, or provider performance. | Turnaround time on application decision can be immediate | Clinical data can be accessed, nationally, and monitored for measuring performance. |
| | Application data interfaces are standardized nationally using MITA standards. | Performance measures can be shared via federated Provider Registries, nationally. |
| | Enrollment records are stored in either a single Provider Registry or federated Provider Registries that can be accessed by all participants. | Providers and care managers access standardized National Provider Registries and view clinical performance indicators to make informed decisions re provider selection, provider referrals. |
| | The NPI is the identifier of record. | |
| | Providers, members, and state enrollment staff have secure access to appropriate data on demand. | |
| | Performance data is only periodically measured and requires sampling and statistical calculation. | |
| | Enrollment processes continue to be handled by siloed programs according to program-specific rules. | |
| | Providers can submit on paper and electronically via a portal which improves turnaround time, but most applications are submitted electronically. | |
| | Verifications are a mix of manual and automated steps. | |
| | Electronic applications adhere to MITA standard interface requirements. | |
| | Medicaid and sister agencies collaborate on provider enrollment processes. | |
| | Manual steps may continue only for exceptions. | |
| | Process requires fewer staff and improves on results. | |
| | Shared processes and inter-agency collaboration contribute to streamline the process. | |
| | Automation of some business rules improves accuracy of validation and verification. | |
| | The emphasis on managed care and waiver programs encourages more scrutiny of and reporting to national databases. | |
| | All verifications can be automated and conducted via standardized interfaces. | |
| | Consistent enrollment rules, standardized data available from a single source support continuous performance measures that can be used to adjust rates in real time. | |
| | The agency sends verification inquiries to any other agency regarding the status of a provider. | |
| | The quality of the provider network is improved. | |
| | Guidelines ensure adequacy of network. | |
| | Members are assigned to PCPs to coordinate their care. | |
| | Members interact directly with provider and can view provider | |

TABLE 45-continued

Global Health and Life Sciences High Performance
Capability Assessment Model - Public Health Services - Medicaid
Provider Management

| Sub-Platform: Provider Enrollment | | Capability: Enroll Provider |
|---|---|---|
| Basic | Competitive | Market Leading |
| profiles and locations, make informed choices | | |
| Cultural and linguistic indications improve selection of appropriate providers. | | |

TABLE 46

Global Health and Life Sciences High Performance
Capability Assessment Model - Public Health Services - Medicaid
Provider Management

| Sub-Platform: Provider Information Management | | Capability: Manage Quality and Performance of HCD Processes |
|---|---|---|
| Basic | Competitive | Market Leading |
| Develop & Maintain Quality Policies | | |
| Evaluate, Monitor & Collect Data for Required Metric Measurement Information | | |
| Maintain & Prepare for Accreditation | | |
| Develop & Monitor COMPLAINT, Concern, Appeals (CCA) Process | | |
| Develop & Implement Quality Improvement Initiatives | | |
| Monitor and Measure Performance and Quality Management Process | | |

TABLE 47

Global Health and Life Sciences High Performance
Capability Assessment Model - Public Health Services - Medicaid
Provider Management

| Sub-Platform: Provider Information Management | | Capability: Inquire Provider Information |
|---|---|---|
| Basic | Competitive | Market Leading |
| Inquiries are received from different sources to obtain information about a provider in nonstandard formats. | Routine inquiries for provider information are standardized and automated within the agency via AVRS, Web portal, EDI | Provider registry is federated with RHIOs nationally so that any stakeholder can request provider information to the extent authorized anywhere in the country. |
| Most requests are sent via telephone, fax, or USPS. | Responses are immediate or within batch response parameters. | Pointers to selected clinical information are added to the provider registry data |
| Research is performed manually. | Responses are consistent and timely | Turnaround time is immediate, on a national scale. |
| Responses are inconsistent and manual. | A reduced work force is required to handle problems and direct telephone inquiries. | Information, including clinical, can be shared among authorized entities within the state. |
| There may be delays in responses. | MITA standard interfaces are used for inquiries regarding provider registry information. | Medicaid Provider Registries are federated with regional data exchange networks across the country and if desired, internationally. |
| Complies with agency goals and expectations. | Other agencies statewide can adopt MITA standard interfaces and participate in the inquiry process. | All authorized data exchange partners can access provider information. |
| Most requests for verification of provider information are received and responded to manually via phone, fax, USPS. | NPI is the ID of record used in the inquiry regarding provider information | Inquiries include summary clinical information relating to provider performance and quality of care. |
| Information is researched manually. There may be inconsistencies in responses. | Requests for provider information are automated via AVRS, Web portal, EDI within an agency using agency standards for messages | Automated access to information nationally further improves efficiency. |

TABLE 47-continued

Global Health and Life Sciences High Performance
Capability Assessment Model - Public Health Services - Medicaid
Provider Management

| Sub-Platform: Provider Information Management | | Capability: Inquire Provider Information |
|---|---|---|
| Basic | Competitive | Market Leading |
| Staff research and respond to requests manually. | Responses are immediate. | Regional and national, federated provider registries eliminate redundant overhead, i.e., one-stop shop inquiries. |
| Requires research staff. | Information can be shared among authorized entities within the state. | Incorporation of clinical data, nationally, improves accuracy of some responses. |
| Responses are manually validated. | Automation improves access and accuracy. | Requesters benefit from access to national clinical data as an added value. |
| Process complies with agency requirements. | Access is via Web portal and EDI channels. | |
| Requesters receive the information they need. | Data inquiry message use MITA standard interfaces, improving accuracy. | |
| | Collaborating agencies using the MITA standard interfaces can exchange data on registered providers. | |
| | Responses to requests to inquire about provider information are automated. | |
| | Fewer staff required to support | |
| | Provider information is continuously refreshed. | |
| | One stop shop for agencies who share providers. | |
| | Automation leads to fewer staff. | |
| | Number of responses per day increases significantly. | |
| | Use of MITA standard interfaces streamlines the inquiry process. | |
| | Automation improves accuracy of responses. | |
| | MITA standard interfaces produce consistent responses to inquiries. | |
| | Requesters receive immediate responses. | |
| | Requesters have a one-stop shop to access collaborating agencies to obtain information on a provider. | |

TABLE 48

Global Health and Life Sciences High Performance
Capability Assessment Model - Public Health Services - Medicaid
Provider Management

| Sub-Platform: Provider Information Management | | Capability: Manage Provider Information |
|---|---|---|
| Basic | Competitive | Market Leading |
| Changes to provider registry are managed manually. | Changes to provider registry are standardized within the agency and automated. | The agency's provider registry is federated with statewide RHIOs and is connected to all other RHIOs and registries nationally through the NHIN. |
| Accuracy of data is manually verified. There is no single standard for data stored for different types of providers. | Validation of changed data is consistent | Information and changes re a provider are shared by all entities that contract with that provider |
| Duplicate entries may go undetected. | Updates are timely (within 24 hours). | Provider registry' information includes performance measures automatically communicated from the provider's clinical record. |

TABLE 48-continued

Global Health and Life Sciences High Performance
Capability Assessment Model - Public Health Services - Medicaid
Provider Management Sub-Platform: Provider Information Management
Capability: Manage Provider Information

| Basic | Competitive | Market Leading |
|---|---|---|
| Notification to users re changes to registry is nonstandard. | Changes are immediately available to users and business processes that need to use this information. | Turnaround time is immediate, on a national scale |
| Needs of various users of provider data are uncoordinated and may be unmet. | MITA standard interfaces are used for changes to provider registry. | Updates are available to all data exchange partners. |
| Manual and semi-automated steps require some days to complete update and maintenance process. | Other agencies statewide can collaborate with Medicaid and accept the MITA standard interface | Medicaid Provider Registries are federated with regional data exchange networks across the country and if desired, internationally |
| Updates are made to data manually. Inconsistencies and inaccuracies can go undetected. Staff perform the updates manually. | NPI is the ID of record and this standard is used by all downstream business processes. Provider updates are automated with date stamp and audit trail | Information is accessible to all data exchange partners. Clinical data is included in the data set. Updates are immediately posted and accessible to all data exchange partners. |
| Requires large data entry staff. | Update can be immediate. | Clinical data is used to trigger provider registry updates. |
| Updates are manually validated. | Data exchange partners receive update information instantly. | Any data exchange partner can send a notification regarding a provider record update to any other program in the USA |
| Process complies with agency requirements. | Automated updates are consistent according to agency standards | Nationally interoperable validation sources automatically send notice of change in provider status, eliminating the need to reverify. |
| Provider update information is maintained and available to other business processes. | Dala conforms to M1TA standard interfaces. | Supports detection of sanctioned providers in real time anywhere in the USA. |
| | Provider records are stored in either a single Provider Registry or federated Provider Registries that can be accessed by all users of provider data | Can be expanded to any other country to obtain information on an immigrant or guest provider |
| | Updates are automatically processed. Edits are consistent. | Full automation of the process plus access to clinical data on a national scale reduces staff requirements to a core team of professionals who monitor provider network performance Regional, federated provider registries eliminate redundant overhead |
| | Updates are distributed to data sharing partners. One stop shop for entities who share providers. | Providers, members, and care managers access standardized National Provider Registries and view clinical performance indicators to make informed decisions re provider selection, provider referrals. |
| | Fewer staff required to support. Distributed updates of changes to provider registry reduce start requirements. | |
| | Automation improves accuracy or validation and verification of database updates. | |
| | NPI is the ID of record and standardizes ID and taxonomy updates. | |
| | In managed care and waiver settings, guidelines ensure adequacy of network | |
| | Members are assigned to PCPs to coordinate their care. | |
| | Automated maintenance of provider information ensures that timely, accurate data are available to support member assignment | |
| | Members can view provider | |

TABLE 48-continued

Global Health and Life Sciences High Performance
Capability Assessment Model - Public Health Services - Medicaid
Provider Management

| Sub-Platform: Provider Information Management | | Capability: Manage Provider Information |
|---|---|---|
| Basic | Competitive | Market Leading |
| | profiles and locations, make informed choices. Cultural and linguistic indicators improve selection of appropriate providers. Provider and member satisfaction improves because of speed and accuracy of enrollment process | |

TABLE 49

Global Health and Life Sciences High Performance
Capability Assessment Model - Public Health Services - Medicaid
Provider Management

| Sub-Platform: Provider Support | | Capability: Develop and Maintain Medical and Network Policies |
|---|---|---|
| Basic | Competitive | Market Leading |
| 6.3.4.1 Develop and Maintain Contracting and Reimbursement Policies Define Standard Contracting Methodologies Define approved non-standard variations and rules for use 6.3.4.2 Develop and Maintain Medical Policies Define approved sources of external clinical information/ current practices Create external review & advice boards 6.3.4.2 Develop and Maintain Medical Policies Determine and monitor state/ federal requirements and impacts on medical policy and its application 6.3.4.3 Develop and Maintain Network Strategy and Plan | | |

TABLE 50

Global Health and Life Sciences High Performance
Capability Assessment Model Public Health Services - Medicaid
Provider Management

| Sub-Platform: Provider Support | | Capability: Manage Pharmacy |
|---|---|---|
| Basic | Competitive | Market Leading |
| 6.3.5.1 Develop & Maintain Pharmacy Contracting Business terms NCPDP and code issues 6.3.5.2 Perform Pharmacy Prior Authorization 6.3.5.3 Perform Pharmacy Retrospective Review 6.3.5.4 Perform Pharmacy Credentialing 6.3.5.5 Manage Specially Pharmacy Contracting terms Prior Authorization | | |

TABLE 51

Global Health and Life Sciences High Performance
Capability Assessment Model - Public Health Services - Medicaid
Provider Management

| Sub-Platform: Provider Support | | Capability: Manage Provider Communication |
|---|---|---|
| Basic | Competitive | Market Leading |
| Requests are received from providers in non-standard formats. Most requests are sent via telephone, fax, or USPS. | Routine requests from providers are standardized and automated within the agency via AVRS, Web portal, EDI. | Medicaid provider registry is federated with RHIOs on a national scale which enables the Medicaid agency to reach all targeted providers statewide to receive general communiqués or public health alerts. |
| Research is performed manually. | Research and response for these standardized communications are immediate or within batch response parameters. | All health care agencies are able to collaborate in sending and receiving communications between agencies and among all |

TABLE 51-continued

Global Health and Life Sciences High Performance
Capability Assessment Model - Public Health Services - Medicaid
Provider Management Sub-Platform: Provider Support     Capability: Manage Provider Communication

| Basic | Competitive | Market Leading |
|---|---|---|
| Responses are inconsistent and manual. There may be delays in responses. | Routine responses are consistent and timely and require fewer staff. | providers statewide. Many typical provider communications are handled directly by connectivity between the provider's clinical record system and the Medicaid agency |
| Complies with agency goals and expectations. | The majority of communications is automated. | Requests can be received and responded to nationally and internationally. |
| Requires significant labor force. | MITA standard interfaces are used for automated messages between provider and agency | Messages can be sent from one state Medicaid to providers in other states depending on inter-agency agreements. |
| Provider communication is not coordinated among multiple, siloed programs and not systematically . . . | Provides a one-stop shop for frequently asked questions for Medicaid and other collaborating agencies that accept the MITA standard interfaces. | Indicator algorithms can trigger communication messages directly to the provider. |
| No emphasis on linguistic, cultural or competency-based considerations. | Communications are standardized within the Medicaid agency. | Inquiry and response, and communications sent by the agency are immediate. Turnaround time is immediate, on a national scale |
| May encounter obstacles to delivery. | Use of electronic communications makes provision of appropriate messages more feasible and cost-effective. | Interaction between provider clinical data and the agency is automatic. |
| Manual and semi-automated steps may require some days to complete response. | Provider registries use standardized contact data, including NPI address standards, to alleviate postal delivery failures. | Medicaid Provider Registries are federated with regional data exchange networks across the country and if desired, internationally. |
| Responses are made manually and there may be inconsistency and inaccuracy (within agency tolerance level). | Provider requests and responses are automated via Web, AVRS, EDI with dale stamp and audit trail. | Responses are standardized and are immediately available. |
| Staff research and respond to requests manually. | Inquiries and responses using MITA standard interfaces are immediate. | The provider clinical record information can trigger messages to and from the provider and the Medicaid agency. |
| Requires large research staff. | Automated response increase accuracy | Access to clinical information can improve efficiency especially in alert messaging |
| Responses are manually validated, e.g., call center audits; provider satisfaction survey. Process complies with agency requirements. | Access is via Web portal and EDI channels. | Automated access to information nationally further improves efficiency. |
| Providers receive the information they need. | Requests and responses are standardized as MITA interfaces, improving accuracy. | Full automation of the process plus access to national clinical data reduces staff requirements to a core team of professionals who monitor provider satisfaction with responses to inquiries. |
| | Provider information is accessed via either a single Provider Registry' or federated Provider Registries. | Access to national clinical data improves accuracy of targeted alerts. |
| | Provider information belonging to different entities can be virtually consolidated to form a single view. | Some inquiries/responses are replaced by automated messaging, on a national scale. |
| | Responses to routine provider requests are automated. | |
| | Fewer staff required to support. Information requested by provider is continuously refreshed | |
| | Collaboration among agencies achieve a one-stop shop to provider inquiries. | |
| | Automation leads to fewer staff. Number of responses per day increases significantly. | |

TABLE 51-continued

Global Health and Life Sciences High Performance
Capability Assessment Model - Public Health Services - Medicaid
Provider Management Sub-Platform: Provider Support    Capability: Manage Provider Communication

| Basic | Competitive | Market Leading |
|---|---|---|
| | Use of MITA standards and collaboration among agencies increases effectiveness. Automation improves accuracy of responses. MITA standard interfaces specify requests and response messages and are used by collaborating agencies in the state. Providers have no delay in obtaining responses. Providers have a one stop shop to access collaborating agencies to obtain information. | |

TABLE 52

Global Health and Life Sciences High Performance
Capability Assessment Model - Public Health Services - Medicaid
Provider Management Sub-Platform: Provider Support    Capability: Manage Provider Grievance and Appeal

| Basic | Competitive | Market Leading |
|---|---|---|
| This is an all-manual process. Grievances and appeals are filed via fax and USPS. | Grievance and appeal cases are filed via USPS and fax. | Clinical data is automatically accessed to substantiate case findings. |
| Requests for documents are managed manually. | Documents are scanned and the case file is automated and can be shared among case workers. | Automated business rules that include clinical data lead to earlier resolution of cases. |
| Confidential documents are transferred by certified mail. | Some review steps are automated using agency specific standards. | The original case against a provider may be triggered directly from the clinical record. |
| Verification of information is handled manually | Time required to develop the case is reduced. | Interoperability and data sharing agreements across states facilitate case resolution. |
| The process is lengthy | There is more consistency in the steps taken in the review and resolution process. | Responses to research questions are immediate. |
| There may be inconsistencies between cases of same type | MITA standard interfaces are used for Grievance and Appeal triggers and results | Turnaround time of information gathering is immediate, on a national scale. |
| This is an all-manual process. Cases typically require months to complete. | MITA standard interfaces are used to initiate and develop the case. | Medicaid Provider Registries are federated with regional data exchange networks across the country and if desired, internationally. |
| Information is researched manually | Case file is Web-enabled; information is shared among staff in managing the case. | All authorized data exchange partners can access provider information, including clinical data. |
| There may be inconsistencies in responses. | Medicaid collaborates with other health and human service agencies that manage appea/s (o create a one-stop shop model for both provider and consumer appeals. | Automated access to information nationally further improves efficiency. |
| There are no standards for case data. | Requests for provider information are automated via AVRS, Web portal. EDI within an agency | Automated business rules that include clinical data lead to earlier resolution of cases |
| Staff research and maintain manually. | Responses to research questions within the agency are immediate across all data sharing partners within the state. | The original case against a provider may be triggered directly from the clinical record. |

TABLE 52-continued

Global Health and Life Sciences High Performance
Capability Assessment Model - Public Health Services - Medicaid
Provider Management Sub-Platform: Provider Support       Capability: Manage Provider Grievance and Appeal

| Basic | Competitive | Market Leading |
|---|---|---|
| Process is labor-intensive. | Over all timeline to resolve a case is shortened. | Full automation of the process plus access to national clinical data reduce staff requirements to a core team of professionals who monitor stakeholder satisfaction with responsiveness to inquiries. |
| Results take several months. | Automation improves access and accuracy. | Regional and national, federated provider registries eliminate redundant overhead. |
| Terms of the settlement or results of the hearing are manually documented according to the administrative rules of the state. | Access is via Web portal and EDI channels. | Incorporation of national clinical data improves accuracy of final disposition of the case. |
| There may be inconsistencies between similar cases. | Agency standards for inquiries are introduced. | Use of national clinical evidence reduces false positives and improves consistency of results. |
| Process complies with agency requirements Business process complies with agency and state requirement for a fair hearing and disposition. | Standard MITA interfaces improve accuracy of content. Responses to requests to verify provider case information are automated. Fewer staff required to support. MITA standard interfaces standards are used for creation of a case and publication of results. MITA standard interfaces are also used for inquiry and response to acquisition of information needed to build the case. Automation of some research steps reduces level of staffing required to manage a case. Collaboration with sister agencies that conduct appeals cases increases cost-effectiveness. Standardization of input and case results allows staff to focus on analytical activities. Automation is introduced into the case management process. Results are documented and recorded and can be accessed and retrieved as needed. MITA standard interface improves accuracy of case results. The provider and the agency benefit from introduction of automation to speed up the case resolution. Agencies benefit from introduction of MITA standard interfaces. Providers benefit from consistency and predictability of the process. | |

TABLE 53

Global Health and Life Sciences High Performance
Capability Assessment Model - Public Health Services - Medicaid
Provider Management Sub-Platform: Provider Support | | Capability: Perform Provider Outreach

| Basic | Competitive | Market Leading |
|---|---|---|
| The business process is primarily manual. | Increased use of agency standards for provider data improves identification of targeted, enrolled providers; and aids in identification of provider gaps. | Provider clinical information can trigger outreach and educational material that are automatically generated and sent to the provider. |
| Agencies use TV, radio, posters for public transportation and community centers and clinics, and newspaper advertisements to distribute outreach and educational information to targeted providers. | Electronic outreach and educational materials are available to providers via a Web portal. | States can share provider outreach and education materials with other states. |
| Identification of targeted enrolled providers is based on provider registry data and claims history. | Standard educational and policy information for enrolled providers is maintained electronically by the agency and is distributed to the providers via electronic media | Triggers create messages from provider clinical records that map to automated response messages contained in an Outreach and Education database. |
| Outreach is uncoordinated among multiple, siloed programs. | Automated translation and repositories of cultural and competency appropriate statements makes provision of appropriate outreach material more feasible and cost-effective. | Turnaround time to identify target provide and transmit information is immediate. |
| Linguistic and cultural sensitivity refinements are absent. | Use of GIS and socioeconomic indicators support targeting providers for outreach. | Turnaround time for triggering, sending appropriate information is immediate, on a national scale. |
| Quality and consistency of outreach and education efforts are difficult to maintain. | Provider registries, use standardized contact data, including NPI, to alleviate postal delivery failures. | CMS can send NPI and PDP messages to all providers via federated registries. |
| The agency may encounter obstacles to delivery. | Outreach and education materials are available via state Medicaid portal and are shared with other collaborating agencies. | Medical Provider Registries are federated with regional data exchange networks across the country |
| Outreach and education materials are manually prepared and updated. | Electronic storage and dissemination of provider manual materials shortens the time to reach the provider. Non-routine outreach is still timeconsuming. | Access to clinical data facilitates identification of targeted providers and focuses the outreach or education message. |
| Provider manuals are constantly revised and new pages are mailed to providers. | Outreach and education information are immediately available to providers across collaborating agencies. | Access to clinical information improves efficiency by automatically mapping provider who needs assistance with generation of appropriate materials. |
| Preparation of materials is clunky. | Automation improves access and accuracy | Automated business rules that include clinical data lead to faster identification of target list |
| Information is subject to inaccuracies and inconsistencies. | Access is via Web portal for outreach material and via electronic media for routine information distributed to enrolled providers. | Outreach and education can be interoperable among states sharing business services. |
| Staff develop and maintain materials manually. | Provider information is accessed via federated Provider Registries that can be accessed by all authorized entities within the state | Full automation of the process of identification of need plus access to clinical data reduces staff requirements. |
| Effort is required to research target provides population and track mailings. | Identification of targeted providers and dissemination of information improve in accuracy. | Regional, federated provider registries eliminate redundant overhead in locating addresses |
| Process is labor-intensive and incurs postal expense. | Materials can be posted on a Web site for downloading by providers. | Outreach and education can be interoperable among states sharing MITA standard interfaces |
| Difficult to determine impact of outreach and education. | Easier to identify target population and disseminate appropriate information. | Incorporation of clinical data improves accuracy of identification or targeted providers and dissemination of appropriate messages. |

TABLE 53-continued

Global Health and Life Sciences High Performance
Capability Assessment Model - Public Health Services - Medicaid
Provider Management Sub-Platform: Provider Support                    Capability: Perform Provider Outreach

| Basic | Competitive | Market Leading |
|---|---|---|
| Studies are conducted to see if there are improvements in provider performance associated with outreach and education | Automation reduces level of staffing required to perform outreach and education. | Access to provider information on a regional or national basis. |
| Business process complies with agency and state requirements for educating the provider network regarding rules and regulations and how to communicate with the agency. | Easier to identify target population and disseminate appropriate information. | Provider registries improve accuracy of contact information. |
| | Use of portal by provider is monitored to ensure that all are actively engaged in downloading information. Easier to target provider populations and disseminate information appropriate to the needs. Agency can target providers who are not accessing information. Provider and agency benefit from introduction of automation to speed up the outreach and education process. Agencies benefit from sharing of information with other agencies. Providers benefit from consistency and timeliness of the information transmitted. | Outreach and education communications can be triggered by automated messaging |

TABLE 54

Global Health and Life Sciences High Performance
Capability Assessment Model - Public Health Services - Medicaid
Member Management Sub-Platform: Eligibility Determination           Capability; Determine Eligibility

| Basic | Competitive | Market Leading |
|---|---|---|
| At this level, the business process is designed to serve social services programs and FFS Medicaid programs. | The business process benefits from member centric. No Wrong Door initiatives and the technology support provided by SOA and rules-engines to meet the needs of programs besides FFS. | The business process has ease of access to external sources of data, including clinical data |
| The process is constrained by FAMIS or state eligibility system functionality. | All programs introduce flexibility within benefit packages. | National interoperability permits the eligibility process to send inquiries to any other agency, state, federal, or other entities in any part of the country. |
| Indeterminate format for application data. | Application data are standardized. All verifications can be automated. Rules are consistently applied. | External and internal validation sources automatical!)' send notice of change in member status. |
| Information is manually validated. | Decisions are uniform. Some manual steps may continue. | Direct access to clinical data improves the determination process. Manual validation steps only required for exception handling. |
| Staff contact external and internal document verification sources via phone, fax. | Requires fewer staff. | Agency receives automated notifications from the SSA and other in-state and state and federal agencies with which it has data sharing agreements. |

TABLE 54-continued

Global Health and Life Sciences High Performance
Capability Assessment Model - Public Health Services - Medicaid
Member Management

| Sub-Platform: Eligibility Determination | | Capability; Determine Eligibility |
|---|---|---|
| Basic | Competitive | Market Leading |
| Decisions may be inconsistent. | Turnaround time can be immediate. | Consumer-driven benefit packages are designed and updated real time based on collaborative interfaces with members' federated electronic health records. |
| Requires large staff. | Different types of eligibility pathways are merged into a single process. | |
| Decisions take several days. | Spend-down is calculated automatically by the Calculate Spend-down process in the Operations Management, Member Payment business area. | |
| There are many pathways for determining eligibility. | Spend-down is treated as a deductible that these eligibles must pay out-of-pocket before Medicaid will pay. | |
| When eligibility information is transferred from FAMIS to MMIS, it must be converted and data is lost. | | |
| Benefit packages selections have pre-set services and provider types. | | |
| Spend-down amounts are calculated manually. | | |
| Member's record reflects whether spend-down amount is reached. | | |

TABLE 55

Global Health and Life Sciences High Performance
Capability Assessment Model - Public Health Services - Medicaid
Member Management

| Sub-Platform: Enrollment | | Capability: Disenroll Member |
|---|---|---|
| Basic | Competitive | Market Leading |
| 9.2.1.1 Receive member eligibility termination request | | |
| 9.2.1.2 Assign identifier and track processing status of eligibility termination and disenrollment request | | |
| 9.3.1.3 Validate compliance of state application submission rules. | | |
| 9.2.1.4 Verify demographic data and residence does not meet enrollment requirements | | |
| 9.2.1.5 Create disenrollment data set to load disenrollment record into member registry | | |
| 9.2.1.6 Alert applicant, provider, and contractor systems disenrollment information is loaded into member registry to prepare notifications | | |
| 9.2.1.7 Prepare education materials for disenrollment reason in member outreach process | | |
| 9.2.1.8 Alert operations, payment and billing systems of member disenrollment | | |

TABLE 56

Global Health and Life Sciences High Performance
Capability Assessment Model - Public Health Services - Medicaid
Member Management

| Sub-Platform: Enrollment | | Capability: Enroll Member |
|---|---|---|
| Basic | Competitive | Market Leading |
| Enrollment processes are paper-based and siloed within | Automated business rules facilitate design or seamless and | Enrollment/eligibility determination processes are |

TABLE 56-continued

Global Health and Life Sciences High Performance
Capability Assessment Model - Public Health Services - Medicaid
Member Management Sub-Platform: Enrollment  
Capability: Enroll Member

| Basic | Competitive | Market Leading |
|---|---|---|
| programs with no cross program coordination. | coordinated package of quality. | automated services triggered by point of service applications including PHRs and EHRs and run collaboratively. |
| Stall makes decisions autonomously and without consultation with other programs. | All verification of financial, socio-economic and health status information is automated and some is real time. | If the provider's system is service enabled, it can prepopulate appropriate enrollment application(s) and to request additional information needed from the provider/applicant. |
| Eligibility determination must precede enrollment and is done separately. | Contractors and providers can query the registry to determine eligibility and program enrollment | The applicant is able to use online PHR or Web portal to fill out a pre-populated application. |
| Enrollment policies, procedures, benefits and application forms are program specific. | Contractors may batch download enrolled members rather than receive theHIPAA834. | Automated verification and application response are real time. |
| Applicants must submit paper application forms to each program separately and responses may take several days. | Process takes less time. Although data is electronic, some of the reviewed verification of information for waiver programs must be done manually. | Benefits are memberspecific, seamless and coordinated package of quality. |
| Process focus is on manually applying the agency's business rules to ensure that enrollment meets state and federal requirements. | Turnaround time on application decision can be immediate. | The Agency can automatically query regional patient registries for member enrollment information for verification and adjudication purposes such as COB |
| Staff manually verifies financial, socio-economic and health status information. | Medicaid and contractor member registries are updated in near real time as changes occur. | Agency receives automated enrollment notifications from the SSA, EHRs, PHRs, intraand interstate sources and federal agencies. |
| Enrollment in managed care and waiver program requires cumbersome extension of traditional fee-for-service processes. | Managed care enrollment is rule driven and automated | Turnaround time is immediate, on a national scale |
| Benefits cannot be "blended" across programs. | Enrollment application and exchange data are standardized nationally among Medicaids improving access and accuracy. | Member registries are federated with regional data exchange networks across the country and if desired, internationally. |
| Staff does not have the time or means to focus on meeting members' health, functions, cultural or linguistic needs. | All programs use the HIPAA834 Enrollment transaction and implement a standard response transaction from the contractors for corrections. | Agency automatically receives standardized, timely and complete enrollment data notifications about members for verification and adjudication purposes. |
| Staff must send paper enrollment notification to contractors. | Enrollment records are stored in either a single member registry or federated Agency member registries that can be accessed by all applications. | Authorized, authenticated parties have virtual, instant access to enrollment data, nationally. |
| Decisions on application may take several days, longer if verification of information is difficult. | Member IDs are linked algorithmically based on other standardized data so that enrollment records are automatically linked across programs. | Any data exchange partner nationally, and even internationally, can query and receive appropriate data relating to an enrolled member |
| Contractors do not receive timely enrollment information. | Providers, members and state enrollment staff have secure access to appropriate and accurate data on demand | Enrollment alerts to providers reduces staff needed for enrollment outreach and verification of health status. |
| Enrollment data and format are indeterminate. | Performance data is only periodically measured and requires sampling and statistical calculation. | More effective enrollment data exchange because information about all enrollment events of interest are pushed vs. querying potential sources of enrollment data. |

TABLE 56-continued

Global Health and Life Sciences High Performance
Capability Assessment Model - Public Health Services - Medicaid
Member Management

| Sub-Platform: Enrollment | | Capability: Enroll Member |
|---|---|---|
| Basic | Competitive | Market Leading |
| Enrollment applications are not standardized and may still be hard copy. | Applications are only submitted electronically | Ability to auto/ad hoc query federated registries to access enrollment and verification data increases data reliability and completeness, ensuring better process results. |
| Some enrollment records are stored electronically but storage is not centralized. | Medicaid centralizes all member enrollment processes, has a single set of enrollment rules. | ". . . events of . . . ty and . . . [proce? ]ss results." ABOVE TEXT IS OBSCURED BY THE FOLLOWING TEXT IN A BOX OVERLAPPING IT: Medicaid centralizes all member enrollment processes; has a single set of enrollment rules. |
| Member data is not comparable across programs reducing ability to monitor program outcomes or detect fraud and abuse. Notifications to contractors are state-specific and differ by contractor type. | "Enrollments and verif . . . automated/* ABOVE TEXT IS OBSCURED BY THE FOLLOWING TEXT IN A BOX OVERLAPPING IT: Medicaid centralizes all member enrollment processes; has a single set of enrollment rules. | Applicants are "presumptively eligibili/ed/enrolled" automatically at the point of care based on national verification of health and socio-economic data, ensuring immediate access to needed healthcare |
| Notifications to contractors are state-specific and differ by contractor type. | Services created for the enrollment process can be shared among states. | |
| Enrollment may occur in silos without coordination, i.e., different processes and multiple pathways for each type of enrollment. | Process requires fewer staff and improves on results. | |
| Applicants and members can submit applications, make inquiries and choose providers and MCOs on paper. | Shared services and inter-agency collaboration contribute to streamline the process. | |
| Staff contact external and internal financial, socioeconomic, demographic and health status verification sources via phone, fax. | Fewer applicants and members are enrolled erroneously, reducing program costs. | |
| Requires a large staff to meet targets for manual enrollment of members. | Automation of business rules improves accuracy of validation and verification. | |
| Siloed enrollment processes result in redundant infrastructure, effort and costs. | Automation of enrollment and verification data interchange improves timeliness and quality of data. | |
| Much of the application information is manually validated and verification may be difficult. | Automated application of enrollment business rules improves consistency | |
| Decisions may be inconsistent. | Permits blending of program benefits to provide more appropriate services to members. | |
| Ineligible members may continue to be enrolled due to limited monitoring and re-verification of enrolled member status. | Synchronization of eligibility and enrollment processes ensures data and decision consistency, thereby improving results. | |
| MMIS and Contractor member registries frequently are not synchronized. | Automated enrollment coordination of program benefits improves the members' access to appropriate services and compliance with state/federal law. | |

TABLE 56-continued

Global Health and Life Sciences High Performance
Capability Assessment Model - Public Health Services - Medicaid
Member Management

| Sub-Platform: Enrollment | | Capability: Enroll Member |
|---|---|---|
| Basic | Competitive | Market Leading |
| Focus is on accurately processing enrollment and manually verifying information as efficiently as possible. Staff does not have time to focus on health, functional, cultural and linguistic compatibility of provider or program for the member, or member satisfaction. | Members experience a seamless and efficient eligibility/enrollment process no matter how or where they contact the Agency. Members receive benefit packages, specifically designed to meet individual's health, functional, cultural and linguistic needs. | |

TABLE 57

Global Health and Life Sciences High Performance
Capability Assessment Model - Public Health Services - Medicaid
Member Management

| Sub-Platform: Enrollment | | Capability: Perform Underwriting |
|---|---|---|
| Basic | Competitive | Market Leading |
| 9.2.3.1 Develop New Business Quote
9.2.3.2 Complete Underwriting Case Installation Tasks
9.2.3.3 Conduct Financial Account Management
9.2.3.4 Produce Customer Financial Reports
9.2.3.5 Develop Renewal Quote & Implement Sold Rates
9.2.3.6 Prepare Year-End Customer Settlement
9.2.3.7 Manage Underwriting Operations
9.2.3.8 Manage Underwriting Support | | |

TABLE 58

Global Health and Life Sciences High Performance
Capability Assessment Model - Public Health Services - Medicaid
Member Management

| Sub-Platform: Member Information Management | | Capability: Inquire Member Eligibility |
|---|---|---|
| Basic | Competitive | Market Leading |
| Most requests for verification of member information are received and responded to manually via phone, fax, USPS. | Member eligibility/enrollment verification is automated via AVRS, point of services devices, Web portal, EDI, but remains siloed. | Turnaround time is immediate, on a national scale. |
| Information is researched manually. There may be inconsistencies in responses. | Responses can be immediate | Information, including clinical, can be shared among authorized entities within theRHIO. |
| Staff research and respond to requests manually. High rate of erroneous eligibility information. | Information can be shared among entities authorized by the Agency. | Medicaid Member Registries are federated with RHIOs. |
| Verification takes effort and too much time for providers. | Automation improves access and accuracy. | Medicaid Member Registries are federated with regional data exchange networks across the country and if desired, internationally. |
| | Access is via AVRS, point of sen ice devices, Web portal, and EDI channels. | All authorized data exchange partners can access member information |
| Requires research staff. Mailing ID cards to members monthly is costly. Verification is too expensive for providers to use for each encounter but providers risk cost of denied claims for ineligible members and noncovered services. | Increased use of HIPAA eligibility/enrollment data but not the program and benefit data Member eligibility/enrollment, program, and benefit data and messaging formats adhere to MITA standard interfaces Member information is accessible from federated Member | Access to clinical information can improve efficiency for treatment, payment and operations. Automated access to information nationally further improves I efficiency. Full automation of the process |

TABLE 58-continued

Global Health and Life Sciences High Performance
Capability Assessment Model - Public Health Services - Medicaid
Member Management

| Sub-Platform: Member Information Management | | Capability: Inquire Member Eligibility |
|---|---|---|
| Basic | Competitive | Market Leading |
| Responses are manually validated. | Registries within the state Enterprise. | plus access to clinical data reduces staff requirements to a core team of professionals. |
| Process complies with agency requirements. | Responses to requests to verify member information are automated. | Regional, federated provider registries eliminate redundant overhead. |
| Requestors receive the information they need. | Fewer staff required to support. Electronic verification is easier and faster, so providers use it more often. | Access to member information on a national basis. |
| | Member information is continuously refreshed. | Incorporation of clinical data, on a national scale, improves accuracy' of some responses. |
| | One stop shop for programs that share members. | Some inquiries/responses are replaced by automated messaging, on a national scale, where authorized. |
| | Automation leads to few staff. Number of responses per day increases significantly. Electronic verification lowers cost to providers and reduces denied claims for ineligible members and non-covered services. Use of MITA standard interfaces increase cost-effectiveness. Because covered services are included in eligibility verification responses, providers experience fewer claim denials based on noncovered services. Automation improves accuracy of responses. Business services standardize requests and responses nationally More robust use of the HIPAA transactions increases accuracy-. Providers have no delay in obtaining responses. Providers have a one stop shop to access collaborating agencies to obtain information. | |

TABLE 59

Global Health and Life Sciences High Performance
Capability Assessment Model - Public Health Services - Medicaid
Member Management

| Sub-Platform: Member Information Management | | Capability: Manage Member Information |
|---|---|---|
| Basic | Competitive | Market Leading |
| The business process is designed to serve FFS Medicaid programs and meet MMIS certification requirements such as MARS and MSIS reporting. | Updates are automated with date stamp and audit trail; notification to interested users and processes is immediate. | At this level, the business process improves data availability and access for external users nationally. |
| Data requests are received from disparate sources in indeterminate formats. | Integration with FAMIS supports day based eligibility/enrollment. | Member Registry accessed collaboratively by authorized data sharing partner applications nationally during shared business processes such as verifying COB. |

TABLE 59-continued

Global Health and Life Sciences High Performance
Capability Assessment Model - Public Health Services - Medicaid
Member Management Sub-Platform:
Member Information Management   Capability: Manage Member Information

| Basic | Competitive | Market Leading |
|---|---|---|
| Data is shared in batch on a scheduled or ad hoc basis. Validation is inconsistent and not rules-based. | Member information is integrated via Member registry. Standard interfaces. | Member information can be shared across states Ability to access clinical data electronically to calculate performance and outcome measures. |
| There are delays in completing updates and loading member data generated from multiple sources. | Standardized data | Turnaround time is immediate, on a national scale. |
| Duplicate entries may go undetected. | Consistent business rules and decisions. | Updates are available to all authorized data exchange partners. |
| Irregular update notification to interested users and processes. | Easy to change business logic. | Medicaid Member Registries are federated with regional data exchange networks across the country and if desired, internationally. |
| Agencies may be limited to monthly eligibility periods vs. day based eligibility/enrollment. | Manage Member Information is handled by a business service. | Updates notifications are automatically sent to all authorized interested data exchange partners. |
| Manual and semi-automated steps delay updates, maintenance processes and require system down-time. | Member updates and data extractions can be immediate. | Any data exchange partner can send a notification regarding a member record update to any other program in the USA. |
| Inadequate audit trails. | Data exchange partners receive update notifications instantly. | Nationally interoperable validation sources automatically send notice of change in member enrollment and socioeconomic status in real time anywhere in the USA. |
| Updates are made to individual files manually. | Automated updates are made to individual files and databases. Databases may be relational. | Ability to access clinical data electronically to calculate performance and outcome measures. |
| Data issues duplicate identifiers, discrepancies between data stores, and information quality and completeness. | Updates, notifications, and data extractions are standardized. | Clinical data could be used to trigger member registry updates and to push member data to other applications. |
| Staff must key new information, make updates manually, reconcile and validate manually. | Member records are stored in either a single Member Registry or federated Member Registries that can be accessed by all authorized applications. | Full automation of the process plus access to clinical data on a national basis reduces staiT requirements to a core team of professionals. |
| Legacy systems limit Agency's ability to start and end eligibility in the MCOs within a month. | Updates are distributed to data sharing partners. One stop shop for entities who share members. | Regional, federated member registries eliminate redundant overhead. |
| Requires numerous data entry staff to key new and updated information, and reconcile duplicates and data inconsistencies. | Updates are automatically processed. Edits are consistent. | Using clinical data electronically vs. paper charts lowers costs to calculate performance and outcome measures. |
| IT staff needed to load member information generated from other systems. | Fewer staff required to support. | Automation and association of clinical data to member records improves accuracy of enrollment, performance measurement and care management processes. |
| Updates and reconciliations must be manually validated. | MCO premiums are paid on a daily rate, lowering capitation premium costs for ineligible members. | National access to member enrollment/clinical data improves research, reporting, performance measures, outcome studies, care/disease management, and fraud detection. |
| Process focus is on compliance with agency requirements and less on ensuing timely availability of quality/complete data for users. | Distributed update notifications to federated member registries and automation reduces staff requirements | Providers, members, and care managers access standardized Member Registries on a national scale to view clinical data needed for EHRs, PHRs, and care/disease management. |

TABLE 59-continued

Global Health and Life Sciences High Performance
Capability Assessment Model - Public Health Services - Medicaid
Member Management Sub-Platform:
Member Information Management    Capability: Manage Member Information

| Basic | Competitive | Market Leading |
|---|---|---|
| Member information is maintained and available to other business processes and users. | Member data is associated algorithmically to support federated access, automated updates, reconciliation and extraction of complete and quality data | Ability to access de-identified member clinical data electronically to calculate performance and outcome measures improves member and regional patient care. |
| Inquiries about members' eligibility/enrollment are received in non-standard formats. | Automation improves accuracy of validation, verification, and reconciliation of data base updates. | Medicaid Member Registries are federated with RHIOs nationally. |
| Providers cannot be sure of the source from which to request eligibility verification. | Automated maintenance of member information ensures that timely, accurate data are available to support all processes needing member information | Providers can inquire about member health records in other states. |
| Most requests are sent via telephone, fax or point of service device. Media, data format and content differ by program. | Data Accessibility increases the efficiency, speed, and accuracy of eligibility/enrollment and other processes. | Requests are expanded to include inquiries re clinical information. |
| Providers often depend on paper member ID cards that can be inaccurate. | The sources of eligibility information are siloed within different programs. | Eligibility verification, program, benefit, and Member Registry health record locator services are integrated into applications. |
| Newly eligible members must wait to receive mailed ID cards or the provider must verify eligibility by telephone Verification is performed manually | Routine inquiries for member information are automated. Responses are immediate or within batch. MITA standard interfaces incorporate full HIPAA data schemas. | |
| Responses are inconsistent, sometimes incorrect, and untimely. | Member information is integrated via a Member Registry. Sister agencies adopt MITA standard interfaces to present a one-slop shop for inquiries regarding enrolled members. | |

TABLE 60

Global Health and Life Sciences High Performance
Capability Assessment Model - Public Health Services - Medicaid
Member Management Sub-Platform: Prospective and    Capability:
Current Member Support    Manage Applicant and Member Communication

| Basic | Competitive | Market Leading |
|---|---|---|
| Member communications are primarily conducted via paper and phone. | Member communications are primarily electronic, with paper used only as needed to reach populations. | Certain messages to member are triggered by an individual's entries into personal health records for prospective and current members. |
| Member communications are uncoordinated among multiple, siloed programs and not systematically triggered by agency-wide processes. | Member communication is organized around the "no wrong door" concept. | Member communications posted by an agency can be accessed by a member anywhere in the country. |
| Requests are received from members in non-standard formats. | Agencies support deployment of internet access points to alleviate communications barriers. | Information entered into provider electronic health records can also trigger specific messages to members regarding special programs and disease management information. |

TABLE 60-continued

Global Health and Life Sciences High Performance
Capability Assessment Model - Public Health Services - Medicaid
Member Management

| | Sub-Platform: Prospective and Current Member Support | Capability: Manage Applicant and Member Communication |
|---|---|---|
| Basic | Competitive | Market Leading |
| Most requests are sent via telephone, fax, or USPS. | Use of electronic communications makes provision of appropriate member communications more feasible and cost-effective. | Personal health records are available for free via the internet and accessible via kiosk and low cost telecommunication devices. |
| Research is performed manually. | Member Registries use standardized contact data to alleviate postal delivery failures. | Member Registry is federated with RHIOs. |
| Responses are inconsistent and manual. | MITA standard interfaces are used by Medicaid agency and collaborating sister agencies. | Public health alerts can be triggered by clinical information in the patient's electronic health record. |
| There may be delays in responses. | Routine requests from members are standardized and automated within the agency via AVRS, Web portal, EDI | Turnaround time is immediate, on a national scale. |
| Complies with agency goals and expectations. | Research and response for these standardized communications are immediate or within batch response parameters. | Member Registries are federated with regional data exchange networks across the country and if desired, internationally. |
| Requires signification labor force. | Responses are consistent and timely. | Responses are standardized and can include clinical data |
| Manual and semi-automated steps may require some days to complete response. | Requires fewer staff. | Responses are standardized and can include clinical data |
| Responses are made manually and there may be inconsistency and inaccuracy (within agency tolerance level). | Member requests and responses are automated via Web, AVRS, EDI with data stamp and audit trail. | Responses are immediately available. |
| Staff research and respond to requests manually. | Inquiries can be made to multiple agencies via collaboration. | Automated access to information nationally improves efficiency. |
| Requires research staff. | Response can be immediate . | Full automation or the process plus access to clinical data, on a national scale, reduces staff requirements to a core team of professionals who monitor member satisfaction with responsiveness to inquiries. |
| Responses are manually validated | Automated responses increase accuracy. | Incorporation of clinical data, on a national scale, improves accuracy of some responses |
| Process complies with agency requirements | Access is via Web portal and EDI channels. | Some inquiries/responses are replaced by automated messaging on a national scale. |
| Members receive the information they needed | Requests and responses are standardized nationally, improving accuracy. Member information is accessed via either a single Member Registry or federated Member Registries. Member information belonging to different entities can be virtually consolidated to form a single view. Responses lo member requests are automated. Fewer staff required to support. Information requested by member is continuously refreshed. Collaboration among agencies achieves a one-stop shop for member inquiries. Automation leads to fewer staff. Number of responses per day- increases significantly. Collaboration and shared services increase cost effectiveness. Automation improves accuracy of responses. MITA standard interfaces improves requests and responses | |

TABLE 60-continued

Global Health and Life Sciences High Performance
Capability Assessment Model - Public Health Services - Medicaid
Member Management

| Basic | Sub-Platform: Prospective and Current Member Support Competitive | Capability: Manage Applicant and Member Communication Market Leading |
|---|---|---|
| | nationally. Members have no delay obtaining responses. Members have a one stop shop to access collaborating agencies to obtain information. | |

TABLE 61

Global Heallh and Life Sciences High Performance
Capability- Assessment Model - Public Heallh Services - Medicaid
Member Management

| | Sub-Platform: Prospective and Current Member Support | Capability: Manage Customer Relationships |
|---|---|---|
| Basic | Competitive | Market Leading |
| 9.4.4.1 Manage Quality and Performance of the Customer Relationship Management Process Handle Member Profile Calls Escalate & Follow-up on Inquiries Handle Misdirected Calls 9.4.4.2 Manage member relations | | |

TABLE 62

Global Health and Life Sciences High Performance
Capability Assessment Model - Public Health Services - Medicaid
Member Management

| | Sub-Platform: Prospective and Current Member Support | Capability: Manage Member Grievance and Appeal |
|---|---|---|
| Basic | Competitive | Market Leading |
| 9.4.2.1 Receive grievance or appeal 9.4.2.2 Request additional documentation as appropriate 9.4.2.3 Determine grievance or appeal status (initial, second, or expedited) 9.4.2.4 Triage to appropriate personnel for review 9.4.2.5 Schedule and conduct hearing within required time 9.4.2.6 Determine disposition 9.4.2.7 Request preparation of a formal disposition to be sent to applicant member | | |

TABLE 63

Global Health and Life Sciences High Performance
Capability Assessment Model - Public Health Services - Medicaid
Member Management

| | Sub-Platform: Prospective and Current Member Support | Capability: Perform Population and Member Outreach |
|---|---|---|
| Basic | Competitive | Market Leading |
| Business process is uncoordinated among multiple, siloed programs and not systematically triggered by agency-wide processes. | The business process is organized around the "no wrong door" concept. | At this level, the business process is national in scope, based on analysis of clinical, demographic, and socioeconomic indicators and shared among Medicaids and other public programs |
| Outreach is primarily manual and conducted by paper or phone. | States use Websites, Agencies use TV, radio and advertisements to distribute outreach information to targeted members | Outreach triggers are event driven. |
| Outreach materials are manually prepared and updated. | Agencies support deployment of internet access points. | Peer2peer business process collaboration between the Agency and EHRs or other program applications. |
| Identification of targeted members is based primarily on member records and limited to current program information. | The business process is primarily electronic, with paper used only secondarily. | Access to standardized electronic clinical data facilitates identification of and may trigger electronic messages to members in need of outreach and/or education. |
| Outreach to prospective members is sporadic and lacks analysis needed for targeting specific populations. | Use of electronic communications makes production of appropriate outreach material more feasible and cost-effective. | Coordinated outreach and education can be regional and Pan-Medicaid in scope. |

TABLE 63-continued

Global Health and Life Sciences High Performance
Capability Assessment Model - Public Health Services - Medicaid
Member Management

| Sub-Platform: Prospective and Current Member Support | | Capability: Perform Population and Member Outreach |
|---|---|---|
| Basic | Competitive | Market Leading |
| Current and prospective members have difficulty locating needed information because of siloed programs. | Access to standardized electronic clinical data as well as use of GIS and socio-economic indicators support targeting populations for outreach. | Outreach material are automatically generated and sent to members in response to requests made via email or PHRs, or by scheduled release. |
| Education materials are lacking because difficult and costly to produce. | Shortened time for materials to reach the members. | Staff focuses on maintaining a data base of functionally, linguistically, culturally, and competency appropriate outreach and education materials. |
| Quality and consistency of outreach and education efforts are difficult to maintain. | Member registries use standardized contact data | Triggers create messages from members' EHRs/PHRs that map to automated response messages. |
| Primarily an all manual process. | Members are able to access information regardless of their channel of inquiry. | Turnaround time for sending appropriate information is immediate on a national or regional scale. |
| Members must wait in phone queue to make inquiries and may have to contact multiple programs to access the needed information. | Outreach materials are developed and stored in electronic format and made available to members via a Web portal, public media, or kiosks. | Turnaround time to identify target member and transmit information is immediate. |
| Mailings take a number of days to produce and send. | Outreach and education materials are available via state Medicaid portal and are shared with other collaborating agencies. | Nearly eliminates time current and prospective members must spend discovering and submitting needed information to all social services. |
| Due to lack of electronic sources or outreach and education materials, current and prospective members must spend a great deal of time discovering needed information. | Access to electronic sources or outreach and education materials greatly reduces time that current and prospective members must spend discovering needed information. | Access to standardized clinical data facilitates identification of targeted current and prospective members. |
| Preparation of materials is clunky. Information is subject to inaccuracies and inconsistencies. | Automation improves access and accuracy. | Standardized services support application interfaces for electronic interchange of outreach and education material to targeted . . . |
| Lack of functionally, linguistically, culturally, and competency appropriate outreach and education materials likely limit members' access to information | Current and prospective members can access needed information via Web portal. | Outreach and education materials can be effectively pushed on an as needed basis because of standardized data used by Member Registries nationally. |
| Mailings are not delivered because contract data in members' records do not meet NPS standards. | Increased standardization of administrative data, and improved data manipulation for decision support improves accuracy of populating targeting | Standardized business process collaboration protocols support application interfaces for peer2peer outreach and education processes. |
| Staff develops and maintains materials manually | Increasing use of functionally, linguistically, culturally, and competency appropriate outreach and education materials improve members' access to information | Access to clinical information improves efficiency by automatically mapping member who needs assistance with generation of appropriate materials. |
| Developing functionally, linguistically, culturally, and competency appropriate outreach and education materials is difficult. | Member information is accessed via federated Member Registries that can be accessed by all authorized entities within the state. | Automated business rules that include clinical data lead to faster identification of target populations. |
| Effort is required to research target current and prospective target populations and track mailings. | Algorithmic identification of and analysis based on standardized data to targeted members improve in accuracy. | Outreach and education materials can be effectively pushed on an as needed basis regionally or nationally via federated Member Registries. |

TABLE 63-continued

Global Health and Life Sciences High Performance
Capability Assessment Model - Public Health Services - Medicaid
Member Management Sub-Platform: Prospective and Current Member Support Capability: Perform Population and Member Outreach

| Basic | Competitive | Market Leading |
|---|---|---|
| Mailings are not delivered because of inaccurate, nonstandard contact information, resulting in need to follow up with members by other means or missing outreach and education opportunities. | Use of NPS standards for member data improves accuracy for mailing purposes. | The target population analysis is based on real time access to health and socioeconomic indicators drawn from standardized person/patient data |
| Process is labor-intensive. | Populations are targeted more effectively because programs are able to share member analysis. | Full automation of the process of identification of need, mapping to the right message, plus access to clinical data reduces staff requirements to a core team of professionals who monitor the education and outreach process. |
| Paper materials are expensive to produce. | Materials can be posted on a Web site for downloading by members. | Outreach and education can be interoperable among states sharing business services, reducing redundant effort and optimizing delivery of appropriate needed material real time to the point of care. |
| Incurs postal expenses and cost of undelivered mail. | Fewer staff required to support. | Incorporation of clinical data improves accuracy of identification of targeted members and dissemination of appropriate messages. |
| Staff still needed where the materials are not appropriate for member. | Delivery of appropriate outreach and education materials is eased with electronic and public media channels. | Member registries improve accuracy of contact information. |
| Difficult to determine impact of outreach and education. | National standards are developed for creation education and outreach materials. | Access to member information on a regional or national basis. |
| Current and prospective members continue to need assistance by phone. | Business services are developed and shared nationally to support target population identification. | Outreach and education communications can be triggered by automated messaging. |
| Business process complies with agency and state requirements for educating the members regarding rules and regulations and how to communicate with the Agency. | Mailings are more successful because member records have NPS standard data and member registries1 use algorithmic identification to improve data accuracy. | Use of clinical evidence creates better target groups and improves consistency of results |
| | Automation reduces level of staffing required to target populations needing outreach and education. | Access to member information on a regional or national basis. |
| | Availability of online materials reduces paper and mailing costs. | |
| | Collaboration, data sharing, and shared services increase cost-effectiveness. | |
| | NPS standard member contact information decreases undelivered mailings. | |
| | Use of portal by members is monitored to ensure that a sufficient number of the targeted populations are actively engaged in downloading information. | |
| | Agency can target members who are not accessing informatioa | |
| | Business services standardize messages sent to members. | |
| | The members and the agency benefit from introduction of automation to speed up the | |

TABLE 63-continued

Global Health and Life Sciences High Performance
Capability Assessment Model - Public Health Services - Medicaid
Member Management

| Sub-Platform: Prospective and Current Member Support | | Capability: Perform Population and Member Outreach | |
|---|---|---|
| Basic | Competitive | Market Leading |
| | outreach and education process. Agencies benefit from sharing of the business service and information with other agencies. Members benefit from consistency and timeliness of the information transmitted | |

TABLE 64

Global Health and Life Sciences High Performance
Capability Assessment Model - Public Health Services - Medicaid
Operations Management

| Sub-Platform: Service Authorization | | Capability: Authorize Referral |
|---|---|---|
| Basic | Competitive | Market Leading |
| At this level, the Authorize Referral Request process is performed primarily using a paper/phone/fax process. | At this level, the Authorize Referral process transaction, receives only EDI transactions via electronic means that support even small, rural, and waiver providers. | The process queries national and regional registries for pointers to repositories of member's clinical data and provider credentialing and sanction data for prospective program integrity audits. |
| Review of authorization requests are performed manually which is resource intensive, untimely and may result in inconsistent: Application of business rules | Web portal support error free submissions with data field masks, client-side edits, and pre-populated fields. | Meta-data is used to locate the records and to ensure semantic inoperability of the data even where the data may be based on different coding schemes or data models. |
| Review of authorization requests are performed manually which is resource intensive, untimely and may result in inconsistent: Communication of errors to providers | The service requests may be accepted by internet Web portals, email, dial-up, and via transferable electronic media such as disks and tape. | Inter-enterprise business process management between Medicaid systems and Clinical data during an episode of care eliminates the need for providers to submit referral data |
| Review of authorization requests are performed manually which is resource intensive, untimely and may result in inconsistent: Decisions on the need for or sufficiency of additional information | If a referral data set fails review, rather than the reviewer having to manually contact the submitter, the process can now generate an electronic request for additional information via an XI2 277. | Real-time access to source data ensures accuracy and improved process performance. |
| If the referral request requires additional information, the reviewer must manually contact the submitter/provider, which delays processing and is resource intensive. | Standardized data enable tracking overutilization of similar services that are coded differently for prospective program integrity and tracking contraindication of services provided for medical appropriateness. | Member and provider data accessible in regional registries are recognized by all participating applications as the "source of truth". |
| Format and content is not HIPAA compliant, and is likely state-specific. | | Service referrals no longer need to be checked because business rules alert the provider about clinical prerequisites for service coverage. MCO use of service authorization can be monitored for underutilizations by review of the encounter data. |
| The service requests are primarily manually validated against state-specific business rules. However, when there is automated validation, rules lack flexibility. | | There are established RHIOs and semantic interoperability. |

TABLE 65

Global Health and Life Sciences High Performance
Capability Assessment Model - Public Health Services - Medicaid
Operations Management Sub-Platform: Service Authorization  Capability: Authorize Service

| Basic | Competitive | Market Leading |
|---|---|---|
| Authorize Service request is primarily paper, phone or faxbased. Format and content are not H1PAA compliant. | The Agency receives EDI transactions via electronic means that support even small, rural, and waiver providers | Service authorization is embedded in the provider to payer system communication. As the provider enters service data into the CLINICAL DATA, authorization is immediately established by the payer application. |
| Each state has developed many paper forms to support this process. Information is manually validated and manually transferred from submitted paper to the MM IS. | Web portals support error free submissions with data field masks, client-side edits, and pre-populated fields. | Capabilities are expanded to a national base of data via NHIN. |
| If a Authorize Service request requires additional information, the reviewer must manually contact the submitter/provider, which delays processing and is resource intensive. | Processes generate an electronic request for additional information via an X12277 if additional information is required. | The Medicaid agency and providers establish pointers to national repositories of member's clinical data Direct access to Clinical data eliminates the need for additional information within the Authorize Service process. |
| Authorize Service requests are primarily manually validated against statespecific business rules. | The process is completely automated and only rare exceptions must be manually reviewed. | Meta-data is used to locate the records and to ensure semantic interoperability of the data even where the data may be based on different coding schemes or data models. |
| Inflexibility in Authorize Service processing is a key factor in the proliferation or siloed systems outside of the MMIS. | Processing is highly flexible so that rule changes can be made quickly and inexpensively in response to need for new or different rules | This data takes the form of virtual records used to inform the Authorize Service process. |
| Especially for waiver programs that determine medical appropriateness and service authorization differently than traditional Medicaid programs | The process uses complex algorithms and the application of structured clinical data allowing for high automation. | The process is an inter-enterprise business process between Medicaid systems and Clinical data during an episode of care. |
| | All programs use semantically interoperable data in the process. | Through peer-lo-peer collaboration, the CLINICAL DATA assists the provider with Medicaid clinical protocols required for coverage. |
| | Standardized data and Authorize Service rules enable tracking of overutilization of similar services that are coded differently | There are established RHIOs and semantic interoperability |
| | Related processes are decoupled, allowing changes to be made in the Authorize Service process with reduced potential for unintended downstream processing consequences. | |

TABLE 66

Global Health and Life Sciences High Performance
Capability Assessment Model - Public Health Services - Medicaid
Operations Management Sub-Platform: Service Authorization  Capability: Authorize Treatment Plan

| Basic | Competitive | Market Leading |
|---|---|---|
| The Authorize Treatment Plan process is performed primarily using a paper/phone/fax process. | The process is a mix of paper/phone/fax and EDI. The authorize treatment plan requests may be accepted by internet Web portals, email, dial-up, and via transferable electronic media such as disks and tape. | The process is simplified querying national and regional registries for pointer to repositories of member's EHRs for clinical data and provider credentialing and sanction data for prospective program integrity audits. |

TABLE 66-continued

Global Health and Life Sciences High Performance
Capability Assessment Model - Public Health Services - Medicaid
Operations Management

| Sub-Platform: Service Authorization | | Capability: Authorize Treatment Plan |
|---|---|---|
| Basic | Competitive | Market Leading |
| Review of authorization of treatment plan requests are performed manually. | The Web portals support error free submission with data field masks, client-side edits, and pre-populated fields. | Meta-data is used to locate the records and to ensure semantic interoperability of the data even where the data may be based on different coding schemes or data models. |
| If the treatment plan request requires additional information, the reviewer must manually contact the submitter/provider. | If a treatment plan data set fails review, rather than the reviewer having to manually contact the submitter, the process can now generate an electronic request for additional information via an X12 277. | Interenterprise business process management between Medicaid systems and Clinical data during an episode of care eliminates the need for providers to submit treatment plan data |
| Format and content is not standardized and is likely state-specific. | Standardized data enable tracking of over-utilization of similar services that are coded differently for prospective program integrity and tracking contraindication of services provided for medical appropriateness. | Real-time access to source data ensures accuracy and improves process performance. |
| The requests are primarily manually validated against state-specific business rules. | | Member and provider data accessible in regional registries are recognized by all participating applications as the "source of truth". |
| When there is automated validation, rules lack flexibility and are costly to change. | | Treatment plans for claims no longer needs to be checked because Medicaid business rules alert the provider about clinical prerequisites for service coverage |
| Related processes are tightly integrated, making it difficult to ensure that changes to service authorization process do not result in unintended crossprocess consequences. Maintenance is expensive and time-consuming. | | There are established RHIOs and semantic interoperability. |

TABLE 67

Global Health and Life Sciences High Performance
Capability Assessment Model - Public Health Services - Medicaid
Operations Management

| Sub-Platform: Member Payment Information | | Capability: Calculate Spend-Down Amount |
|---|---|---|
| Basic | Competitive | Market Leading |
| The Calculate Spend-Down Amount business process is primarily paper based. An applicant's costs for health services are tracked by adding paper bills and receipts until the spend-down amount for each period is met | The business process is conducted electronically and does not require that members report their costs. | Providers enter new service information into clinical records at various locations if a client is flagged as a candidate. |
| Applicants may be required to submit a paper spend-down report | Members are made eligible for Medicaid coverage with a deductible amount equal to their spenddown requirements for the specified period. | |
| Stall applies spend down rules to decide whether the submitted costs are allowable and in which period to apply the costs, sometimes resulting in inconsistent determinations or controversy with the applicant. | Applicants submit electronic spend-down reports, and either scan, fax, or mail health care bills and receipts. | |

TABLE 67-continued

Global Health and Life Sciences High Performance
Capability Assessment Model - Public Health Services - Medicaid
Operations Management
Sub-Platform: Member Payment Information   Capability: Calculate Spend-Down Amount

| Basic | Competitive | Market Leading |
|---|---|---|
| If spend-down is met, staff keys change in eligibility status into the applicant's record so that subsequent claims will pay for a specified period. | Agencies support transmission of spend down information on the X12 270-271. | |
| | Providers are able to determine the spend-down amount when they verify eligibility. The member's account accumulator automatically accounts for excess resources during claims processing by debiting the amount paid by the member Once spend-down has been met. Medicaid payments to begin and/or resume. | |

TABLE 68

Global Health and Life Sciences High Performance
Capability Assessment Model - Public Health Services - Medicaid
Operations Management

| Sub-Platform: Member Payment Information | | Capability: Prepare Member Premium Invoice | |
|---|---|---|---|
| Basic | Competitive | | Market Leading |
| The agency uses manual procedures to maintain member accounting for premium invoicing and payment. | Information from all program eligibility systems is used to establish the amount of the member liability in a centralized member accounting system associated with the Member Registry. | | |
| The agency uses manual procedures to maintain transaction history of all monies received or paid out of the member account | Member liability amounts are updated by MMIS with online adjustment capability. | | |
| The agency uses manual procedures to reimburse members for HIP payments; and support member contribution accumulators to determine out of pocket maximums or spend down requirements. | The process creates a debit when payments are made, overpayments are credited to the account and refunds made to the member by check, EBT. | | |
| Member liability records are siloed by program and based on program specific eligibility records. | Notices automatically are sent to the member from a central enterprise-wide member communications management business area. | | |
| Invoicing and payment receipt are manual processes requiring data entry for payment processing and for the changes in member liability due to eligibility status. | Member cost sharing accounts are maintained and updated by claims or member direct premium or pay in payments activity. | | |
| Member accounting may be program specific, resulting in members receiving invoices and reimbursement from, and making premium payments to different parts of the Agency. | Total payments are automatically compared to the member's benefit package requirement for out of pocket expenses. | | |

TABLE 68-continued

Global Health and Life Sciences High Performance
Capability Assessment Model - Public Health Services - Medicaid
Operations Management

| Sub-Platform: Member Payment Information | | Capability: Prepare Member Premium Invoice |
|---|---|---|
| Basic | Competitive | Market Leading |
| Total payments are manually compared to the member's benefit package requirement for out of pocket expenses. Notices are manually generated and sent on paper to members advising them of their hearing rights and the amount of their contribution. | Payments can be accepted at all Agency sites. Payment can be in the form of cash, check, or credit or debt card. Details of the transaction are posted to the member accounting modules on the MMIS and then sent to the Agency financial systems. | |

TABLE 69

Global Health and Life Sciences High Performance
Capability Assessment Model - Public Health Services - Medicaid
Operations Management

| Sub-Platform: Claims/Encounters Adjudications | | Capability: Apply Claim Attachment |
|---|---|---|
| Basic | Competitive | Market Leading |
| Paper claims attachments are sent separately from the claim; the two documents are matched up, requiring some manual intervention | The agency receives a mix of paper and electronic attachments. Electronic attachments are automatically matched to corresponding claim. | Attachments are no longer required because the payer has direct access to the clinical data stored in the clinical data record. |
| There are limited, agencyspecific requirements for the attachments. Medical records are delivered in paper format with no standards. | Electronic attachments meet HIPAA standards and MITA standard interface requirements with agency-specific Implementation Guide instructions. Some manual processing is still required. | Through the NHIN, the Medicaid agency can view clinical data stored in Clinical data in any location in the country. |
| Claims requiring attachments are subject to delays. | Electronic attachments are required for electronically submitted claims. | Clinical information needed for adjudicating payment for a service is instantly accessed (including nationally). |
| Manual matches and reviews result in inconsistency and errors. | Agency continues to accept paper attachments from a small number of disadvantaged providers who still submit paper claims | Access is immediate, with data available nationally. |
| Labor-intensive, requires professional review staff. | Electronic attachments shorten time required to match with claim and edit. | Accuracy increases based on direct access to source clinical data, no translation. |
| Costly, but meets agency goals for ensuring appropriateness of payment. | Use of MITA national standards for claims attachments increases speed of processing. | No human intervention is required on a national scale, therefore, maximum efficiency. |
| There are inconsistencies in results in the manual matching and processing of attachments. | Electronic attachments increase accuracy State complies with HIPAA standards but also has its own IG requirements. Electronic attachments are required for electronic claims and a MITA national standard is used. This increases access and accuracy of data Electronic attachments reduce staff requirements. More managed care enrollment means fewer claims/attachments. Use of MITA national standards for the Claim Attachment facilitates performance. Accuracy is improved | Maximum accuracy |

TABLE 70

Global Health and Life Sciences High Performance
Capability Assessment Model - Public Health Services - Medicaid
Operations Management

| Basic | Sub-Platform:<br>Claims/Encounters Adjudications<br>Competitive | Capability:<br>Apply Mass Adjustment<br>Market Leading |
|---|---|---|
| The agency identifies the claims to be adjusted, sets the parameters, and applies the retroactive rates through primarily manual processes. | Improvements throughout the Medicaid program operations reduce the number of mass adjustments required.<br><br>Identification of claims to be adjusted and application of the adjustment are automated with audit trail.<br>Adjustment data is specific to the agency.<br>MITA standard interfaces for mass adjustments are used by the state Medicaid agency. | |

TABLE 71

Global Health and Life Sciences High Performance
Capability Assessment Model - Public Health Services - Medicaid
Operations Management

| Basic | Sub-Platform:<br>Claims/Encounters Adjudications<br>Competitive | Capability:<br>Audit Claim-Encounter<br>Market Leading |
|---|---|---|
| The agency recieves paper claims, EDI transactions, and POS conforming to state standards. | The agency continues to accept paper claims from a small number of disadvantaged providers, but the majority of transactions are submitted electronically. | Direct connection between Medicaid systems and providers' Clinical data during an episode of care eliminates the need for providers to submit claim data or attachments requiring editing. |
| Paper transactions are batched and scanned (or data entered). | Electronic transactions meet HIPAA data standards. | Through peer-to-peer collaboration, member and provider data accessible in regional registries are recognized by all participating applications as the "source of truth". |
| State-specified data elements trigger the Edit and Audit Claim/Encounter business process. | Electronic transactions meet MITA data standards. | The process queries national and regional registries for member and provider information. |
| Encounter data is recieved via tape in state-specified format and data content.<br>Sister agencies and waiver programs manage their own Edit and Audit Claim process. | Payer-specific implementation Guides are replaced by MITA standards.<br>Translators convert national data standards to statespecific data to support business processes. | The process is able to locate and query the members' Clinical data to validate health status data.<br>The Edit process can rely on the real-time updates to the Reference Repository from authoritative sources for definitive coding schemes. |
| Payer implementation Guides impose additional payer-specific rules. | The business process uses MITA standard data and therefore no translation is required. | The process can locate members' primary payers' benefit repository to access services covered under each third-party resource. |
| Suspend claims require lengthy manual resolution. | Encounters are submitted as HIPAA compliant COB claims from managed care organizations and any other external processor. | There are established RHIOs and semantic interoperability. |
| Data are not comparable across silos. | Encounter data meets MITA standard interface requirements. | Real-time access to source data ensures accuracy and improves process performance. |
| For EDI claims/encounters edits are automated for many steps, but are manual for attachments and suspended claims/encounters:<br>Claims/encounters EDI format and content is not HIPAA compliant. | Medicaid agency coordinates with other sister agencies and waivers programs to accept, process, and access MITA standard data elements. | Real-time access to source data enables enhanced business activity monitoring is baesd on optimal data streams to fine-tune business process rules to meet operational parameters, thereby ensuring that Agency objectives are met. |

TABLE 71-continued

Global Health and Life Sciences High Performance
Capability Assessment Model - Public Health Services - Medicaid
Operations Management

| Sub-Platform: Claims/Encounters Adjudications | | Capability: Audit Claim-Encounter |
|---|---|---|
| Basic | Competitive | Market Leading |
| Attachment data is unstructured It is difficult for reviewers to consistently interpret and apply adjudication rules. | Electronic claim processing and POS adjudication greatly increase timeliness. | Access to additional data form national sources adds to accuracy of editing. |
| For EDI claims/encounters, edits are automated for many steps, but are manual for attachments and suspended claims/encounters. | Waiver claims continue to be submitted to siloed payment systems using state specific format and data, such as provider type and service codes. | Claim processing is replaced by direct communication between provider system and payer system. |
| COB is conducted by denying claims using the resource intensive payer-toprovider model. | All programs, even those not covered under HIPAA, use semantically interoperable data in the edit prcess. | All claims for members with known third-party's resources are flagged for payer-to-payer COB, reducing provider burden and improving thre timelines of reimbursement. |
| Edited fields are validated against standard and state specific code sets. | If a claim/encounter data set fails edit validation, the process can now generate an electronic request for corrections via an X12 276. If additional information is required, an electronic request is made, e.g., via an X12 277. | Related processes are decoupled, allowing changes to be made in the Edit/Encounter process with reduced potential for unintended downstream processing consequences. |
| Maintenance is expensive and time-consuming. | Standardized data and edit rules enable tracking of overutilization of similar services that are coded differently for disallowance. | The process is completely automated and only rare edit exceptions must be manually reviewed. Optimizing automation improves error rates and timeliness, thereby enabling support of real-time claims/encounter processing. |
| Rules lack flexibility and are costly to change. Therefore, when new programs, code sets, or edits are added, claims/ encounters with these changes may need to be edited manually, which may not be cost effective in the long term. | All siloed payment systems are integrated or retired, saving resources and optimizing FFP, and data quality is improved. | |
| Results meet agency requirements for timeliness and accuracy. | Edit processing is highly flexible so that edit rules and code set of changes can be made quickly and inexpensively. Edit rules engines support complex algorithems so that benefit packages can be customized for members eligible for multiple programs Edits can be structured for both traditional and waiver programs Maintenance continues to be expensive and timeconsuming Despite progress, related processing continue to be tightly integrated, so that changes to edit can result in unintended downstream processing | |

TABLE 72

Global Health and Life Sciences High Performance
Capability Assessment Model - Public Health Services - Medicaid
Operations Management

| Sub-Platform: Claims/Encounters Adjudications | | Capability: Price Claim-Value Encounter |
|---|---|---|
| Basic | Competitive | Market Leading |
| Standard Medicaid services are automatically priced using rate and fee reference data. Values are assigned to services reported on encounters, using the same reference data. | More services are automatically priced and there are fewer "by-report" manual pricing exceptions. | Pricing is embedded in the provider to payer system communication. As the provider enters service data into the clinical record, authorization and pricing are immediately established by the payer application. |
| "By-report" pricing is performed manually. | Medicaid agency coordinates with sister agencies and waiver programs to present a one-stop shop claim adjudication and pricing process. | The agency uses the NHIN to compare and select prices based on regional averages or other new pricing methodologies (TBD). |
| Staff manually prepare adjustment transactions including application of member contributions, provider advances, deduction of liens and recoupments. | Most single claim adjustments are automated. | Supports regional pricing profiles that can be factored into the pricing methodology. |
| Waiver program and a-typical provider services are manually priced. | State Medicaid agency can support payment of waiver program and a-typical providers. | For example, a new pricing rule: "Pay the amount billed or the regional average (Region = ME, NY, VT), whichever is lower"... or, "Pay the regional per diem no matter what is billed". |
| | The agency uses MITA standard interfaces to price claims and value encounters. Flexible business rules allow maximum flexibility in changing pricing algorithms. Pricing formulas are agency specific. | |

TABLE 73

Global Health and Life Sciences High Performance
Capability Assessment Model - Public Health Services - Medicaid
Operations Management

| Sub-Platform: Cost Avoidance | Capability: Perform Cost Avoidance Functions | |
|---|---|---|
| Basic | Competitive | Market Leading |
| 10.8.1.1 Identify and verify other insurance/third party resource information according to clams received 10.8.1.2 Send collection letters to other responsible parties for payment due to Medicaid 10.8.1.3 Provide and process reports to monitor cost avoidance effort | | |

TABLE 74

Global Health and Life Sciences High Performance Capability Assessment
Model - Public Health Services - Medicaid
Operations Management

| Sub-Platform: Cost Recoveries | | Capability: Manage Drug Rebate |
|---|---|---|
| Basic | Competitive | Market Leading |
| At this level, the business process is primarily paper invoice processing. | The business process uses electronic interchange and automated processes to support | Drug rebate is replaced by a new strategy where care management and disease management interact |

TABLE 74-continued

Global Health and Life Sciences High Performance Capability Assessment
Model - Public Health Services - Medicaid
Operations Management

| Sub-Platform: Cost Recoveries | | Capability: Manage Drug Rebate |
|---|---|---|
| Basic | Competitive | Market Leading |
| | state generation of rebate information. | with provider EHRs. |
| Rebate information is manually validated. | The business process uses MITA standard interfaces. | Data exchange is on a national scale. |
| Programs are siloed so rebate process may be uncoordinated and shared programs with health departments pay for drugs but may not participate in the state drug rebate program. | Agencies centralize drug utilization data from siloed programs as inputs to the drug rebate process. | Through peer-to-peer collaboration, real-time access to source data ensures accuracy, eliminates redundant collection and interchange of data, and improves process performance. |
| Non-standardized data and format makes any type of cross program management reporting and analysis for drug rebate purposes is difficult and costly. | Data is standardized for automated electronic interchanges (interfaces) between agencies and drug manufacturers. | |
| Access to data is limited by legacy systems and CMS reporting cycles | Communications are more consistent, timely and appropriate. | |
| Reporting, analysis, and responses to inquiries are not timely and data may not be accurate. | | |
| Cost-effectiveness is impacted by lack of data accuracy and completeness, manual processing, and need for CMS quarterly reporting of rebate information. | | |

TABLE 75

Global Health and Life Sciences High Performance Capability Assessment
Model - Public Health Services - Medicaid
Operations Management

| Sub-Platform: Cost Recoveries | | Capability: Manage Estate Recovery |
|---|---|---|
| Basic | Competitive | Market Leading |
| At this level, the business process is primarily a mix of paper, phone, fax and proprietary EDI. | The business process has almost eliminated its use of nonelectronic interchange and has automated most processes to the extent feasible. | The data exchange necessary for estate recovery is accessed for member and third party resources on a national scale. |
| Nonstandardized data and format from multiple sources requires manual compilation of data. | Agencies are standardizing data to increase coordination and consistency. | Through peer-to-peer collaboration between the agency and provider EHRs or other program applications. |
| Access to data is limited by the sporadic, inconsistent, and untimely receipt of data and updates to member eligibility. | MITA standard interfaces are used for electronic interchanges (interfaces) between agencies. | e.g.. For example, health departments for date of death matches, realtime access to source data ensures accuracy, eliminates redundant collection and interchange of data and improves performance. |
| Generating correspondence is not timely. | Communications to stakeholders and member's personal representatives are consistent, timely and appropriate. | |
| Cost effectiveness is impacted by lack of data accuracy and completeness, and manual processing. | | |

TABLE 76

Global Health and Life Sciences High Performance Capability Assessment
Model - Public Health Services - Medicaid
Operations Management

| | Sub-Platform: Cost Recoveries | | Capability: Manage Recoupment |
|---|---|---|---|
| Basic | | Competitive | Market Leading |
| At this level, the process is likely primarily a manual process. | | The process has almost eliminated its use of nonelectronic interchange and has automated most processes to the extent feasible. | The process interfaces with other processes via federated architectures and collaborates with other processes in a peer2peer environment, eliminating redundant collection and interchange of data, and improving realtime, multi-axial processing. |
| Communications to providers and other payers are accomplished via phone and mail. | | More of the formatting is HIPAA compliant resulting in standardizing data to increase its usefulness for performance monitoring, management reporting, fraud detection, and reporting and analysis. | |
| Format is not HIPAA complaint, recouping of monies in third party liability situations is accomplished from payer to provider rather than payer to payer. | | There is more application-to-application communications which results in less manual intervention resulting in less maintenance and time savings. | |
| Non-standardized data makes any type of cross program performance monitoring, management reporting, fraud detection, or reporting and analysis difficult and costly. | | Data is standardized for automated electronic interchanges and interoperability. | |
| | | Communications to providers are consistent, timely and appropriate. | |

TABLE 77

Global Health and Life Sciences High Performance Capability Assessment
Model - Public Health Services - Medicaid
Operations Management

| | Sub-Platform: Cost Recoveries | | Capability: Manage Settlement |
|---|---|---|---|
| Basic | | Competitive | Market Leading |
| At this level, the business process is likely primarily paper based processing and some proprietary EDI. | | The business process has almost eliminated its use of nonelectronic interchange and has automated most processes to the extent feasible. | The business process interfaces with other processes via federated architectures and collaborates with other processes in a peer2peer environment, eliminating redundant collection and interchange of data. |
| Nonstandardized data makes any type of reporting and analysis difficult and costly. | | Data is standardized for automated electronic interchanges (interfaces). | The business process interfaces with other processes via federated architectures and collaborates with other processes in a peer-to-peer environment, improving realtime, multi-axial processing. |
| Programs create inconsistent rules across the Agency and Agencies apply their own rules inconsistently. | | Agencies centralize common processes to achieve economies of scale, increase coordination, improve rule application consistency, and standardizing data to increase its usefulness for performance monitoring, management reporting and analysis. | |

TABLE 78

Global Health and Life Sciences High Performance Capability Assessment
Model - Public Health Services - Medicaid
Operations Management

| | Sub-Platform: Cost Recoveries | | Capability: Manage TPL Recovery |
| --- | --- | --- | --- |
| Basic | | Competitive | Market Leading |
| The process is primarily a mix of paper, phone, fax and proprietary EDI. | | The process uses agency specified electronic interchange and automated processes. | COB is automatically coordinated through the RHIO registry. |
| Information regarding third-party resources is manually validated. | | The business process uses MITA standard interfaces for payer-to-payer COB process. | Data exchange for COB occurs on a national scale. |
| TPL recovery is accomplished primarily via paver-to-provider COB. | | Electronic or magnetic tape downloads from other agencies are used for data matches support access to member eligibility data. | Response and payment outcomes are immediate. |
| Inconsistency in the rules applied to TPL recoveries vary from agency to agency. | | Data is standardized for automated electronic interchanges (interfaces) between agencies and other payers. | Regional stakeholders are interoperable and payment determinations or denials are entirely a payer-to-payer process making the data immediate, accurate and consistent. |
| Programs are siloed so the recovery process may be uncoordinated. | | Communications are consistent, timely, and appropriate. | Through peer-to-peer collaboration, member and provider data is accessible through RHIO relays across the country. |
| Non-standardized data and format makes any type of cross program management reporting, and analysis difficult and costly. Access to data is limited by inter-agency and other payer legacy systems. Cost-effectiveness is impacted by lack of data accuracy and completeness, as well as inconsistency in how the rules and/or policies are applied to TPL recoveries, manual processing and timeliness. | | | |

TABLE 79

Global Health and Life Sciences High Performance Capability Assessment
Model - Public Health Services - Medicaid
Operations Management

| | Sub-Platform: Payment and Reporting Management | | Capability: Prepare COB |
| --- | --- | --- | --- |
| Basic | | Competitive | Market Leading |
| Medicaid agency identifies claims subject to COB prior to payment (Cost Avoidance) based on defined criteria. | | The agency uses MITA standard interfaces for claim adjudication and COB. The prepare COB process is completely automated and only in rare exceptions requires manual intervention. | The previous COB process is replaced by payer to payer communications. |
| The claim subject to COB is denied and returned to the provider indicating requirement to bill the primary payer first. | | Cost avoided claims are immediately forwarded to primary payers. Some claims are flagged manually for forwarding to a third party on an exception basis. | The agency can query registries across the country for pointers to repositories of member's third party resources. |
| Post payment recovery (Pay and Chase) claims are sent to third party payers using a mix of paper and EDI claims with non-standard data resulting in inconsistent application of rules, delays, and labor intensive efforts. | | Post payment recovery (Pay and Chase) claims are submitted to third party payers using MITA national standards. | Meta-data is used to locate the records and to ensure data interoperability. |

TABLE 79-continued

Global Health and Life Sciences High Performance Capability Assessment
Model - Public Health Services - Medicaid
Operations Management

| Basic | Sub-Platform: Payment and Reporting Management<br>Competitive | Capability:<br>Prepare COB<br>Market Leading |
|---|---|---|
| It is difficult to adapt to new policies for COB. COB processes are closely integrated with claims adjudication, pricing, and remittance advice, so changes affect all the interrelated processes.<br><br>Maintenance is expensive and time-consuming. | Flagging of post payment recovery claims is completely automated and only requires manual identification of recovery claims under limited circumstances. Optimizing automation improves error rates and timeliness of this process. Post payment recovery processing is highly flexible and supports complex algorithms. Related processes are decoupled, allowing changes to be made in the Prepare COB process with reduced impact on related business processes. All COB is coordinated among data sharing partner agencies in the state. | Real-time access to source data ensures accuracy and improves process performance. |

TABLE 80

Global Health and Life Sciences High Performance Capability Assessment
Model - Public Health Services - Medicaid
Operations Management

| Basic | Sub-Platform:<br>Payment and Reporting Management<br>Competitive | Capability:<br>Prepare EOP<br>Market Leading |
|---|---|---|
| Medicaid agency complies with federal regulations to produce random samples of EOMBs quarterly and mail to members. Members are asked to read the EOMB and report on any discrepancies.<br>Sensitive services are suppressed. | Medicaid agency enhances the sampling process to target selected populations.<br><br><br>Member responses are automatically tabulated.<br><br>Cultural and linguistic adaptations are introduced.<br><br>The agency uses MITA standard interfaces for the EOMB.<br><br>Other agencies collaborate with Medicaid in the EOMB process. | EOMB is replaced by a Personal Health Record.<br><br><br><br>Personal Health Records are accessible anywhere in the U.S. via the NHIN.<br>The agency has access to clinical data and can directly analyze services recorded and reported.<br>The agency can communicate with individuals who appear to need special attention. |

TABLE 81

Global Health and Life Sciences High Performance Capability Assessment
Model - Public Health Services - Medicaid
Operations Management

| Basic | Sub-Platform: Payment and Reporting Management<br>Competitive | Capability: Prepare Home and Community-Based Services Payment<br>Market Leading |
|---|---|---|
| The Prepare Home & Community-Based Services Payment business process is primarily paper/phone/fax based processing with limited EDI. | The Medicaid agency works with HCBS programs to share Medicaid processes. | HCBS programs benefit from payer system to provider system communications for immediate approval of payment. |

TABLE 81-continued

Global Health and Life Sciences High Performance Capability Assessment
Model - Public Health Services - Medicaid
Operations Management

| Basic | Sub-Platform: Payment and Reporting Management<br>Competitive | Capability: Prepare Home and Community-Based Services Payment<br>Market Leading |
|---|---|---|
| HCBS programs are separated and uncoordinated. There is no standardized data. | Medicaid agencies and sister agencies agree to use MITA standard interfaces for payment transactions. | Payments can be made anywhere in the U.S. |
| Payments are non-standard and cover a variety of atypical providers. Some payments are salary-based. | Some HCBS programs use Medicaid business processes for service authorization and service payment. | Payment authorization is embedded in the provider to payer system communication. As the provider enters service data into the clinical data record, authorization is immediately established by the payer application. |
| | HCBS providers agree to use Medicaid standards for price authorization and claims adjudication and payment. | |

TABLE 82

Global Health and Life Sciences High Performance Capability Assessment
Model - Public Health Services - Medicaid
Operations Management

| Basic | Sub-Platform: Payment and Reporting Management<br>Competitive | Capability: Prepare Premium EFT-Check<br>Market Leading |
|---|---|---|
| Medicaid agency or Department of Finance produces the EFT transaction or a paper check using Medicaid agency or state DOF standards for format and data content. | Medicaid agency complies with state or industry standards for EFT transactions and conforms with HIPAA where appropriate. | Payments are made directly to provider bank accounts triggered by entries into clinical records maintained by the provider and accessed by the payer. |
| | Agency encourages electronic billers to adopt EFT payment. | EFT payments are distributed to any location in the country via the NHIN. |
| | The agency uses MITA standard interfaces for EFT transactions Paper checks are produced where required for exceptional circumstances.<br>All electronic billers receive EFT payment.<br>Through inter-agency coordination, multiple agencies share the same EFT process. | Premium payments are made directly to MCO, insurance company. Medicare buy-in, et al bank accounts based on enrollment information. |

TABLE 83

Global Health and Life Sciences High Performance Capability Assessment
Model - Public Health Services - Medicaid
Operations Management

| Basic | Sub-Platform: Payment and Reporting Management<br>Competitive | Capability: Prepare Provider EFT-Check<br>Market Leading |
|---|---|---|
| Medicaid agency or Department of Finance produces the EFT transaction or a paper check using Medicaid agency or state DOF standards for format and data content. | Medicaid agency complies with state or industry standards for EFT transactions and conforms with HIPAA where appropriate. | Payments are made directly to provider bank accounts triggered by entries into clinical records maintained by the provider and accessed by the payer. |
| | Agency encourages electronic billers to adopt EFT payment. | EFT payments are distributed to any location in the country via the NHIN. |

TABLE 83-continued

Global Health and Life Sciences High Performance Capability Assessment
Model - Public Health Services - Medicaid
Operations Management

| Basic | Sub-Platform: Payment and Reporting Management<br>Competitive | Capability: Prepare Provider EFT-Check<br>Market Leading |
|---|---|---|
|  | The agency uses MITA standard interfaces for EFT transactions<br>Paper checks are produced where required for exceptional circumstances.<br>All electronic billers receive EFT payment.<br>Through inter-agency coordination, multiple agencies share the same EFT process. | Premium payments are made directly to MCO, insurance company, Medicare buy-in, et al bank accounts based on enrollment information. |

TABLE 84

Global Health and Life Sciences High Performance Capability Assessment
Model - Public Health Services - Medicaid
Operations Management

| Basic | Sub-Platform: Payment and Reporting Management<br>Competitive | Capability: Prepare Remittance Advice-Encounter Report<br>Market Leading |
|---|---|---|
| Medicaid agency produces the paper Remittance Advice using state Medicaid agency specific format and data content.<br>Explanations of codes are comprehensive and agency specific. | The Medicaid agency complies with HIPAA to supply an electronic RA that meets state agency Implementation Guide requirements.<br>The agency uses MITA standard interfaces for the RA. Paper RAs are still supported on an exception basis.<br>All electronic billers receive ERAs.<br>Through inter-agency coordination, multipleagencies can use the same ERA data standard. | With provider clinical system to payer system communication, the RA is replaced by a new accounting mechanism, (TBD).<br>Payment information can be sent to any location in the country via the NHIN. |

TABLE 85

Global Health and Life Sciences High Performance
Capability Assessment Model - Public Health Services - Medicaid
Operations Management

| Basic | Sub-Platform: Payment Information Management<br>Competitive | Capability: Inquire Payment Status<br>Market Leading |
|---|---|---|
| The claim status inquiry process is primarily a manual process and is associated with a specific service.<br>Providers inquire about the current adjudication status of a claim by phone, fax, or paper. Staff performs search on the claims history data store (for claims in process) or the claims history repository for claims that have been adjudicated. | Programs employ AVR, legacy direct data entry, and point of service devices for electronic claim status responses. Staff may still manually handle inquires that are not resolved with automated response.<br>The data uses agency standards and access is less timeconsuming, less burdensome, and requires fewer agency resources. | Claims processing is replaced by direct communication between the provider's CLINICAL DATA system and the payer system. Adjudication results are known immediately, eliminating the need for claim status inquires.<br>Inquiries can be launched and responded to nationally through the NHIN. |

TABLE 85-continued

Global Health and Life Sciences High Performance
Capability Assessment Model - Public Health Services - Medicaid
Operations Management Sub-Platform: Payment Information Management  Capability: Inquire Payment Status

| Basic | Competitive | Market Leading |
|---|---|---|
| Search may be based on the claim ICN, date of service, or patient name. Staff locates the data and relay it to the provider by phone, fax or paper. Process is timeconsuming for providers and resource intensive for agency. | All programs use a centralized automated electronic claim status process. Interfaces use MITA standards. Providers send HIPAAX12 276 or use online direct data entry and receive HIPAAX12 277 response or find the claim status online. Data is standardized; access is 24 x 7, and is completely automated for the provider. | Provider system collaborate with the MMIS during an episode of care. The providers' systems alert the provider to any clinical protocols and to any business rules required by the agency in order for the service to be paid.<br><br>When the episode of care has concluded, the service is reimbursed or not and the provider knows the payment status immediately, eliminating the need for payment status inquiry. |

TABLE 86

Global Health and Life Sciences High Performance
Capability Assessment Model - Public Health Services - Medicaid
Operations Management Sub-Platform: Payment Information Management  Capability: Manage Payment Information

| Basic | Competitive | Market Leading |
|---|---|---|
| At this level, the business process is focused primarily on meeting traditional FFS program needs as reflected in MMIS certification requirements. | The business process is now an enterprise resource that provides real time access to quality, complete and semantically interoperable data via record locator services that federate all programs' payment history. | The business process interfaces with external business processes via regional record locator services. |
| Data is largely nonstandardized and vary by siloed programs. | Data sources are primarily electronic interchange. | The business process collaborates with other processes in a peer2peer environment, eliminating redundant collection and interchange of data, and improving realtime, multi-axial processing. |
| Payment data is not timely. | All programs use HIPAA 837 data for claims history records. | Claims are no longer sent or compiled by the Agency, and instead, users of claims history data locate and compile clinical episode of care data within EHRs via record locator services or search engines on a real time, as need basis. |
| Data availability is limited by siloed systems' reporting capabilities. | Claims attachments are compliant with the X12 275. | Profiles of Medicaid enterprise payment history by member, provider, service or condition are accessible to authorized external users. |
| Using payment data for profiling members, providers, program analysis, or outcome measures requires costly and untimely statistical manipulation. | Premium payment data is compliant with the HIPAA 834. | Record locator services may be provided by semantic Web search engines. |
| | All payment history data is stored internally in accordance with a standards-based UML data model. | Emerging use of online publish and subscribe capabilities or other information content management capabilities enable push and pull of data to EHRs, PHRs and public health. |
| | Claims may be processed in real time, and automation of most adjudication and processes markedly improves the availability, quality, completeness and timeliness of payment data. | Applications pull and consume data available via URIs provided by semantic Web search engines. |

TABLE 86-continued

Global Health and Life Sciences High Performance
Capability Assessment Model - Public Health Services - Medicaid
Operations Management

| Sub-Platform: Payment Information Management | | Capability: Manage Payment Information |
|---|---|---|
| Basic | Competitive | Market Leading |
| | Decision support and sophisticated analytic tools enable users to compile member, provider, service or condition specific profiles and perform complex ad hoc analysis and reporting in real time. | |

TABLE 87

Global Health and Life Sciences High Performance
Capability Assessment Model - Public Health Services - Medicaid
Operations Management

| Sub-Platform: Capitation and Premium Payment | | Capability: Prepare Capitation Premium Payment |
|---|---|---|
| Basic | Competitive | Market Leading |
| The agency identifies members who have elected or have been auto-assigned to a managed care organization, a benefit manager, or a primary care physician, and matches them to appropriate rate cells, to calculate monthly payments. | The agency implements HIPAA-compliant standards for electronic premium payments, however, the other insurance companies impose their specific Implementation Guide requirements. | Payments are made directly to managed care bank account via RHIO registries. |
| Agency may use a modified claims adjudication process to support capitation payment preparation. | The agency uses MITA standard interfaces which incorporate HIPAA premium payment schema for identification of managed care program enrollees, and preparation of the capitation premium payments. | Agency can make premium payments to any managed care organization or insuring organization at any location in the country via the NHIN. |
| Adjustments are manually applied. | Business rules used to identify candidates are automated on a state-specific basis. | Clinical information is accessed directly from the MCO/PCP if the capitation payment is supplemented for special circumstances, e.g., high risk pregnancy. |
| These steps are mostly manual. | Some transactions continue to be manually processed at the request of the other insurer. | |
| Standards for the capitation payment transaction are agency-specific. | The agency has the flexibility to easily change the criteria for rate cells. | |

TABLE 88

Global Health and Life Sciences High Performance
Capability Assessment Model - Public Health Services - Medicaid
Operations Management

| Sub-Platform: Capitation and Premium Payment | | Capability: Prepare Health Insurance Premium |
|---|---|---|
| Basic | Competitive | Market Leading |
| The agency identifies members who meet criteria for buy-into other insurance coverage through primarily manual processes including a cost-benefit analysis of the individual case. | The agency implements HIPAA-compliant standards for electronic premium payments, however, the other insurance companies impose their specific implementation Guide requirements. | Payments are made directly to other insurer bank accounts via RHIO registries. |

TABLE 88-continued

Global Health and Life Sciences High Performance
Capability Assessment Model - Public Health Services - Medicaid
Operations Management Sub-Platform: Capitation and
Premium Payment — Capability: Prepare Health Insurance Premium

| Basic | Competitive | Market Leading |
|---|---|---|
| The agency enrolls the member and receives premium payment information. | The agency uses MITA standard interfaces for identification of candidates for other payer buy-in, analysis of cost/effectiveness, and health insurance premium payments. | Agency can make premium payments to any insurer at any location in the country via the NHIN. |
| The agency pays the premium according to the insurance company requirements. | Business rules to identify candidates and analyze cost/effectiveness are automated on a state-specific basis. | Access to clinical information helps to identify members eligible for other insurance programs. |
| These steps are mostly manual | Some transactions continue to be manually processed at the request of the other insurer. | |
| If there are no standards for these transactions. | The agency has the flexibility to easily change the criteria for identification of members eligible for other insurance buy-in. Medicaid collaborates with other payers to use the national standards. | |

TABLE 89

Global Health and Life Sciences High Performance
Capability Assessment Model - Public Health Services - Medicaid
Operations Management Sub-Platform: Capitation and
Premium Payment — Capability: Prepare Medicare Premium Payment

| Basic | Competitive | Market Leading |
|---|---|---|
| The agency identifies members who meet criteria for buy-in to Medicare Part B. | Medicaid agencies and CMS use a standard interface for the premium payment. The agency uses MITA standard interfaces for identification of candidates for Medicare Buyin. | Agency can verify status of buy-in candidate in other states and jurisdictions via the NHIN before generating the premium payment. |
| The agency exchanges information with the SSA using electronic communication standards specified by SSA. At this level, tape exchange is the primary medium. | Agencies use business rules to improve identification of buy-in candidates, prepare the premium payment calculation, and track the data exchange. | |
| The agency prepares the Medicare Part B premium buy-in report. | The agency has the flexibility to easily change the criteria for identification of buy-in candidates. The agency collaborates with other agencies to identify potential buy-ins. | |

TABLE 90

Global Health and Life Sciences High Performance
Capability Assessment Model - Public Health Services - Medicaid
Enterprise

| Sub-Platform: Health Informatics | | Capability: Develop Strategy |
|---|---|---|
| Basic | Competitive | Market Leading |
| 4.1.2.1 Determine Key Business Objectives | | |
| 4.1.2.2 Assess Current Business Environment against Market Evaluation | | |
| 4.1.2.3 Assess Current Technical Environment | | |
| 4.1.2.4 Define Organizational and Data Stewardship Needs | | |
| 4.1.2.5 Create Informatics Vision in alignment with overall Business Strategy | | |
| 4.1.2.6 Assess gaps between the current state environment and the Informatics Vision | | |
| 4.1.2.7 Define Informatics Capabilities and Impact | | |

TABLE 91

Global Health and Life Sciences High Performance
Capability Assessment Model - Public Health Services - Medicaid
Enterprise

| Sub-Platform: Health Informatics | | Capability: Execution of Strategic Direction and Activities |
|---|---|---|
| Basic | Competitive | Market Leading |
| 4.1.4.1 Perform Data Mining/Analysis | | |
| 4.1.4.2 Conduct Statistical Evaluation/Estimation | | |
| 4.1.4.3 Perform Predictive Modeling/Stratification | | |
| 4.1.4.4 Conduct Reporting (Outcomes/Forecast/Risks) | | |

TABLE 92

Global Health and Life Sciences High Performance
Capability Assessment Model - Public
Health Services - Medicaid
Enterprise

| Sub-Platform: Health Informatics | | Capability: Planning |
|---|---|---|
| Basic | Competitive | Market Leading |
| 4.1.1.1 Plan and Organize | | |
| 4.1.1.2 Collect Industry Research and Best Practices | | |
| 4.1.1.3 Gather Stakeholder Input | | |

TABLE 93

Global Health and Life Sciences High Performance
Capability Assessment Model-Public Health Services-Medicaid
Enterprise

| Sub-Platform: Health Informatics | | Capability: Prioritize Activities |
|---|---|---|
| Basic | Competitive | Market Leading |
| 4.1.3.1 Perform Cost Benefit Analysis and Financial Impact Estimation | | |
| 4.1.3.2 Determine Plan for Implementation of Capabilities | | |

TABLE 94

Global Health and Life Sciences High Performance
Capability Assessment Model - Public Health Services - Medicaid
Enterprise

| Sub-Platform: Procurement Management | | Capability: Internal Stakeholder Management |
|---|---|---|
| Basic | Competitive | Market Leading |
| 4.3.5.1 Performance Management | | |
| 4.3.5.2 Process & Contract Compliance | | |
| 4.3.5.3 Demand Management | | |
| 4.3.5.4 Customer Service Oriented | | |

TABLE 95

Global Health and Life Sciences High Performance
Capability Assessment Model-Public Health Services-Medicaid
Enterprise

| Sub-Platform: Procurement Management | | Capability: Requisition to Pay Operations |
|---|---|---|
| Basic | Competitive | Market Leading |
| 4.3.6.1 Transaction Processing | | |
| 4.3.6.2 Master Data | | |
| 4.3.6.3 Assisted Buying | | |
| 4.3.6.4 MIS | | |

TABLE 96

Global Health and Life Sciences High Performance
Capability Assessment Model - Public Health Services - Medicaid
Enterprise

| Sub-Platform: Procurement Management | | Capability: Sourcing and Category Management |
|---|---|---|
| Basic | Competitive | Market Leading |
| Strategic Sourcing: "Three quotes" approach solely done by procurement | Strategic Sourcing Strategic Sourcing: Commodity/Cross team driven approach | Strategic Sourcing: Process rigor, dictated by common cross-functional, analytical method |

TABLE 96-continued

Global Health and Life Sciences High Performance
Capability Assessment Model - Public Health Services - Medicaid
Enterprise Sub-Platform: Procurement Management     Capability: Sourcing and Category Management

| Basic | Competitive | Market Leading |
|---|---|---|
| | Global Sourcing: deployed global sourcing strategy in place, penetrating new markets | |
| | eSourcing: Simple reverse auction for all commodities | |
| Global Sourcing: Only done on an ad hoc basis | Category Policy Setting Departmental policies, processes and procedures are in alignment with corporate policies | Global Sourcing: Total landed cost framework to fully leverage LCC opportunities to reduce TCO |
| eSourcing: Simple reverse auctions for a few categories | Category Management Framework Disparate category management structure that vary throughout the organization Procurement personnel dedicated to specific category management | eSourcing: Technology driving global collaboration, knowledge management and efficiency |
| Departmental policies establish standards of conduct and promote compliance with applicable laws and regulations. | Compliance Monitoring Compliance strategy in place, reviewed periodically | Policies are established and communicated to convey the Corporation's position and philosophy; additionally, they provide governance over employees actions. |
| No category management framework established | | Centrally guided category management structure that cut across organizational entities |
| Groups of buyers | | Dedicated sourcing analyst pool that provides support during the sourcing and category management process |
| Significant maverick spend | | Discipline, full control with non-compliance driving corrective actions |

TABLE 97

Global Health and Life Sciences High Performance
Capability Assessment Model - Public Health Services - Medicaid
Enterprise Sub-Platform: Procurement Management     Capability: Supplier Relationship Management

| Basic | Competitive | Market Leading |
|---|---|---|
| Reactive, only talking to suppliers when problems occur | Supplier Performance Management Supplier performance metrics established | Targeted approach, differentiated by supplier segment |
| Procurement is involved and urges groups to adopt industry or supplier standards | Supplier Integration Key suppliers are involved for input on alternate materials and design for manufacturability issues Key suppliers are incorporated into planning process, forecast shared | Integrated product development involving customer focus groups suppliers and design teams, with suppliers performing component development in line with overall business and product strategy |
| Limited to a few problem solving meetings | Contract Management Some long term contracts in place on "big ticket" items or raw materials Single contract management solution | Joint Process/Product Improvements, eSupply Chain Integration |
| Horizon based on material requirements released to procurement on requisition | Supplier Development Vendor sharing of actual costs and profit margins Supplier development initiative established | Supplier pricing based on long term alliance agreements and delivery is based on production schedule |
| Multiple contract databases and ad hoc compliance management | | Centrally logged contracts, pro-active mgmt of contract compliance |

TABLE 97-continued

Global Health and Life Sciences High Performance
Capability Assessment Model - Public Health Services - Medicaid
Enterprise

| Sub-Platform: Procurement Management | | Capability: Supplier Relationship Management |
|---|---|---|
| Basic | Competitive | Market Leading |
| Raw materials purchasing based on competitive bids versus relationships | | Sharing of technical expertise to improve product performance and reduce costs |
| No systemic approach of supplier development | | Focus on repeatable LCC supplier development |

TABLE 98

Global Health and Life Sciences High Performance
Capability Assessment Model - Public Health Services - Medicaid
Enterprise

| Sub-Platform: Procurement Management | | Capability: Manage Human and Tangible Resources |
|---|---|---|
| Basic | Competitive | Market Leading |
| 4.3.1.1 Change Agency | | |
| 4.3.1.2 Make vs. Buy | | |
| 4.3.1.3 Competitive Awareness | | |

TABLE 99

Global Health and Life Sciences High Performance
Capability Assessment Model - Public Health Services - Medicaid
Enterprise

| Sub-Platform: Privacy and Compliance Management | | Capability: Manage Privacy Compliance |
|---|---|---|
| Basic | Competitive | Market Leading |
| 4.6.1.1 Maintain Training, Whistleblower Program, etc. | | |
| 4.6.1.2 Manage Reporting Requirements | | |

TABLE 99-continued

Global Health and Life Sciences High Performance
Capability Assessment Model - Public Health Services - Medicaid
Enterprise

| Sub-Platform: Privacy and Compliance Management | | Capability: Manage Privacy Compliance |
|---|---|---|
| Basic | Competitive | Market Leading |
| 4.6.1.3 Manage HIPAA and State Privacy Compliance | | |
| Maintain Privacy Office | | |
| Maintain Authorizations | | |
| Manage Disclosure | | |
| 4.6.1.3 Manage HIPAA and State Privacy Compliance | | |
| Maintain Protected Health Information (PHI) | | |
| Manage Trading Partners | | |
| Manage Security | | |
| Manage Quality and Performance Privacy and Security | | |
| 4.6.1.4 Manage Sarbanes-Oxley Compliance | | |
| Manage Documentation and Data Retention | | |
| Manage Attestation | | |
| 4.6.1.5 Manage CMS Compliance | | |

TABLE 100

Global Health and Life Sciences High Performance
Capability Assessment Model - Public Health Services - Medicaid
Enterprise

| Sub-Platform: Legal Management | Capability: Manage Legal Issues | |
|---|---|---|
| Basic | Competitive | Market Leading |
| 4.2.1.1 Manage Legal Services | | |
| 4.2.1.2 Ensure Regulatory Compliance | | |
| 4.2.1.3 Provide Litigation Services | | |
| 4.2.1.4 Provide Tax Advice | | |
| 4.2.1.5 Advise Other Plan Departments | | |
| 4.2.1.6 Manage Quality and Performance of the Legal Process | | |

TABLE 101

Global Health and Life Sciences High Performance
Capability Assessment Model - Public Health Services - Medicaid
Enterprise

| | Sub-Platform: Human Resources | Capability: Manage Human and Tangible Resources | |
|---|---|---|---|
| Basic | | Competitive | Market Leading |

4.5.1.1 Manage Workforce Capacity
4.5.1.2 Manage recruiting
4.5.1.3 Manage Compensation
and Benefits
4.5.1.4 Manage Employee Services
4.5.1.5 Manage Training and Career
Development
4.5.1.6 Manage Quality and
Performance of
Human and Tangible Resources

TABLE 102

Global Health and Life Sciences High Performance Capability Assessment
Model - Public Health Services - Medicaid
Enterprise

| | Sub-Platform: Information Technology Operations | | Capability: Architecture Management - Application Architecture |
|---|---|---|---|
| Basic | | Competitive | Market Leading |
| Application suites documented but without review and quality control checkpoints | Components are configurable and quality assurance practiced | | Related software and processes have been defined and actively monitored |
| Application architecture developed for pockets of projects only | Application suite architected considering planned service delivery commitments and tracking | | Supporting software, development and maintenance processes improved to appropriate levels (e.g. best in class) and focus on proactive fault prevention |
| Some rationalization efforts, though fragmented and inconsistent across groups | Application architecture defined for functional groups | | Enterprise-wide application architecture is actively managed for business value and regularly refreshed according to changing business and technical needs |
| Integration layer is documented but without any review and quality control checkpoints | Application architecture is consistently enforced | | Application portfolio rationalization opportunities integrated into new project objectives and planning |
| Some standardized interfaces such as EDI or common tools | Application portfolio defined, rationalization process documented and practiced consistently across all groups | | Active process management for integration architecture in place |
| | Integration architecture considered across functional units and quality assurance practiced in general | | Integration/interface architecture refreshed regularly |
| | Integration/interface architecture is consistently enforced | | Interface re-use is actively managed and enforced and considered in business cases |
| | Standards with supporting common integration tool sets (e.g., messaging, interface building, data transport) exist | | |

TABLE 103

Global Health and Life Sciences High Performance
Capability Assessment Model - Public Health Services - Medicaid
Enterprise

| Sub-Platform: Information Technology Operations | | Capability: Strategic IT Alignment - Business and IT Alignment |
|---|---|---|
| Basic | Competitive | Market Leading |
| Business and/or IT strategy is unclear and not fully communicated | Business and IT strategy exist and there is some broad linkage between the two | IT strategy priorities are continuously adjusted to match business needs |
| IT and business work in their silos with mostly reactive and one-way communications | IT and business discuss alignment for critical projects | IT and business are jointly responsible for defining IT strategy and review the strategy on set schedule |
| Where a strategy has been articulated, it is often not defined at an operational level leaving it open to interpretation | IT strategy is translated to operational levels at varying levels of detail generally resulting in consistent interpretation | The strategy is translated to clear operational plans and for specific audience, and tied to group and individual goals |
| Strategy communication is ad hoc via varying channels to a fragmented set of audience | Strategy communication frequency, channels, audience are defined, but still inconsistently executed | Strategy communication frequency, content and channels are customized to audience and regularly managed |
| IT has limited involvement in Business Unit discussions, often resulting in an incomplete strategic view and risk of deviation from the strategy | IT is typically involved in Business Unit strategic discussions with the strategy generally inclusive of IT implications and correctly executed | IT is involved in key Business strategic discussions to ensure the strategy is comprehensive and correctly executed |
| IT initiative prioritization and approval process informally exists | IT initiative prioritization and approval process defined with formal steps for business objective alignment, compliance review and formal sign off by key decision makers, but not consistently followed | IT initiative prioritization and approved process proactively managed with business involvement for all IT initiatives |
| It has limited influence on strategic agenda | IT is involved in all strategic initiatives consistently across enterprise | IT is a respected strategic partner to business |
| Business IT Liaison plays a simple order taker role | Business IT Liaison role is clearly defined across business areas | Business IT Liaison plays a lead role in IT-enabled business transformation and acts as a change agent |
| Business IT Liaison is equipped with limited "tools" | Business IT Liaison demonstrates knowledge of business processes and interactions across multiple functional areas | Business IT Liaison maintains deep knowledge of organization-wide IT roadmap, objectives, risks, interactions and issues |
| Information feedback mechanism on performance or customer satisfaction in place | Feedback process on performance and customer satisfaction defined, but not consistently enforced | Proactive management of performance feedback and customer satisfaction results for continuous improvement |

TABLE 104

Global Health and Life Sciences High Performance Capability Assessment
Model - Public Health Services - Medicaid
Enterprise

| Sub-Platform: Information Technology Operations | | Capability: Solutions Delivery - Collaboration |
|---|---|---|
| Basic | Competitive | Market Leading |
| Informal and ad hoc sharing between teams | Sharing of key knowledge documentation exists throughout the life-cycle within IT and with the business customers | Proactive and ingrained sharing of key knowledge documentation throughout the life-cycle within IT and with the business customers |
| No standards or guidelines as how to store project documentation | Knowledge sharing tools deployed to facilitate capture and distribution | IT continuously looks for ways to improve its knowledge sharing capabilities and regularly reviews its knowledge database |
| Lack of adequate infrastructure and tools to incite communication | Various repositories for project documentation, none used completely or consistently | Knowledge is actively communicated and updated with feedback from all stakeholders |
| Ad hoc and inconsistent communication of knowledge | Consistent processes across groups/locations | Proactive involvement of technology and business groups in optimizing knowledge communication |

TABLE 104-continued

Global Health and Life Sciences High Performance Capability Assessment
Model - Public Health Services - Medicaid
Enterprise Sub-Platform:  
Information Technology Operations Capability:  
Solutions Delivery - Collaboration

| Basic | Competitive | Market Leading |
|---|---|---|
| Knowledge communication ownership is loosely defined | Communication ownership well defined with leaders assigned by group, function or topic | |

TABLE 105

Global Health and Life Sciences High Performance
Capability Assessment Model - Public Health Services - Medicaid
Enterprise Sub-Platform: Information Technology Operations Capability: Strategic IT Alignment - Communicate IT Strategy

| Basic | Competitive | Market Leading |
|---|---|---|
| Ad hoc communications of the IT vision and strategy | IT vision and strategy regularly communicated internally to various stakeholders<br><br>Communications not aligned to the IT strategy refresh cycle | IT vision and strategy regularly communicated internally to and externally to various stakeholders |

TABLE 106

Global Health and Life Sciences High Performance
Capability Assessment Model - Public Health Services - Medicaid
Enterprise Sub-Platform: Information Technology Operations Capability: IT Governance - Develop/Administer IT Budgets

| Basic | Competitive | Market Leading |
|---|---|---|
| Informal IT funding model exists<br><br>The allocation of IT budget is ad hoc and reactive | IT funding model allows for increases in IT spending to realize defined benefits<br>Allocation of IT budget is partially influenced by business objectives<br>Business and IT managers work together throughout the year to allocate resources on the basis of operational priorities | IT funding model designed to drive appropriate behaviors in business and IT<br>Allocation of IT budget is driven by business strategic priorities<br>Business managers participate in IT planning, and approve IT priorities and allocations of funds on the basis of strategic priorities |

TABLE 107

Global Health and Life Sciences High Performance
Capability Assessment Model Public Health Services - Medicaid
Enterprise Sub-Platform: Information Technology Operations Capability: Architecture Management - End-User Computing Architecture

| Basic | Competitive | Market Leading |
|---|---|---|
| End-user computing requirements are documented but without any review and quality control checkpoints<br>Multiple end-user computing devices, possibly including thin, 3270-like and thick clients with multiple software configurations | End-user computing architecture considered across functional units and quality assurance practiced in general<br>End-user computing architecture is consistently enforced | Active process management for end-user computing architecture in place<br>A small number of end-user computing device configurations, designed to deliver required service at lower costs. |

TABLE 107-continued

Global Health and Life Sciences High Performance
Capability Assessment Model Public Health Services - Medicaid
Enterprise

| Sub-Platform: Information Technology Operations | | Capability: Architecture Management - End-User Computing Architecture |
|---|---|---|
| Basic | Competitive | Market Leading |
| Rudimentary business value implications for end-user computing architecture | End-user computing device set with planned set of hardware devices and managed software configurations | End-user computing architecture has been designed and implemented with consideration for overall application strategy, total cost of ownership and service targets, and is refreshed regularly |
| | Defined end-user computing configurations sets designed to deliver to clear service targets; supporting organizational structures and training | |

TABLE 108

Global Health and Life Sciences High Performance
Capability Assessment Model - Public Health Services - Medicaid
Enterprise

| Sub-Platform: Information Technology Operations | | Capability: IT Governance - Establish/Manage IT Standards |
|---|---|---|
| Basic | Competitive | Market Leading |
| IT standards are in its infancy Little enterprise-wide standards exist. | Standards established by IT with little or no input from business, with minimal accountability | Clear, consistent and comprehensive IT standards developed and maintained to guide decision making and action in accordance with established business and IT policies |
| IT standards are after-thought and many business users consider IT standards as hindrance | Adherence to standards enforced periodically depending on budget pressures | Changes in business direction and strategy assessed to determine impact on relevancy of standards |
| Unclear how IT standards would be linked to external/regulatory compliance | Standards changed often to allow for requested exceptions, or not examined for change at all Internal and external audits are conducted to ensure standards compliance to external regulations | Impact of business and technology trends on standards assessed Changes to existing standards clearly documented and communicated to all affected parties Dedicated compliance resources continuously monitors IT standards in lieu of changing external regulations |

TABLE 109

Global Health and Life Sciences High Performance
Capability Assessment Model - Public Health Services - Medicaid
Enterprise

| Sub-Platform: Information Technology Operations | | Capability: Architecture Management - Infrastructure Architecture |
|---|---|---|
| Basic | Competitive | Market Leading |
| Infrastructure requirements are documented but without any review and quality control checkpoints | Infrastructure architecture considered across functional units and quality assurance practiced in general | Active process management for infrastructure architecture in place |

TABLE 109-continued

Global Health and Life Sciences High Performance
Capability Assessment Model - Public Health Services - Medicaid
Enterprise

| | Sub-Platform: Information Technology Operations | Capability: Architecture Management - Infrastructure Architecture |
|---|---|---|
| Basic | Competitive | Market Leading |
| Infrastructure architecture requirements are not well defined | Configuration management and quality assurance applied to architectures<br>Infrastructure architecture is consistently enforced | Architectures designed, managed and regularly refreshed to meet financial and service targets<br>Tiered architectures (Infrastructure and Data Center) have been defined and are being measured and tested for availability, recoverability and performance |
| | Distributed architecture set considered and implemented to deliver planned service delivery commitments with tracking<br>Data Center hierarchies articulated and facilities set up to deliver required services with requisite physical security | Architectures have been on harmonized to maximized Return Investment and minimize Total Cost of Ownership |

TABLE 110

Global Health and Life Sciences High Performance
Capability Assessment Model - Public Health Services - Medicaid
Enterprise

| | Sub-Platform: Information Technology Operations | Capability: Service and Management Operations - Infrastructure Services Governance |
|---|---|---|
| Basic | Competitive | Market Leading |
| Business requirements for availability exist but are not documented or communicated | Availability requirements documented but not effectively monitored or measured | Availability requirements determined jointly by business and service provider, based on cost per level of availability |
| Ad hoc planning efforts to set and monitor availability with no plan in place | Availability requirements not based on baseline data | Availability requirements balance cost against business need |
| Initial efforts at capacity modeling with multiple inconsistent models in place | Availability plan documents components as well as business services | Availability strategy reviewed regularly for effectiveness and efficiency |
| The capacity plan has fragmented structure, where roles and responsibilities are not clearly defined | Organization does not have good data to measure whether availability plan is met beyond the component level | Availability planning performed at service level |
| Basic service continuity includes restore from back up media | Capacity model defined and consistently utilized across all groups | Capacity modeling is continuously improved via incremental changes |
| Business owners are not involved to assess the strategy based on business impact analysis | Capacity modeling personnel have access to financial, physical, operational, software, and vendor requirements in order to complete model | Business users have input to the capacity model |
| The plan is a paper document that is rarely reviewed | A standard enterprise capacity plan exists | Capacity planning is continuously improved via incremental changes over the course of the year |
| The initial builders and testers of the IT service continuity plan are the only ones trained on it | Plan updated at specified intervals | Capacity planning efforts are able to predict, anticipate, understand, and react rapidly to business changes impacting IT services |
| Some critical business services identified, but not consistent across groups | Business demand forecasts are incorporated into the capacity plan | The strategy is fully supported and sponsored by multiple executives in the organization to ensure that during a disaster a recovery would be guaranteed within the recovery period agreed upon |

TABLE 110-continued

Global Health and Life Sciences High Performance
Capability Assessment Model - Public Health Services - Medicaid
Enterprise Sub-Platform: Information Technology Operations Capability: Service and Management Operations - Infrastructure Services Governance

| Basic | Competitive | Market Leading |
|---|---|---|
| Service model lacks structure and is paper based; service dependencies are informally understood | A well documented strategy exists and agreed upon by business operations and IT | Business/disaster recovery planning and management's software is tied to backup/restore/archive system for metrics reporting and issues tracking |
| Some services are documented, but no central catalog exists | Recovery options have been agreed upon for each business process | IT service continuity director and supporting staff have taken external training to learn the industry standards for IT service continuity |
| End user experience is monitored as users report service problems | The plan is reviewed and audited yearly by business and IT stakeholders | Critical business service documentation is regularly reviewed in accordance with changes in business imperatives |
| No performance measure or targets/objectives set beyond overall costs | The plan is an electronic document with links to supporting documents that are updated regularly with the change management processes. | Service model is highly effective in predicting the business impact of technology events |
| Costs tracked, but inconsistently across groups | Training policy is in place for new recovery team members and any other personnel that may be required in a disaster | Comprehensive service catalog jointly reviewed and updated between IT and business |
| Risks identified at functional level and for projects | Critical business services are documented | Service Catalog automatically updated when new configuration item is place in the system |
| No overall account ability for IT risks | Service model is documented | End-user experience model created and utilized to predict and proactively control user experience |
| | Well documented service catalog exists | Balanced set of performance measures set, linked directly to business and IT strategy. |
| | Service goals clearly support critical business services | Regular monitoring and proactive revision of plaan and targets through the year |
| | Automated monitoring of end user experience | Charges based on services, not technology |
| | Clear objectives set for the IT function | |
| | Focus is mainly on efficiency measures | |
| | Technology service units costed and used as the basis for recharge | |
| | Risk management is defined accountability | |

TABLE 111

Global Health and Life Sciences High Performance
Capability Assessment Model - Public Health Services - Medicaid
Enterprise Sub-Platform: Information Technology Operations Capability: Strategic IT Alignment - IT Innovation

| Basic | Competitive | Market Leading |
|---|---|---|
| Limited survey of technologies conducted | Market leading technologies are studied and actively investigated to potentially enable business objectives | Technology scanning is ingrained into overall IT and business processes |
| IT is perceived to Order Taker ("Do what you're told") | IT is Solutions Provider ("Bring ideas to the table") | IT is Change Agent, leading efforts to innovate business practices |
| Limited innovation thinking and innovation is either too early or too late to effectively enable business strategy and growth | IT innovations support business productivity | IT serves as Change Agent and Leader ("Drive change - out in front") |

TABLE 111-continued

Global Health and Life Sciences High Performance
Capability Assessment Model - Public Health Services - Medicaid
Enterprise

| Sub-Platform: Information Technology Operations | | Capability: Strategic IT Alignment - IT Innovation |
| --- | --- | --- |
| Basic | Competitive | Market Leading |
| Ideas and innovations lack ownership and follow-through | Investment levels in innovation driven by business performance (varies year to year) | IT innovations enable the business strategy and support growth |
| Innovation ideas prioritized ad hoc or using a 'squeaky wheel' approach | Fast Follower' in IT direction | Innovation supported by business leadership and direction |
| The development lifecycle is often slow and inflexible in delivering business capability and often results in reduced benefit capture | Innovations are identified through a range of sources both internal and external usually by a process of collection | Steady investment as a percentage of total IT cost |
| | | Innovations adopted at the right point of time 'Market Leader' |

TABLE 112

Global Health and Life Sciences High Performance
Capability Assessment Model - Public Health Services - Medicaid
Enterprise

| Sub-Platform: Information Technology Operations | | Capability: Architecture Management - Manage EDI and Paper Transactions |
| --- | --- | --- |
| Basic | Competitive | Market Leading |
| 4.4.3.9.1 Process Web-Based Transactions | | |
| 4.4.3.9.2 Process EDI Transactions | | |
| 4.4.3.9.3 Process Paper Transactions | | |
| 4.4.3.9.4 Manage Quality and Performance of the Transactions Process | | |

TABLE 113

Global Health and Life Sciences High Performance
Capability Assessment Model - Public Health Services - Medicaid
Enterprise

| Sub-Platform: Information Technology Operations | | Capability: Architecture Management - Manage Information Systems and Technology and Security |
| --- | --- | --- |
| Basic | Competitive | Market Leading |
| 4.4.3.10.1 Plan and Develop Technology Enablement Capabilities | | |
| 4.4.3.10.2 Manage Application Infrastructure | | |
| 4.4.3.10.3 Manage Technical Infrastructure | | |
| 4.4.3.10.4 Manage Hardware Infrastructure | | |
| 4.4.3.10.5 Manage Quality and Performance of the Information Systems Process | | |
| 4.4.3.10.6 Govern Information Management | | |
| 4.4.3.10.7 Identify Knowledge Requirements, Resources, and Gaps | | |
| 4.4.3.10.8 Collect and Develop Knowledge | | |
| 4.4.3.10.9 Manage Knowledge Repositories | | |

TABLE 113-continued

Global Health and Life Sciences High Performance
Capability Assessment Model - Public Health Services - Medicaid
Enterprise

| Sub-Platform: Information Technology Operations | | Capability: Architecture Management - Manage Information Systems and Technology and Security | |
|---|---|---|---|
| Basic | | Competitive | Market Leading |

4.4.3.10.10 Manage User Access & Support of Information Management
4.4.3.10.11 Manage Applications Development, Production & Delivery of Information Management
4.4.3.10.12 Manage Quality and Performance of the Knowledge Management Process

TABLE 114

Global Health and Life Sciences High Performance
Capability Assessment Model Public Health Services - Medicaid
Enterprise

| Sub-Platform: Information Technology Operations | | Capability: IT Governance - Manage Initiatives to Realize Benefits | |
|---|---|---|---|
| Basic | Competitive | | Market Leading |
| Investments managed independently with minimal consideration of overall IT portfolio | IT portfolio monitored and benefits realization calculated consistently for key projects on completion | | IT portfolio is focused on taking actions to proactively optimize performance against target benefits Investment portfolio actively |
| Limited business participation in IT portfolio management | Business is engaged in IT portfolio management for all functional areas | | managed and measured jointly by IT and business continuously IT and Business strategically |
| Only handful of benefits measurement exists and the majority of them are operationally-focused | IT scorecard used to drive IT steering committee agenda KPIs, typically financial-based, for IT Delivery are identified and reported regularly | | aligned with focus on identified sources of value from IT Joint Committees of the appropriate senior Business and IT leaders are actively engaged in guiding the IT Investment pipeline, portfolio of in-flight projects |
| | IT scorecard used to drive IT steering committee agenda All IT areas define performance targets and are tracked on their ability to meet these targets | | IT and Business strategically aligned with focus on identified sources of value from IT Joint Committees of the appropriate senior Business and IT leaders are actively engaged in guiding the delivery of day-to-day services |
| | IT scorecard used to drive IT steering committee agenda Rewards typically tied to overall business performance | | IT and Business strategically aligned with focus on identified sources of value from IT Joint Committees of the appropriate senior Business and IT leaders are actively engaged in guiding at enterprise, business unit and program/project/service level |
| | | | IT and Business strategically aligned with focus on identified sources of value from IT Refinement of priorities, funding and resource is aligned with accountabilities in the business and with the group's strategic intent |

TABLE 115

Global Health and Life Sciences High Performance
Capability Assessment Model - Public Health Services - Medicaid

Enterprise

Sub-Platform: Information Technology Operations  
Capability: IT Governance - Manage Service Provider Relationships

| Basic | Competitive | Market Leading |
|---|---|---|
| Multiple diverse sourcing strategies in place<br>Little or no controls in place for vendors relationship management<br>Limited contracting rules defined<br>Limited vendor performance process and metrics are in place | Enterprise-level sourcing strategy defined, but not consistently followed<br>Large or key supplier relationships managed in a consolidated manner<br>External contracting process defined and applied consistently to key projects<br>Escalation procedures exist, but not consistently followed<br>Monitoring and controls for vendor performance defined and managed within IT | Sourcing strategy flexible end regularly refreshed based on objectives and degree of commoditization<br>Coordinated management of supplier relationships aligned with the business/IT sourcing strategy<br>External contracts managed consistently and tracked against contracting rules<br>Vendor performance is actively tracked against external industry performance benchmark<br>Actions taken proactively when potential issues are identified |

TABLE 116

Global Health and Life Sciences High Performance
Capability Assessment Model - Public Health Services - Medicaid

Enterprise

Sub-Platform: Information Technology Operations  
Capability: Strategic IT Alignment - Measure Value from IT

| Basic | Competitive | Market Leading |
|---|---|---|
| Ownership and accountability of benefits realization are not clearly defined and communicated<br>Benefits realization is considered by business managers to be IT responsibility only<br>Some value-based metrics exit for a few simple to define areas<br>No formal communication as to value added by IT | Ownership and accountability of benefits realization agreed between the Business and IT for key projects only<br>Business managers have limited responsibility for benefits realization and accountability<br>Business value metrics connected to IT initiatives exist, but not for all functional areas<br>IT works to ensure that business is aware of IT's value add to the enterprise, but not on a regular basis | Ownership and accountability of benefits realization shared and agreed between the Business and IT<br>Responsibilities are clearly defined and well communicated<br>Ownership and accountability of benefits realization shared and agreed between the Business and IT<br>Benefits realization is jointly tracked and managed by IT and the business<br>Ownership and accountability of benefits realization shared and agreed between the Business and IT<br>Business and IT fully collaborate to ensure that projected benefits will be achieved<br>IT and business metrics used to evaluate business case and impact and serve as input to adjusting estimating methods<br>IT produces IT scorecard and IT quarterly/annual reports to report business value added to the organization |

TABLE 117

Global Health and Life Sciences High Performance
Capability Assessment Model - Public Health Services - Medicaid Enterprise Sub-Platform: Information Technology Operations  
Capability: Architecture Management - Network Architecture

| Basic | Competitive | Market Leading |
|---|---|---|
| Diverse network architecture in place and functional<br>Blended cost of service per user reported annually | Data network architecture in place for WAN, MAN, LAN and Internet.<br>Configuration Management and Quality Assurance practiced<br>Network architecture is consistently enforced | Financial considerations in place for network architecture design and implementation<br>Architecture design and management improved to appropriate levels (e.g. best in class) and focus on design, operation optimization and Total Cost of Ownership |

TABLE 118

Global Health and Life Sciences High Performance
Capability Assessment Model - Public Health Services - Medicaid Enterprise Sub-Platform: Information Technology Operations  
Capability: Architecture Management - Operations Architecture

| Basic | Competitive | Market Leading |
|---|---|---|
| Operations architecture requirements are documented but without any review and quality control checkpoints<br>Patchy architecture decisions mostly individual driven<br>Documented inventory of hardware and software components<br>Rudimentary cost analyses accompany operational architecture development | Operations architecture considered across functional units and quality assurance practiced in general<br>Operations architecture is consistently enforced<br>Integration of hardware and software components practiced, but still inconsistent across groups<br>ITIL processes defined and implemented for Incident, Capacity*, Availability, Operations, Problem, Configuration and Change<br>Hardware and software components are managed to a limited set of service level targets | Active process management for infrastructure architecture in place<br>ITIL fully implemented to manage Technical Operations, Service Desk and Service Control with measurement and adjustments completed<br>Service strategy and design process revisited annually<br>Financial and service targets as key driver of hardware end software portfolio design |

TABLE 119

Global Health and Life Sciences High Performance
Capability Assessment Model - Public Health Services - Medicaid Enterprise Sub-Platform: Information Technology Operations  
Capability: IT Governance - Plan/Prioritize Initiative Portfolio

| Basic | Competitive | Market Leading |
|---|---|---|
| The are only informal and verbal business cases for initiatives before they are implemented<br>Risks identified at functional level and for projects. No overall accountability for IT risks<br>Attention to IT-related risks is reactive based on current issues with no overall consideration for magnitude | Basic initiative prioritization and approval processes defined and consistently followed<br>Initiatives are defined and evaluated in a consistent manner<br>Basic initiative prioritization and approval processes defined and consistently followed<br>Initiatives and projects are evaluated independently with minimal consideration for overlap, resource constraints or conflicts<br>Potential high risk scenarios are identified and risk mitigation plans developed<br>Risk checklist is used in sizing projects and initiatives. | Initiatives are continuously examined by IT and Business stakeholders to ensure that investments and budgets are used appropriately<br>Potential Investments are tracked and managed through a multi-stage demand pipeline with clear decision gates<br>Initiatives are continuously examined by IT and Business stakeholders to ensure that investments and budgets are used appropriately<br>provides a view of future demand and allows level of effort invested to scope and shape |

TABLE 119-continued

Global Health and Life Sciences High Performance
Capability Assessment Model - Public Health Services - Medicaid

| | IT asset inventory is complete and accurate. Proactive asset management practices in place | initiatives to be managed<br>Initiatives are continuously examined by IT and Business stakeholders to ensure that investments and budgets are used appropriately<br>Clear visibility of emerging dem and, status and interrelationship of in-flight projects.<br>Initiatives are continuously examined by IT and Business stakeholders to ensure thet investments and budgets are used appropriately<br>Clear visibility of service delivery performance<br>IT risk management is an integral part of all IT processes. External risk audits are conducted and immediately acted upon<br>Potential risks are anticipated well in advance of their occurrence, and systematic changes are instituted to actively manage and mitigate risks based on exposure and potential severity |
|---|---|---|

TABLE 120

Global Health and Life Sciences High Performance
Capability Assessment Model - Public Health Services - Medicaid Enterprise

| Sub-Platform: Information Technology Operations | Capability: Strategic IT Alignment - Plan and Manage IT Capability | |
|---|---|---|
| Basic | Competitive | Market Leading |
| IT capabilities are not well documented<br>Minimal capability assessment performed or performed against an inadequate information base | IT capabilities are well documented and are updated through the change control process<br>Capability assessment performed based on the current view of the asset portfolio and architecture | IT continuously evaluates its application and infrastructure capabilities to optimize business performance for opportunities to reduce costs and improve time to market<br>IT capabilities are cortinuously evaluated end adjusted based on performance against the targeted state and/or changes in progress |

TABLE 121

Global Health and Life Sciences High Performance
Capability Assessment Model - Public Health Services - Medicaid Enterprise

| Sub-Platform: Information Technology Operations | Capability: Solutions Delivery - Program Management | |
|---|---|---|
| Basic | Competitive | Market Leading |
| Entirely IT driven; limited to no business involvement<br>Programs are considered a superset of projects<br>Same processes and deliverables for program management as for project management<br>No explicit or formal approval at program level<br>Rudimentary master schedule developed<br>Informal program metrics exists, but not well-understood<br>Same processes and deliverables for program management as for project management - just summarized | Project management is equally shared by IT and business management<br>A separate charter approved by business exists for the program<br>Systematic program approval process exists and generally followed<br>Master schedule is clearly delineated into releases that are business capability based<br>Program management metrics include some value realization<br>Program management processes are defined and focused on interdependence between projects | Control over the application of information technology is fully integrated with company's principal functional units<br>Joint business and IT steering committee performs program management<br>Program management part of company culture, integrating multiple functional disciplines to achieve business outcomes<br>Approval process and evaluation criteria actively managed and improved with business inputs<br>Proactive planning, review end packaging of all projects |

TABLE 121-continued

Global Health and Life Sciences High Performance
Capability Assessment Model - Public Health Services - Medicaid

| | | |
|---|---|---|
| Program-level reporting is informal | Program communications more than simple aggregation- reports progress to achievement of overall vision and business results; separation of project versus program risks and issues<br>Program reporting at times inconsistent | Business value-based program metrics continuously monitored jointly with business<br>Program management processes are ingrained as a part of the enterprise-wide processes<br>Program management processes focus on realizing business value and actively managed and improved with business inputs<br>Program milestones and deliverables actively monitored jointly with business<br>Program reporting prompts C-level executives to take appropriate actions |

TABLE 122

Global Health and Life Sciences High Performance
Capability Assessment Model - Public Health Services - Medicaid

Enterprise

| Sub-Platform: Information Technology Operations | Capability: Solutions Delivery - Quality Management | |
|---|---|---|
| Basic | Competitive | Market Leading |
| Quality assurance process is informal<br>Implementation of improvement initiatives not coordinated or prioritized<br>Informal quality standards exists<br>Informal quality targets set<br>Customer, client, and employee surveys conducted rarely, survey results inconsistently analyzed to and interpreted to guide immediate improvement activities only | Key Processes defined and implemented: Process Quality Assurance<br>Solution Quality Management<br>Management of key stakeholders performed<br>Planned and coordinated implementation of improvement initiatives<br>Quality standards exist, but not consistently followed<br>Various naming conventions and templates<br>Program/project management is evaluated based on a balanced scorecard that captures productivity and outcome information<br>Customer, client, end employee surveys conducted on an ad hoc basis; survey results analyzed and interpreted to guide immediate improvement activity | Engrained management of stakeholders and development of stakeholder goals and expectations as a guide to process improvement<br>Process and product QA consistently managed and tracked. Regular scheduled reviews of process and product quality. Non-compliance issues is formally communicated and resolution is implemented<br>Existence of an organization wide Software Quality Assurance (SQA) group with a quality assure or assigned to each project to ensure process compliance for processes<br>Standardized set of naming conventions, templates and quality standards exists and regularly updated<br>Advanced metrics collected and actively managed with all stakeholders involved<br>Regular customer, client, and employee surveys administered by clear communications; survey results analyzed and interpreted to guide immediate and future improvement activity |

TABLE 123

Global Health and Life Sciences High Performance
Capability Assessment Model - Public Health Services - Medicaid

Enterprise

| Sub-Platform: Information Technology Operations | Capability: Architecture Management - Security Architecture | |
|---|---|---|
| Basic | Competitive | Market Leading |
| Security architecture is loosely documented without quality standards<br>One or additional diverse security infrastructures, services, policies, standards, administration and operations in place<br>No cohesion with industry standards or frameworks | Frameworks such as GIM TS (ISO 13335), COBIT, and ISO 17799 defined and applied to infrastructures, policies, services and operations as well as their management<br>Security architecture is consistently followed<br>Enterprise security architecture consistently practiced across groups | Security architecture designed within frameworks to enable and facilitate business value and provide effective risk management<br>Harmonized security architectures for Infrastructures, policies, services and operations according to published frameworks<br>Business Continuity/Disaster Recovery plans |

TABLE 123-continued

Global Health and Life Sciences High Performance
Capability Assessment Model - Public Health Services - Medicaid

| | | |
|---|---|---|
| Limited Business Continuity and Disaster Recovery considerations | Cohesion between utilized standards such as ISO 17799, for services, policies, operations and infrastructure. Business Continuity/Disaster Recovery for defined critical set of applications | are managed and regularly refreshed to ensure business success |

TABLE 124

Global Health and Life Sciences High Performance
Capability Assessment Model - Public Health Services - Medicaid

| | Enterprise | |
|---|---|---|
| Sub-Platform: Information Technology Operations | Capability: Service and Management Operations - Service Delivery | |

| Basic | Competitive | Market Leading |
|---|---|---|
| Informal, reactive service provided. Fragmented technology, if it exists at all Escalation process may exist, but is undocumented and is not monitored Communication process may exist, but is haphazard, individual effort based Ad hoc measurement of service performance No formal agreements on SLAs/OLAs Availability monitoring is informal and no accountability for performance exists Ad hoc measurement of service performance Informal reviews of SLAs/OLAs | Service desk is established and processes are standardized and documented Service desk functionality supported by software and technology that streamlines service and minimizes human involvement Escalation processes are documented and applied informally and inconsistently Customer communication process documented and articulated to the organization Efforts made to inform customers of current service availability Service requirements for OLAs and SLAs are established SLAs/OLAs are measured inconsistently, organization makes the effort but automation not developed to the point where measurements are accurate Organization able to catalog services offered by IT Organization has SLAs/OLAs in place, does not know for certain whether or not they are met Service breaches are usually identified, but not always related back to SLA SLAs/OLAs are written, review schedule is set out nobody is responsible for actually following up. Consequently, updates often do not occur or are late | Service support process and policies are regularly monitored and refreshed using customer input end performance statistics Tools and technology are regularly reviewed and technology scan performed to refresh existing tools Escalation processes are well structured and monitored for adherence Escalation results conveyed back to customer Customers are surveyed regularly regarding overall satisfaction with the service desk Customers are surveyed to confirm satisfaction upon call resolution SLA/OLA monitoring plan specified as part of contract Comprehensive service catalog linked to hierarchy of howservices are related OLAs/SLAs for particular service consistent across providers End to end monitoring enables accurate measurement of business services, bath from an availability and a performance perspective Incidents can be linked to services SLA/OLA monitoring plan specified as part of contract Comprehensive service catalog linked to hierarchy of howservices are related OLAs/SLAs for particular service consistent across providers |

TABLE 125

Global Health and Life Sciences High Performance
Capability Assessment Model - Public Health Services - Medicaid

| | Enterprise | |
|---|---|---|
| Sub-Platform: Information Technology Operations | Capability: Service and Management Operations - Service Support | |

| Basic | Competitive | Market Leading |
|---|---|---|
| Little to no assessment performed prior to service introduction and is mostly informal Support organization readiness assessment informal and ad hoc, mostly individual efforts based Ad hoc development of service related documents, mostly individual efforts based Informal and ad hoc to define configuration items and processes Configuration items loosely identified via ad hoc methods and are not documented Initial efforts to identify dependency between configuration management and other functional processes with no outcomes | Impact analysis performed, service analysis conducted and operability acceptance criteria defined Support organization is base lined (people, process, commercial, financial end operational) and service readiness assessment performed for critical service introductions Service delivery handover matrix developed and documented Business problem identified, process requirements identified and implementation approach documented and articulated All configuration items, labels, data sources, data owners and selection criteria clearly | Service introduction approach proactively reviewed with key stakeholders for sign off A service readiness plan is created and managed detailing a timeline of the key readiness activities that will need to be performed to make organization ready for go-live of the new services Service documents are jointly reviewed with customers and service introduction team Continuous feedback from customers and support group utilized to optimize the matrix Configuration management plan proactively reviewed with key stakeholders for sign off and is updated on a regular basis |

TABLE 125-continued

Global Health and Life Sciences High Performance
Capability Assessment Model - Public Health Services - Medicaid Releases done informally, no preplanning except for staff discussions and some testing at individual or group level
Ad hoc release plans and schedules created and communicated upon request
Ad hoc release testing performed if any
Rollouts done informally, processes vary between groups
Change process exists, but not formalized
Changes are scheduled, usually according to "scheduled maintenance" windows
Change discussed informally. Groups meet to discuss impending changes, but no formal methodology for approval
Post implementation check done informally
Software licenses are reactively controlled and renewed only when licenses expire
Informal audits on an "As Needed" basis
Problem detection is reactive with process initiated by affected users
No formalized method far recording reported problems
Escalation process may exist, but it is haphazard, undocumented and is not monitored
Incident detection is reactive with process initiated by affected users
No single point of contact
Incidents resolution is done reactively utilizing resources available
Escalation process may exist, but it is haphazard, undocumented and is not monitored identified, documented and articulated
Efforts to integrate configuration management with some key service management processes
Standard procedures for building, implementing, and configuring of releases are documented and used across the organization
Release plans and schedules communicated across organization
Clearly, defined release testing procedures exist
Rollout plans documented, communicated and utilized throughout the organization
Formal process specified, documented and enforced
Schedule of changes exists and is available across the organization
Projected service availability is updated with scheduled downtime and distributed across organization
Formal process specified and documented
Change Advisory Board or similar structure is designated to approve changes
Standard methodology documented for post implementation reviews.
Evaluation criteria for post implementation review is identified and established
Defined and well documented software licenses management policies and procedures across organization.
Software is tracked for license expiration and illegal use
Responsibility for tracking and acquiring licenses is specific and limited to a single person or team
Some audits performed using auto discovery or other tools
Clear processes defined as to when/how audit are to be performed
Problem management system and associated staffing identified and budget for staffing, training and support is allocated
Problems logged centrally in a database
A formal process for problem escalation emerging, but still inconsistent across groups
Incident management system and associated staffing identified and budget for staffing, training and support is allocated
Incidents reported reactively to single point of contact
Formal resolution process exists, with appropriate recording of each step in incident database
Responsibilities of each support group are documented and well understood across organization
Responsibilities of each support group are documented and well understood across organization
Some form of knowledge base assists resolution process
A formal process of problem escalation exists, but not consistently followed across groups Configuration manager assigned to manage definition process and involve key stakeholders for input and sign-off
Configuration management database maintained and actively managed
Functional processes an integral part of configuration management process, entire process proactively managed for improvements
Management review of release plans done on a regular basis
Extensive use of tools for work flow, documentation and builds streamline build process and improve reliability
Customers kept aware of impending releases along with schedules and work plan
Release testing feedback proactively integrated to optimize process
Comprehensive rollout plans include dates, times, back out procedures, components affected, etc.
Rollout schedule flexible, can be changed to accommodate problems identified doing testing
Changes are prioritized according to industry accepted priority levels
Proactive change process management using performance data and user input
Change schedules proactively reviewed and optimized using performance metrics and user input
Users proactively notified of impending changes
Change process is proactively monitored and reviewed for enhancements
Financial, technical, business and customer considerations are considered before approval is granted
Post implementation review process continuously reviewed and updated
Post implementation review includes evaluation of customer satisfaction derived from customer feedback
Organization has processes in place to monitor licenses across vendors and operating systems
Active enforcement of system software inventory and ability to track down software that is not authorized or that does not meet security specifications
Software inventories on individual systems monitored via automated technology
Audits scheduled at intervals specified by needs of organization
Mostly automatic, automation runs across operating systems and software
Problem management function is integrated with incident management and categories, impact levels, urgency levels and priority levels are consistent between the two
Problem resolution process is proactively reviewed for enhancements
Escalation processes are well structured and monitored for adherence
The organization tracks problems throughout the lifecycle and knows status at any given time
The incident management function is established and operational responsibilities are clearly defined and documented

TABLE 125-continued

Global Health and Life Sciences High Performance
Capability Assessment Model - Public Health Services - Medicaid

| | | |
|---|---|---|
| | | Incidents captured in incident database for reporting and trending |
| | | Resolution process is reviewed regularly for effectiveness and efficiency |
| | | Staff is highly trained and cross-trained, with no single person who is the sole expert in a particular area |

TABLE 126

Global Health and Life Sciences High Performance
Capability Assessment Model - Public Health Services - Medicaid

| Sub-Platform: Information Technology Operations | Enterprise Capability: Solutions Delivery - Systems Building | |
|---|---|---|
| Basic | Competitive | Market Leading |
| Informal methods exist with loosely defined requirements<br>Each project has a charter and plan<br>Planning and requirements due diligence is IT driven<br>Build techniques and environment at team discretion<br>Projects often begin detailed and technical design with limited requirements due diligence<br>Few templates exist and are used inconsistently<br>Projects have their own processes | Systems Development methodolgy exists and is adhered to at across all projects<br>Stakeholder expectations formally involved in planning<br>Requirements are tracked and controlled with change control<br>Design documents are tracked and controlled and reviewed with enterprise architecture board<br>Formal reviews/steering meetings at the end of each phase<br>Unit and system testing formalized and standardized with sign-off<br>Formal development guidelines in place and consistently followed<br>Formal stage gating factors in place | The standard methodology is flexible enough to encompass the full range of project sizes, types and complexities<br>Incremental benefits explicitly linked to specific requirements and actively managed<br>Post deployment validation a part of enterprise deployment methodology and actively managed<br>Business realization and linkage of systems products to benefits integrated into methodology |

TABLE 127

Global Health and Life Sciences High Performance
Capability Assessment Model - Public Health Services - Medicaid

| Sub-Platform: Information Technology Operations | Enterprise Capability: Solutions Delivery - Systems Maintenance | |
|---|---|---|
| Basic | Competitive | Market Leading |
| Informal systems maintenance processes and standards<br>Only reactive maintenance performed<br>Large problem back log, no prioritization, no maintenance releases<br>No periodic assessment of application portfolio<br>Informal SLAs exist, but rot-well understood<br>Documentation limited; discretionary | Defined service processes for applications<br>Consistently followed across groups<br>Break-fix activity is separated from enhancements<br>Work load is prioritized and triaged weekly<br>Emergency changes are expedited, other changes are assigned to maintenance or development releases<br>SLAs exist for critical applications<br>Controlled approach assures documentation is normally updated during projects and maintenance<br>No coordination of effort to ensure updates are consistent<br>Document includes functional and technical information | Applications assessed for optimal performance on a regular basis<br>Application tiering is frequently reviewed with business regarding business impact<br>SLA metrics are actively tracked and managed with business implications<br>Systems design, operations and user documentation is automatically updated as a part of configuration management<br>Documentation stored electronically and readily available to all groups |

TABLE 128

Global Health and Life Sciences High Performance
Capability Assessment Model - Public Health Services - Medicaid

| Sub-Platform: Information Technology Operations | Enterprise Capability: Strategic IT Alignment - Value Proposition Development | |
|---|---|---|
| Basic | Competitive | Market Leading |
| IT is viewed generally as a cost of doing business, to automate respective business functions<br>There are only informal and verbal business cases for initiatives before they are implemented | Business executives are looking to enhance the use of IT beyond basic process automation, into decision support and patient services areas<br>Discretionary spending is usually a percentage of IT budget<br>A detailed Business Case is developed at the outset with financial measures and metrics (e.g. target run-rate savings) identified, tracked and updated on an ongoing basis | IT funds and resources are allocated to strategic and value-creating operational initiatives<br>CEO and Board Members actively discuss the IT agenda<br>Business case is jointly owned and managed by business and IT |

TABLE 129

Global Health and Life Sciences High Performance
Capability Assessment Model - Public Health Services - Medicaid

| Enterprise | |
|---|---|
| Sub-Platform: Facilities Management | Capability: Manage Facilities and Mail |

Basic 4.7.1.1 Manage Facilities
4.7.1.2 Manage Mail Functions
Manage Intake
Manage Internal Distribution
Manage Privacy and Security of Mail
Manage Processing and Distribution to Postal Service, Private Carriers, etc.

The invention claimed is:

1. A computer-implemented method for high-performance capability assessment of a Medicaid program, comprising:
providing a processor operatively coupled to a communication network;
providing one or more databases operatively coupled to the processor and accessible through the communication network;
coupling an interface to the processor for receiving input;
the processor establishing a machine-readable memory in said one or more databases, including a multidimensional Medicaid program performance reference set comprising multiple key assessment performance reference tables, at least one key assessment performance reference table defining a member management platform, including:
a 'Basic' performance level specifying 'Basic' performance assessment criteria;
a 'Competitive' performance level specifying 'Competitive' performance assessment criteria;
a 'Market Leading' performance level specifying 'Market Leading' performance assessment criteria;
the processor establishing eligibility determination assessment criteria,
wherein the 'Basic' performance assessment criteria includes a first criteria: where information is manually validated;
wherein the 'Competitive' performance assessment criteria includes a first criteria: where application data are standardized;
wherein the 'Market Leading' performance assessment criteria includes a first criteria: where external and internal validation sources automatically send notice of change in member status;
receiving, by the processor, an input specifying a Medicaid program area and a Medicaid program key assessment area with the Medicaid program area for analysis;
searching, by the processor, the multidimensional Medicaid program performance reference set for a matching key assessment performance reference table that matches the Medicaid program area and the Medicaid program key assessment area;
retrieving, by the processor, the matching key assessment performance reference table;
analyzing, by the processor, the matching key assessment performance reference table; and
obtaining, by the processor, a resultant performance level for the Medicaid program key assessment area.

2. The method of claim 1, further including establishing eligibility determination assessment criteria,
wherein the 'Basic' performance assessment criteria includes:
a second criteria: The process is constrained by FAMIS or state eligibility system functionality;
a third criteria: Staff contact external and internal document verification sources via phone, fax;
wherein the 'Competitive' performance assessment criteria includes:
a second criteria: All programs introduce flexibility within benefit packages;
a third criteria: Application data are standardized, all verifications can be automated, rules are consistently applied;
wherein the 'Market Leading' performance assessment criteria includes:
a second criteria: National interoperability permits the eligibility process to send inquiries to any other agency, state, federal, or other entities in any part of the country; and
a third criteria: External and internal validation sources automatically send notice of change in member status.

3. A computer-implemented method for high-performance capability assessment of a Medicaid program, comprising:
providing a processor operatively coupled to a communication network;
providing one or more databases operatively coupled to the processor and accessible through the communication network;

coupling an interface to the processor for receiving input;
the processor establishing a machine-readable memory in said one or more databases, including a multidimensional Medicaid program performance reference set comprising multiple key assessment performance reference tables, at least one key assessment performance reference table defining a member management platform, including:
   a 'Basic' performance level specifying 'Basic' performance assessment criteria;
   a 'Competitive' performance level specifying 'Competitive' performance assessment criteria;
   a 'Market Leading' performance level specifying 'Market Leading' performance assessment criteria;
establishing, by the processor, an enrollment assessment criteria,
   wherein the 'Basic' performance assessment criteria includes a first criteria: where eligibility determination precedes enrollment;
   wherein the 'Competitive' performance assessment criteria includes a first criteria: where contractors and provider query a registry to determine eligibility and program enrollment;
   wherein the 'Market Leading' performance assessment criteria includes a first criteria: where enrollment/ eligibility determination processes are automated services triggered by point of service applications;
receiving, by the processor, an input specifying a Medicaid program area and a Medicaid program key assessment area with the Medicaid program area for analysis;
searching, by the processor, the multidimensional Medicaid program performance reference set for a matching key assessment performance reference table that matches the Medicaid program area and the Medicaid program key assessment area;
retrieving, by the processor, the matching key assessment performance reference table;
analyzing, by the processor, the matching key assessment performance reference table; and
obtaining, by the processor, a resultant performance level for the Medicaid program key assessment area.

4. A computer-implemented method for high-performance capability assessment of a Medicaid program, comprising:
   providing a processor operatively coupled to a communication network;
   providing one or more databases operatively coupled to the processor and accessible through the communication network;
   coupling an interface to the processor for receiving input;
   the processor establishing a machine-readable memory in said one or more databases, including a multidimensional Medicaid program performance reference set comprising multiple key assessment performance reference tables, at least one key assessment performance reference table defining a member management platform, including:
      a 'Basic' performance level specifying 'Basic' performance assessment criteria;
      a 'Competitive' performance level specifying 'Competitive' performance assessment criteria;
      a 'Market Leading' performance level specifying 'Market Leading' performance assessment criteria;
   establishing, by the processor, a member information management assessment criteria,
      wherein the 'Basic' performance assessment criteria includes a first criteria: where information is researched manually;
      wherein the 'Competitive' performance assessment criteria includes a first criteria: where information is shared among entities shared by the agency;
      wherein the 'Market Leading' performance assessment criteria includes a first criteria: where all authorized data exchange partners are able to access member information;
   receiving, by the processor, an input specifying a Medicaid program area and a Medicaid program key assessment area with the Medicaid program area for analysis;
   searching, by the processor, the multidimensional Medicaid program performance reference set for a matching key assessment performance reference table that matches the Medicaid program area and the Medicaid program key assessment area;
   retrieving, by the processor, the matching key assessment performance reference table;
   analyzing, by the processor, the matching key assessment performance reference table; and
   obtaining, by the processor, a resultant performance level for the Medicaid program key assessment area.

5. The method of claim 1, further including establishing a prospective and current member support assessment criteria,
   wherein the 'Basic' performance assessment criteria includes:
      a first criteria: Member communications are primarily conducted via paper and phone;
   wherein the 'Competitive' performance assessment criteria includes:
      a first criteria: Member communications are primarily electronic, with paper used only as needed to reach populations;
   wherein the 'Market Leading' performance assessment criteria includes:
      a first criteria: Certain messages to members are triggered by an individual's entries into personal health records of prospective and current members.

6. A non-transitory computer-readable memory or data storage means encoded with data representing a computer program for a high-performance capability assessment of a Medicaid program, the computer-readable memory or data storage means causing the computer to perform the acts of:
   providing a processor operatively coupled to a communication network;
   providing one or more databases operatively coupled to the processor and accessible through the communication network;
   coupling an interface to the processor for receiving input;
   establishing a machine-readable memory in said one or more databases, including a multidimensional Medicaid program performance reference set comprising multiple key assessment performance reference tables, at least one key assessment performance reference table defining a member management platform, including:
      a 'Basic' performance level specifying 'Basic' performance assessment criteria;
      a 'Competitive' performance level specifying 'Competitive' performance assessment criteria;
      a 'Market Leading' performance level specifying 'Market leading' performance assessment criteria;
   establishing, by the processor, an eligibility determination assessment criteria,
      wherein the 'Basic' performance assessment criteria includes a first criteria: where information is manually validated;

wherein the 'Competitive' performance assessment criteria includes a first criteria: where application data are standardized;

wherein the 'Market Leading' performance assessment criteria includes a first criteria where external and internal validation sources automatically send notice of change in member status;

receiving, by the processor, an input specifying a Medicaid program area and a Medicaid program key assessment area with the Medicaid program area for analysis;

searching, by the processor, the multidimensional Medicaid program performance reference set for a matching key assessment performance reference table that matches the Medicaid program area and the Medicaid program key assessment area;

retrieving, by the processor, the matching key assessment performance reference table;

analyzing, by the processor, the matching key assessment performance reference table; and obtaining, by the processor, a resultant performance level for the Medicaid program industry key assessment area.

7. The computer-readable medium of claim 6 further comprising computer-readable content to cause a computer to perform acts of establishing an eligibility determination assessment criteria, wherein the 'Basic' performance assessment criteria includes:
  a second criteria: The process is constrained by FAMIS or state eligibility system functionality;
  a third criteria: Staff contact external and internal document verification sources via phone, fax;

wherein the 'Competitive' performance assessment criteria includes:
  a second criteria: All programs introduce flexibility within benefit packages;
  a third criteria: Application data is standardized, all verifications can be automated, rules are consistently applied;

wherein the 'Market Leading' performance assessment criteria includes:
  a second criteria: National interoperability permits the eligibility process to send inquiries to any other agency, state, federal, or other entities in any part of the country; and
  a third criteria: External and internal validation sources automatically send notice of change in member status.

8. A non-transitory computer-readable memory or data storage means encoded with data representing a computer program for a high-performance capability assessment of a Medicaid program, the computer-readable memory or data storage means causing the computer to perform the acts of:

providing a processor operatively coupled to a communication network;

providing one or more databases operatively coupled to the processor and accessible through the communication network;

coupling an interface to the processor for receiving input;

establishing a machine-readable memory in said one or more databases, including a multidimensional Medicaid program performance reference set comprising multiple key assessment performance reference tables, at least one key assessment performance reference table defining a member management platform, including:
  a 'Basic' performance level specifying 'Basic' performance assessment criteria;
  a 'Competitive' performance level specifying 'Competitive' performance assessment criteria;
  a 'Market Leading' performance level specifying 'Market leading' performance assessment criteria;

establishing an enrollment assessment criteria,
  wherein the 'Basic' performance assessment criteria includes a first criteria: where eligibility determination precedes enrollment;
  wherein the 'Competitive' performance assessment criteria includes a first criteria: where contractors and provider query a registry to determine eligibility and program enrollment;
  wherein the 'Market Leading' performance assessment criteria includes a first criteria: where enrollment/eligibility determination processes are automated services triggered by point of service applications;

receiving, by the processor, an input specifying a Medicaid program area and a Medicaid program key assessment area with the Medicaid program area for analysis;

searching, by the processor, the multidimensional Medicaid program performance reference set for a matching key assessment performance reference table that matches the Medicaid program area and the Medicaid program key assessment area;

retrieving, by the processor, the matching key assessment performance reference table;

analyzing, by the processor, the matching key assessment performance reference table; and obtaining, by the processor, a resultant performance level for the Medicaid program industry key assessment area.

9. A non-transitory computer-readable memory or data storage means encoded with data representing a computer program for a high-performance capability assessment of a Medicaid program, the computer-readable memory or data storage means causing the computer to perform the acts of:

providing a processor operatively coupled to a communication network;

providing one or more databases operatively coupled to the processor and accessible through the communication network;

coupling an interface to the processor for receiving input;

establishing a machine-readable memory in said one or more databases, including a multidimensional Medicaid program performance reference set comprising multiple key assessment performance reference tables, at least one key assessment performance reference table defining a member management platform, including:
  a 'Basic' performance level specifying 'Basic' performance assessment criteria;
  a 'Competitive' performance level specifying 'Competitive' performance assessment criteria;
  a 'Market Leading' performance level specifying 'Market leading' performance assessment criteria;

establishing a member information management assessment criteria,
  wherein the 'Basic' performance assessment criteria includes a first criteria: where information is researched manually;
  wherein the 'Competitive' performance assessment criteria includes a first criteria: where information is shared among entities shared by the agency;
  wherein the 'Market Leading' performance assessment criteria includes a first criteria: where all authorized data exchange partners are able to access member information;

receiving, by the processor, an input specifying a Medicaid program area and a Medicaid program key assessment area with the Medicaid program area for analysis;

searching, by the processor, the multidimensional Medicaid program performance reference set for a matching key assessment performance reference table that matches the Medicaid program area and the Medicaid program key assessment area;

retrieving, by the processor, the matching key assessment performance reference table;

analyzing, by the processor, the matching key assessment performance reference table; and obtaining, by the processor, a resultant performance level for the Medicaid program industry key assessment area.

10. The computer-readable medium of claim 6 further comprising computer-readable content to cause a computer to perform the acts of establishing a prospective and current member support assessment criteria, wherein the 'Basic' performance assessment criteria includes:
a first criteria: Member communications are primarily conducted via paper and phone;

wherein the 'Competitive' performance assessment criteria includes:
a first criteria: Member communications are primarily electronic, with paper used only as needed to reach populations;

wherein the 'Market Leading' performance assessment criteria includes:
a first criteria: Certain messages to members are triggered by an individual's entries into personal health records of prospective and current members.

11. A system for high-performance capability assessment of a Medicaid program, comprising:

a processor operatively coupled to a communication network;

an interface coupled to the processor configured to receive input;

one or more databases operatively coupled to the processor and accessible through the communication network;

a machine-readable memory operatively located in said one or more databases, said memory including a multidimensional Medicaid program performance reference set comprising multiple key assessment performance reference tables, at least one key assessment performance reference table defining a member management platform, including:
a 'Basic' performance level specifying 'Basic' performance assessment criteria;
a 'Competitive' performance level specifying 'Competitive' performance assessment criteria;
a 'Market Leading' performance level specifying 'Market leading' performance assessment criteria;

the processor establishing an eligibility determination assessment criteria,
wherein the 'Basic' performance assessment criteria includes a first criteria:
where information is manually validated;
wherein the 'Competitive' performance assessment criteria includes a first criteria: where application data are standardized;
wherein the 'Market Leading' performance assessment criteria includes a first criteria: where external and internal validation sources automatically send notice of change in member status;

wherein the processor searches the multidimensional Medicaid program performance reference set for a matching key assessment performance reference table that matches the Medicaid program area and the Medicaid program key assessment area, and retrieves the matching key assessment performance reference table; and wherein the processor performs analysis of the matching key assessment performance reference table; and obtains a resultant performance level for the Medicaid program key assessment area.

12. The system of claim 11, wherein the processor establishes a, eligibility determination assessment criteria,
wherein the 'Basic' performance assessment criteria includes:
a second criteria: The process is constrained by FAMIS or state eligibility system functionality;
a third criteria: Staff contact external and internal document verification sources via phone, fax;
wherein the 'Competitive' performance assessment criteria includes:
a second criteria: All programs introduce flexibility within benefit packages;
a third criteria: Application data is standardized, all verifications can be automated, rules are consistently applied;
wherein the 'Market Leading' performance assessment criteria includes:
a second criteria: National interoperability permits the eligibility process to send inquiries to any other agency, state, federal, or other entities in any part of the country; and
a third criteria: External and internal validation sources automatically send notice of change in member status.

13. A system for high-performance capability assessment of a Medicaid program, comprising:

a processor operatively coupled to a communication network;

an interface coupled to the processor configured to receive input;

one or more databases operatively coupled to the processor and accessible through the communication network;

a machine-readable memory operatively located in said one or more databases, said memory including a multidimensional Medicaid program performance reference set comprising multiple key assessment performance reference tables, at least one key assessment performance reference table defining a member management platform, including:
a 'Basic' performance level specifying 'Basic' performance assessment criteria;
a 'Competitive' performance level specifying 'Competitive' performance assessment criteria;
a 'Market Leading' performance level specifying 'Market leading' performance assessment criteria;

the processor establishing an enrollment assessment criteria,
wherein the 'Basic' performance assessment criteria includes a first criteria: where eligibility determination precedes enrollment;
wherein the 'Competitive' performance assessment criteria includes a first criteria: where contractors and provider query a registry to determine eligibility and program enrollment;
wherein the 'Market Leading' performance assessment criteria includes a first criteria: where enrollment/eligibility determination processes are automated services triggered by point of service applications;

the interface receiving an input specifying a Medicaid program area and a Medicaid program key assessment area with the Medicaid program area for analysis;

wherein the processor searches the multidimensional Medicaid program performance reference set for a matching key assessment performance reference table that matches the Medicaid program area and the Medicaid program key assessment area, and retrieves the matching key assessment performance reference table; and wherein the processor performs analysis of the matching key assessment performance reference table; and obtains a resultant performance level for the Medicaid program key assessment area.

14. A system for high-performance capability assessment of a Medicaid program, comprising:

a processor operatively coupled to a communication network;

an interface coupled to the processor configured to receive input;

one or more databases operatively coupled to the processor and accessible through the communication network;

a machine-readable memory operatively located in said one or more databases, said memory including a multidimensional Medicaid program performance reference set comprising multiple key assessment performance reference tables, at least one key assessment performance reference table defining a member management platform, including:

a 'Basic' performance level specifying 'Basic' performance assessment criteria;

a 'Competitive' performance level specifying 'Competitive' performance assessment criteria;

a 'Market Leading' performance level specifying 'Market leading' performance assessment criteria;

the processor establishing a member information management assessment criteria, wherein the 'Basic' performance assessment criteria includes a first criteria: where information is researched manually;

wherein the 'Competitive' performance assessment criteria includes a first criteria: where information is shared among entities shared by the agency;

wherein the 'Market Leading' performance assessment criteria includes a first criteria: where all authorized data exchange partners are able to access member information;

the interface receiving an input specifying a Medicaid program area and a Medicaid program key assessment area with the Medicaid program area for analysis;

wherein the processor searches the multidimensional Medicaid program performance reference set for a matching key assessment performance reference table that matches the Medicaid program area and the Medicaid program key assessment area, and retrieves the matching key assessment performance reference table; and wherein the processor performs analysis of the matching key assessment performance reference table; and obtains a resultant performance level for the Medicaid program key assessment area.

15. The system of claim 11, wherein the processor establishes a prospective and current member support assessment criteria, wherein the 'Basic' performance assessment criteria includes:

a first criteria: Member communications are primarily conducted via paper and phone;

wherein the 'Competitive' performance assessment criteria includes:

a first criteria: Member communications are primarily electronic, with paper used only as needed to reach populations;

wherein the 'Market Leading' performance assessment criteria includes:

a first criteria: Certain messages to members are triggered by an individual's entries into personal health records of prospective and current members.

\* \* \* \* \*